(12) United States Patent
Yang et al.

(10) Patent No.: US 11,554,127 B2
(45) Date of Patent: Jan. 17, 2023

(54) SYNERGISTIC ANTITUMOR EFFECT OF BCL-2 INHIBITOR COMBINED WITH RITUXIMAB AND/OR BENDAMUSTINE OR BCL-2 INHIBITOR COMBINED WITH CHOP

(71) Applicant: ASCENTAGE PHARMA (SUZHOU) CO., LTD., Suzhou (CN)

(72) Inventors: Dajun Yang, Suzhou (CN); Yifan Zhai, Suzhou (CN); Guangfeng Wang, Suzhou (CN)

(73) Assignee: ASCENTAGE PHARMA (SUZHOU) CO., LTD., Suzhou (CN)

( * ) Notice: Subject to any disclaimer, the term of this patent is extended or adjusted under 35 U.S.C. 154(b) by 0 days.

(21) Appl. No.: 16/648,593

(22) PCT Filed: Jul. 22, 2019

(86) PCT No.: PCT/CN2019/097028
§ 371 (c)(1),
(2) Date: Mar. 18, 2020

(87) PCT Pub. No.: WO2020/024826
PCT Pub. Date: Feb. 6, 2020

(65) Prior Publication Data
US 2021/0361678 A1    Nov. 25, 2021

(30) Foreign Application Priority Data
Jul. 31, 2018 (CN) .......................... 201810867252.2

(51) Int. Cl.
| A61K 31/635 | (2006.01) |
| A61P 35/00 | (2006.01) |
| A61K 31/4184 | (2006.01) |
| A61K 45/06 | (2006.01) |
| C07K 16/28 | (2006.01) |

(52) U.S. Cl.
CPC ........ *A61K 31/635* (2013.01); *A61K 31/4184* (2013.01); *A61K 45/06* (2013.01); *A61P 35/00* (2018.01); *C07K 16/2887* (2013.01)

(58) Field of Classification Search
CPC . C07K 16/2887; A61P 35/00; A61K 31/4184; A61K 45/06
See application file for complete search history.

(56) References Cited

U.S. PATENT DOCUMENTS

| 8,546,399 | B2 | 10/2013 | Bruncko et al. | |
| 10,213,433 | B2 | 2/2019 | Catron et al. | |
| 10,221,174 | B2 | 3/2019 | Wang et al. | |
| 10,829,488 | B2* | 11/2020 | Wang | A61P 35/00 |
| 2009/0098118 | A1* | 4/2009 | Friess | A61K 39/39558 424/173.1 |
| 2010/0305122 | A1 | 12/2010 | Bruncko et al. | |
| 2011/0124628 | A1 | 5/2011 | Bruncko et al. | |
| 2012/0028925 | A1 | 2/2012 | Tao et al. | |
| 2012/0157470 | A1 | 6/2012 | Catron et al. | |
| 2015/0329541 | A1 | 11/2015 | Bruncko et al. | |
| 2016/0347852 | A1* | 12/2016 | Klein | A61K 45/06 |
| 2018/0354950 | A1* | 12/2018 | Wang | A61P 35/02 |
| 2019/0315739 | A1* | 10/2019 | Wang | A61P 35/02 |
| 2020/0222393 | A1* | 7/2020 | Yang | A61P 35/00 |
| 2021/0002277 | A1* | 1/2021 | Wang | A61P 35/02 |
| 2021/0137949 | A1* | 5/2021 | Yang | A61P 35/00 |
| 2021/0275522 | A1* | 9/2021 | Yang | A61K 45/06 |
| 2022/0031694 | A1* | 2/2022 | Yang | A61K 45/06 |
| 2022/0143039 | A1* | 5/2022 | Yang | A61K 45/06 |
| 2022/0233558 | A1* | 7/2022 | Zhai | A61P 35/00 |

FOREIGN PATENT DOCUMENTS

| CN | 101918420 A | 12/2010 |
| CN | 103402521 B | 1/2016 |
| CN | 105246882 A | 1/2016 |
| CN | 105061315 B | 10/2017 |
| CN | 106794171 B | 3/2020 |
| JP | 2013526612 A | 6/2013 |
| JP | 2013540823 A | 11/2013 |
| JP | 2013543894 A | 12/2013 |
| WO | WO 2005/049593 A2 | 6/2005 |
| WO | WO 2008/030836 A2 | 3/2008 |
| WO | WO 2008/070663 A2 | 6/2008 |
| WO | WO 2010/065824 A2 | 6/2010 |
| WO | WO 2010/065865 A2 | 6/2010 |
| WO | WO 2010/093742 A1 | 8/2010 |
| WO | WO 2010/138588 A2 | 12/2010 |
| WO | WO 2011/068863 A1 | 6/2011 |
| WO | WO 2011/149492 A1 | 12/2011 |
| WO | WO 2012/058392 A1 | 5/2012 |

(Continued)

OTHER PUBLICATIONS

Lim; Haematologica 2010, 95, 135-143. doi: 10.3324/haematol. 2008.001628 (Year: 2010).*
Zinzani; Blood 2016, 128, 617. 4 pages. https://doi.org/10.1182/blood.V128.22.617.617 (Year: 2016).*
Prescribing information for VENCLEXTA (venetoclaxtablets). 32 pages. Jun. 2018. (Year: 2018).*
Ackler et al., "The Bcl-2 inhibitor ABT-263 enhances the response of multiple chemotherapeutic regimens in hematologic tumors in vivo." *Cancer Chemotherapy and Pharmacology.*, vol. 66, No. 5, (Jan. 2010), pp. 869-880.
Adams et al., "The Bcl-2 apoptotic switch in cancer development and therapy," *Oncogene*, 26(9), pp. 1324-1337, (2007).

(Continued)

*Primary Examiner* — Daniel R Carcanague
(74) *Attorney, Agent, or Firm* — Barnes & Thornburg LLP

(57) ABSTRACT

Provided herein is a combination product comprising a Bcl-2 inhibitor, an anti-CD20 antibody and/or bendamustine or a combination product comprising a Bcl-2 inhibitor and CHOP, the combination product provides a use of the combination product for prevention and/or treatment of a disease (e.g., cancer, rheumatoid arthritis (RA), granulomatosis with polyangiitis (GPA), and microscopic polyangiitis).

12 Claims, 5 Drawing Sheets

(56) References Cited

FOREIGN PATENT DOCUMENTS

| WO | WO 2012/071374 A1 | 5/2012 | | |
|---|---|---|---|---|
| WO | WO 2012/103059 A2 | 8/2012 | | |
| WO | WO 2014/113413 A1 | 7/2014 | | |
| WO | WO 2015/130585 A1 | 9/2015 | | |
| WO | WO 2015/161032 A1 | 10/2015 | | |
| WO | WO 2016/024230 A1 | 2/2016 | | |
| WO | WO 2017/037579 A1 | 3/2017 | | |
| WO | WO 2018/027097 A1 | 2/2018 | | |
| WO | WO 2020/024820 A1 | 2/2020 | | |
| WO | WO 2020/024826 A1 | 2/2020 | | |
| WO | WO 2020/024834 A1 | 2/2020 | | |
| WO | WO 2020/024916 A1 | 2/2020 | | |
| WO | WO 2020/103921 A1 | 5/2020 | | |
| WO | WO-2021000899 A1 * | 1/2021 | ........... | A61K 31/436 |
| WO | WO-2021110097 A1 * | 6/2021 | ........... | A61K 31/454 |

OTHER PUBLICATIONS

Adams et al., "The Bcl-2 protein family: arbiters of cell survival," Science, 281 (5381), pp. 1322-1326, (1998).
Aguilar et al., "Discovery of 4-((3'R,4'S,5'R)-6"-Chloro-4'-(3-chloro-2-fluorophenyl)-1'-ethyl-2"-oxodispiro[cyclohexane-1,2'-pyrrolidine-3',3"-indoline]-5'-carboxamido)bicycle[2,2,2]octane-l-carboxylic Acid (AA-115/APG-115): a Potent and Orally Active Murine Double Minute 2 (MDM2) Inhibitor in Clinical Development," J. Med. Chem. 2017, 60, pp. 2819-2839.
Amundson et al., "An informatics approach identifying markers of chemosensitivity in human cancer cell lines," Cancer Res., 60(21), pp. 6101-6110, (2000).
Bai L., et al., "BM-1197: a Novel and Specific Bcl-2/Bcl-xL Inhibitor Inducing Complete and Long-Lasting Tumor Regression in Vivo," PloS One, vol. 9, No. 6, (Jun. 2014), pp. 399404-e99404.
Bingham et al., "Over one hundred solvates of sulfathiazole," Chem. Commun., pp. 603-604, (2001).
Bogenberger et al., "Combined venetoclax and alvocidib in acute myeloid leukemia," Oncotarget., vol. 8, No. 63, (Nov. 2017), pp. 107206-107222.
Caira et al., "Preparation and crystal characterization of a polymorph, a monohydrate, and an ethyl acetate solvate of the antifungal fluconazole," J. Pharm. Sci., 93(3), pp. 601-611, (2004).
Cang et al., "ABT-199 (venetoclax) and BCL-2 inhibitors in clinical development," J. Hematol. Oncol., 8, pp. 129, (2015).
Chen et al., "The Bcl-2/Bcl-X-L/Bcl-w Inhibitor, Navitoclax, Enhances the Activity of Chemotherapeutic Agents in Vitro and in Vivo," Molecular Cancer Therapeutics., vol. 11, No. 12, (Sep. 2011), pp. 2340-2349.
Danial et al., "Cell death: critical control points," Cell, 116(2), pp. 205-219, (2004).
Dey et al., "Voruciclib, a clinical stage oral CDK9 inhibitor, represses MCL-1 and sensitizes high-risk Diffuse Large B-cell Lymphoma to BCL2 inhibition," Scientific Reports 7:18007, pp. 1-11, (2017).
Dorwald F.A., "Side Reactions in Organic Synthesis," Wiley: VCH, Weinheim, pp. IX of Preface pp. 1-15, (2005).
Huang, "Fluorescence polarization competition assay: the range of resolvable inhibitor potency is limited by the affinity of the fluorescent ligand," J. Biomol. Screen., 8(1), pp. 34-38, (2003).
Inoue-Yamauchi, Akane et al., "Targeting the differential addiction to anti-apoptotic bcl-2 family for cancer therapy," Nature Communications, vol. 8, (Jul. 2017), pp. 1-14.
International Search Report and Written Opinion for PCT/CN2019/096968, dated Oct. 22, 2019.
International Search Report and Written Opinion for PCT/CN2019/097028, dated Oct. 22, 2019.
International Search Report and Written Opinion for PCT/CN2019/097081, dated Oct. 29, 2019.
International Search Report and Written Opinion for PCT/CN2019/098252, dated Nov. 4, 2019.
International Search Report and Written Opinion for PCT/CN2019/120144, dated Feb. 24, 2020.
International Search Report for PCT/US2017/045428, dated Nov. 17, 2017.
Kirkin et al., "The role of Bcl-2 family members in tumorigenesis," Biochem. Biophys. Acta., 1644(2-3), pp. 229-249, (2004).
Kojima et al., "Concomitant Inhibition of MDM2 and Bcl-2 Protein Function Synergistically Induce Mitochondrial Apoptosis in AML," Cell Cycle, vol. 5, Iss. 23, pp. 2778-2786, (Dec. 2006).
Lehmann, Christian et al, "Superior anti-tumor activity of the MDM2 antagonist idasanutlin and the Bcl-2 inhibitor venetoclax in p53 wild-type acute myeloid leukemia models," Journal of Hematology & Oncology, (2016), 9:50; pp. 1-13.
Metro, G. and Cappuzzo, Federico, "Emerging drugs for small-cell lung cancer," Expert Opin. Emerging Drugs, 14(4), pp. 591-606, (2009).
Moss, "Basic terminology of stereochemistry," Pure & Appl. Chem., 68(12), pp. 2193-2222, (1996).
Nakayama et al., "Targeted disruption of Bcl-2 alpha beta in mice: occurrence of gray hair, polycystic kidney disease, and lymphocytopenia," Proc. Natl. Acad. Sci. USA, 91(9), pp. 3700-3704, (1994).
Nikolovska-Coleska et al., "Development and optimization of a binding assay for the XIAP BIR3 domain using fluorescence polarization," Anal. Biochem., 332(2), pp. 261-273, (2004).
Pan et al., "Activation of p56 by Novel MDM2 Antagonist RG7388 Overcomes AML Inherent and Acquired Resistance to Bcl-2 Inhibitor ABT-199 (GDC-0199)," Blood, 124:2162; (2014).
Portell et al., "Abstract B40: Synergistic cytotoxicity of ibrutinib and the BCL2 antagonist Abt-199 in mantle cell lymphoma and chronic lymphocytic leukemia: Molecular analysis reveals mechanisms of target interactions," Hematologic Malignancies, vol. 21, Issue 17, (Sep. 2015).
Reed et al., "Bcl-2 family proteins: regulators of cell death involved in the pathogenesis of cancer and resistance to therapy," J. Cell Biochem., 60(1), pp. 23-32, (1996).
Reed, "Bcl-2 family proteins: strategies for overcoming chemoresistance in cancer," Adv. Pharmacol., 41, pp. 501-532, (1997).
Souers et al., "ABT-199, a potent and selective BCL-2 inhibitor, achieves antitumor activity while sparing platelets," Nat. Med., 19(2), pp. 202-208, (2013).
Tse et al., "ABT-263: a potent and orally bioavailable Bcl-2 family inhibitor," Cancer Res., 68(9), pp. 3421-3428, (2008).
van Delft et al., "The BH3mimetic ABT-737 targets selective Bcl-2 proteins and efficiently induces apoptosis vai Bak/Bax if Mcl-1 is neutralized," Cancer Cell, 10(5), pp. 389-399, (2006).
Van Goethem et al., "Dual targeting of MDM2 and BCL2 as a therapeutic strategy in neuroblastoma," Oncotarget, vol. 8, No. 34, (2017), pp. 57047-57057.
van Tonder et al., "Preparation and physicochemical characterization of 5 niclosamide solvates and 1 hemisolvate," AAPS PharmSciTech., 5(1), E12, (2004).
Venclexta, Venclexta tablets label, Translation (Dec. 14, 2017).
Venkatesh, J., "Role of the Development Scientist in Compound Lead Selection and Optimizatin" J. Pharm. Sci., vol. 89, No. 2, pp. 145-154, (2000).
Willis et al., "Apoptosis initiated when BH3 ligands engage multiple Bcl-2 homologs, not Bax or Bak," Science, 315(5813), pp. 856-859, (2007).
Written Opinion of the International Searching Authority for PCT/US2017/045428, dated Nov. 17, 2017.
Zhang, "Apoptosis-based anticancer drugs," Nat. Rev. Drug Discov., 1(2), pp. 101-102, (2002).
Seymour et al., "Venetoclax plus rituximab in relapsed or refractory chronic Tymphocytic leukaemia: a phase 1b study," Lancet Onco. (Feb. 2017) 18(2), pp. 230-240.
Zelenetz et al., "Results of a Phase 1b Study of Venetoclax Plus R- or G-CHOP in Patients with B-Cell Non-Hodgkin Lymphoma," Blood, (Dec. 2016), vol. 128(22), pp. 3032-3035.

(56) References Cited

OTHER PUBLICATIONS

Zinzani et al., "Phase 2 Study of Venetoclax Plus Rituximab or Randomized Ven Plus Bendamustine+Rituximab (BR) Versus BR in Patients ith Relapsed/Refractory Follicular Lymphoma: Interim Data," Blood, (Dec. 2016), vol. 128(22), pp. 617-620.

* cited by examiner

A.

B.

A.

B.

A.

B.

SYNERGISTIC ANTITUMOR EFFECT OF BCL-2 INHIBITOR COMBINED WITH RITUXIMAB AND/OR BENDAMUSTINE OR BCL-2 INHIBITOR COMBINED WITH CHOP

CROSS REFERENCE TO RELATED APPLICATIONS

This application is a national phase application of PCT/CN2019/097028, filed Jul. 22, 2019, which application claims the benefit of and priority to Chinese Patent Application No. 201810867252.2, filed Jul. 31, 2018, the entire contents of each of which are incorporated by reference herein.

TECHNICAL FIELD

The invention belongs to the technical field of medical technology, and particularly relates to a combination product comprising a Bcl-2 inhibitor, an anti-CD20 antibody and/or bendamustine or a combination product comprising a Bcl-2 inhibitor and CHOP, the combination product provides for a use in the prevention and/or treatment of diseases (e.g, cancers, rheumatoid arthritis (RA), granulomatosis with polyangiitis (GPA) and microscopic polyangiitis).

BACKGROUND ART

Apoptosis (programmed cell death) is a natural pathway for the body to clear abnormal or unwanted cells, which can cause various diseases such as cancers if affected.

Anti-apoptotic Bcl-2 proteins are associated with many diseases. Bcl-2 family proteins are key regulators in the mitochondria-mediated apoptotic pathway. Escape from apoptosis is one of the characteristics of human cancers and is a common cause of clinical drug resistances.

In approximately one-third of patients with diffuse large B-cell lymphoma (DLBCL), BCL-2 protein is highly expressed. Therefore, targeting BCL-2 protein to induce apoptosis is considered to be an effective method for treating B cell lymphoid malignancies. However, long-term use of BCL-2 inhibitors may induce drug resistance. The mechanisms of drug resistance include induction of expression of other anti-apoptotic proteins, such as MCL-1 and BCL-XL, continuous activation of intracellular signaling (i.e, downstream BCR signaling), etc. (Youle R J, Strasser A. The BCL-2 protein family: opposing activities that mediate cell death. Nat Rev Mol Cell Biol. 2008; 9(1): 47-59). Studies have shown that acquired drug resistance is induced by long-term exposure to BCL-2 inhibitors in DLBCL cell lines, resulting in a large number of AKT activation and up-regulation of MCL-1 and BCL-xL levels (Choudhary G S, Al-Harbi S, Mazumder S, et Al. MCL-1 and BCL-xL dependent resistance to the BCL-2 inhibitor ABT-199 can be overcome by preventing PI3K/AKT/mTOR activation in lymphoid malignancies. Cell Death Dis. 2015; 6: e1593).

Other studies have shown that the second-generation anti-CD20 antibody, obinutuzumab, blocks the expression of BCL-xL by inhibiting the activation of NF-κB signaling pathway (Chiron D, Bellanger C, Papin A, et al. Rational targeted therapies to overcome microenvironment-dependent expansion of mantle cell lymphoma. Blood. 2016; 128(24): 2808-2818).

With the advancement of molecular biology, molecular targeted therapy has become a hotspot in medical research (especially tumor research). The biological behavior of most tumors is not dominated by a single signaling pathway, but multiple signaling pathways work together. Therefore, there is a need in the prior art for a regimen and product of drugs in combination which aim at different target proteins and/or different signaling pathways, and the regimen and product of drugs in combination can reduce the dose of single drug, reduce the side effects of the single drug and/or act in a synergistic manner to achieve prevention and/or treatment of disease.

Contents of the Invention

In order to meet the needs in the prior art, the present invention provides a combination product comprising a Bcl-2 inhibitor, an anti-CD20 antibody and/or bendamustine, or a combination product comprising a Bcl-2 inhibitor and CHOP, the combination product provides for a use in the prevention and/or treatment of diseases (e.g, cancers, rheumatoid arthritis (RA), granulomatosis with polyangiitis (GPA) and microscopic polyangiitis).

Specifically, a first aspect of the invention relates to a combination product comprising a Bcl-2 inhibitor and an anti-CD20 mAb. Also, the present invention relates to a combination product comprising a Bcl-2 inhibitor, an anti-CD20 mAb and bendamustine. Further, the present invention relates to a combination product comprising a Bcl-2 inhibitor and CHOP (cyclophosphamide, doxorubicin, vincristine and prednisone).

In some embodiments, the Bcl-2 inhibitor is a compound of Formula I-A or a pharmaceutically acceptable salt or solvate thereof:

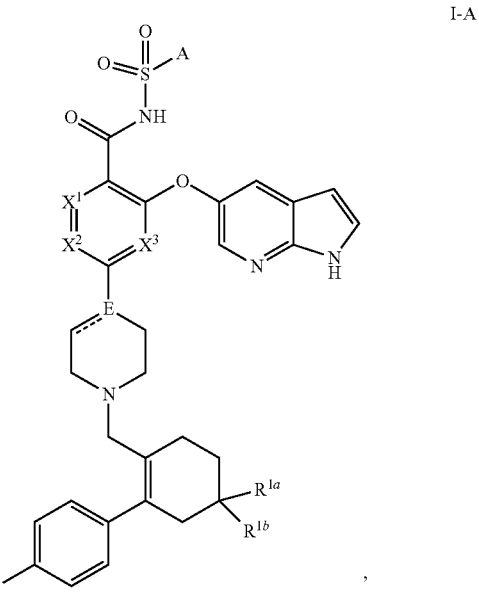

wherein:
A is

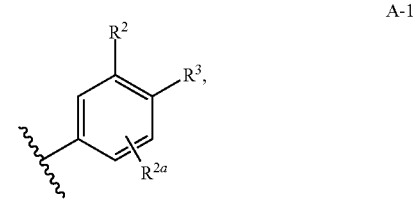

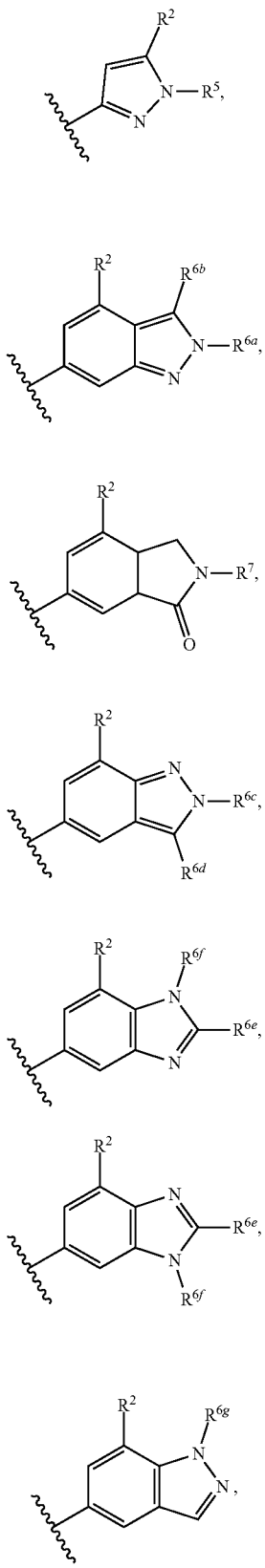

E is a carbon atom and ═══ is a double bond; or

E is a —C(H)— and ═══ is a single bond; or

E is a nitrogen atom and ═══ is a single bond;

X1, X2 and X3 are each independently selected from the group consisting of —CR8═ and —N═;

R1a and R1b taken together with the carbon atom to which they are attached form a 3-, 4-, or 5-membered optionally substituted aliphatic ring; or R1a and R1b taken together with the carbon atom to which they are attached form a 4- or 5-membered optionally substituted heterocyclo;

R2 is selected from the group consisting of —NO2, —SO2CH3, and —SO2CF3;

R2a is selected from the group consisting of hydrogen and X;

R3 is selected from the group consisting of hydrogen, —CN, —C≡CH, and —N(R4a)(R4b);

R4a is selected from the group consisting of optionally substituted C1-6 alkyl, optionally substituted C3-6 cycloalkyl, heterocyclo, heteroalkyl, cycloalkylalkyl, and heterocycloalkyl;

R4b is selected from the group consisting of hydrogen and C14 alkyl;

R5 is selected from the group consisting of is selected from the group consisting of optionally substituted C1-6 alkyl, heterocyclo, cycloalkylalkyl, and heterocycloalkyl;

R6a, R6c, R6e, R6f, and R6g are each independently selected from the group consisting of hydrogen, optionally substituted C1-6 alkyl, optionally substituted C3-6 cycloalkyl, optionally substituted aryl, optionally substituted heteroaryl, heterocyclo, heteroalkyl, cycloalkylalkyl, and heterocycloalkyl;

R6b and R6d are each independently selected from the group consisting of hydrogen, C1-4 alkyl, and halogen;

R7 is selected from the group consisting of optionally substituted C1-6 alkyl, heterocyclo, heteroalkyl, cycloalkylalkyl, and heterocycloalkyl; and R8 is selected from the group consisting of hydrogen and halogen.

In some embodiments, the Bcl-2 inhibitor is selected from the group consisting of the following compounds or pharmaceutically acceptable salts or solvates thereof:

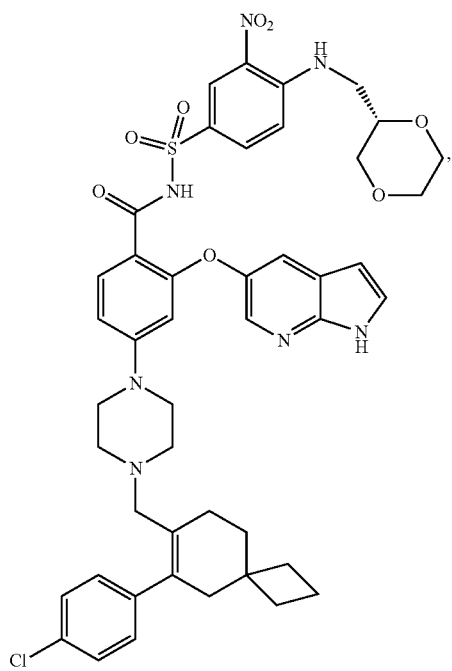 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

or

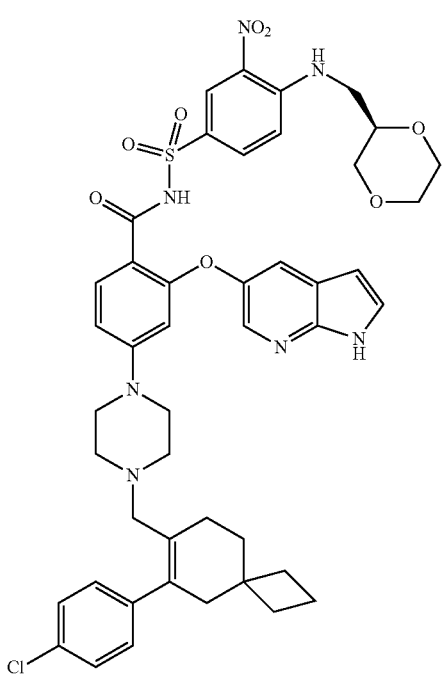

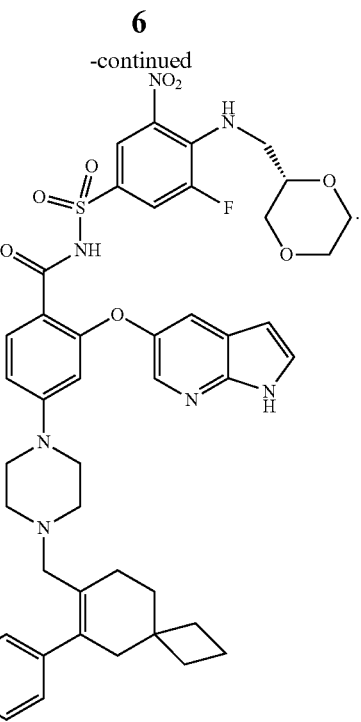

In some embodiments, the Bcl-2 inhibitor is the following compound or a pharmaceutically acceptable salt or solvate thereof:

In some embodiments, the anti-CD20 mAb is selected from the group consisting of: Rituximab, IF5, Ibritumomab tiuxetan, tositumomab, ocrelizumab, veltuzumab, ofatumumab, obinutuzumab, AME133V, Pro13192 and GA101, TRU-015.

In some embodiments, the combination product is in the form of a pharmaceutical composition.

In some embodiments, the Bcl-2 inhibitor and the anti-CD20 mAb are each in a separate preparation.

In some embodiments, the Bcl-2 inhibitor, anti-CD20 mAb and bendamustine are each in a separate preparation.

In some embodiments, the Bcl-2 inhibitor and CHOP are each in a separate preparation.

In some embodiments, the Bcl-2 inhibitor and anti-CD20 mAb are administered simultaneously, sequentially or alternately.

In some embodiments, the Bcl-2 inhibitor, anti-CD20 mAb and bendamustine are administered simultaneously, sequentially or alternately.

In some embodiments, the Bcl-2 inhibitor and CHOP are administered simultaneously, sequentially or alternately.

In some embodiments, the combination product further comprises a pharmaceutically acceptable carrier, diluent or excipient.

In some embodiments, wherein the combined product is in the form of tablet, capsule, granule, syrup, powder, lozenge, sachet, cachet, elixir, suspension, emulsion, solution, syrup, aerosol, ointment, cream and injection.

A second aspect of the invention relates to the use of a Bcl-2 inhibitor and an anti-CD20 mAb in the manufacture of a medicament for the prevention and/or treatment of a disease selected from the group consisting of cancer, rheumatoid arthritis (RA), granulomatosis with polyangiitis (GPA) and microscopic polyangiitis.

Meanwhile, the present invention relates to a use of a Bcl-2 inhibitor, an anti-CD20 mAb and bendamustine in the manufacture of a medicament for the prevention and/or treatment of a disease selected from the group consisting of cancer, rheumatoid arthritis (RA)), granulomatosis with polyangiitis (GPA) and microscopic polyangiitis.

Further, the present invention relates to the use of a Bcl-2 inhibitor and CHOP in the manufacture of a medicament for the prevention and/or treatment of a disease, wherein the disease is cancer.

A third aspect of the invention relates to a combination product for the prevention and/or treatment of a disease, in which the combination product comprises a Bcl-2 inhibitor and an anti-CD20 mAb, and the disease is selected from the group consisting of cancer, rheumatoid arthritis (RA), granulomatosis with polyangiitis (GPA) and microscopic polyangiitis.

Meanwhile, the present invention relates to a combination product for preventing and/or treatment of a disease, in which the combination product comprises a Bcl-2 inhibitor, an anti-CD20 mAb and Bendamustine, and the disease is selected from the group consisting of cancer, rheumatoid arthritis (RA), granulomatosis with polyangiitis (GPA) and microscopic polyangiitis.

Further, the present invention relates to a combination product for the prevention and/or treatment of a disease, in which the combination product comprises a Bcl-2 inhibitor and CHOP, and the disease is cancer.

A fourth aspect of the invention relates to a method for the prevention and/or treatment of a disease comprising administering to a subject in need thereof a prophylactically and/or therapeutically effective amount of a Bcl-2 inhibitor and an anti-CD20 mAb, in which the disease is selected from the group consisting of cancer, rheumatoid arthritis (RA), granulomatosis with polyangiitis (GPA) and microscopic polyangiitis.

At the same time, the invention relates to a method for the prevention and/or treatment of a disease, comprising administering to a subject in need thereof a prophylactically and/or therapeutically effective amount of a Bcl-2 inhibitor, an anti-CD20 mAb and Bendamustine, in which the disease is selected from the group consisting of cancer, rheumatoid arthritis (RA), granulomatosis with polyangiitis (GPA) and microscopic polyangiitis.

Further, the present invention relates to a method for the prevention and/or treatment of a disease, comprising administering to a subject in need thereof a prophylactically and/or therapeutically effective amount of a Bcl-2 inhibitor and CHOP, and the disease is cancer.

DEFINITIONS

Figure 1:
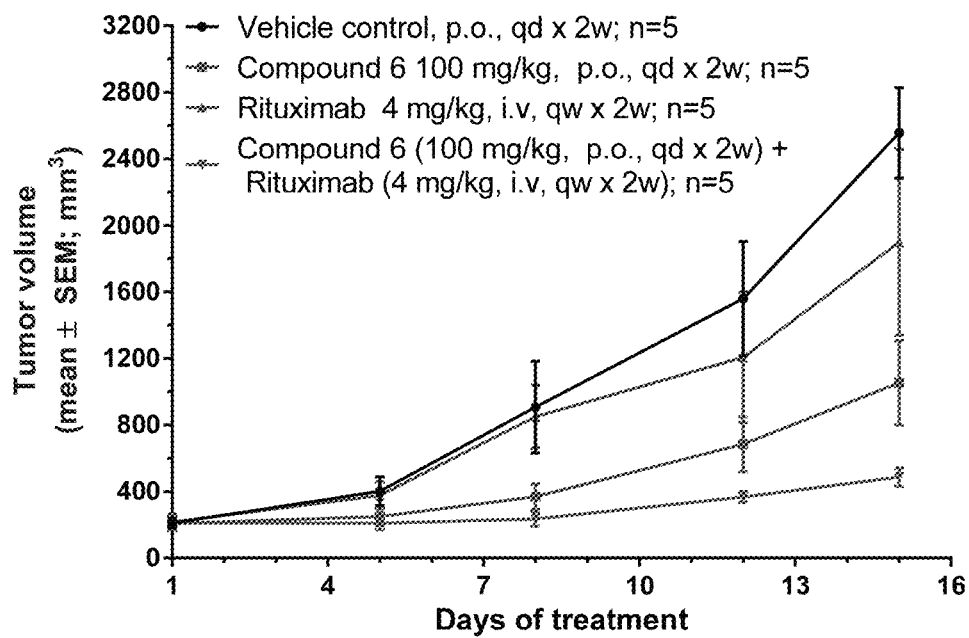
FIG. 1 shows the anti-tumor effect (A) and body weight change (B) caused by Compound 6 alone or in combination with rituximab in a human Toledo (DLBCL) mouse xenograft model.
Figure 1:
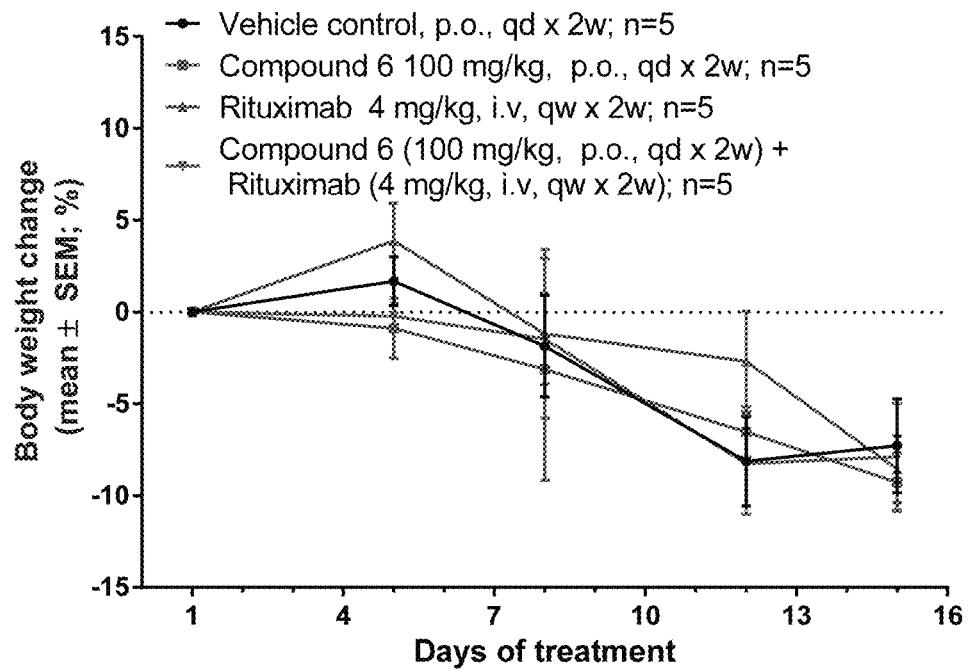

The term "anti-CD mAb" as used herein refers to an immunoglobulin, such as a monoclonal or polyclonal antibody from an animal or human specific to a CD20 receptor, a cell surface antigen or a cell surface determinant.

The term "pharmaceutically acceptable salt" as used herein, refers to a salt of a free acid or a free base, usually prepared by reacting the free base with a suitable organic or inorganic acid or by reacting the acid with a suitable organic or inorganic base. This term can be used in any of the compounds of the invention. Representative salts include: acetate, besylate, benzoate, bicarbonate, hydrogen sulfate, hydrogen tartrate, borate, bromide, calcium edetate, camphorsulfonate, carbonate, chloride, clavulanate, citrate, dihydrochloride, edetate, ethanedisulfonate, estolate, esylate, fumarate, glucoheptonate, gluconate, glutamate, glycolylarsanilate, hexylresorcinate, hydrabamine, hydrobromide, hydrochloride, hydroxynaphthoate, iodide, isethionate, lactate, lactobionate, laurate, malate, maleate, mandelate, methanesulfonate, methylbromide, methylnitrate, methylsulfate, monopotassium maleate, mucate, naphthalenesulfonate, nitrate, N-methylglucosamine salt, oxalate, pamoate (dihydroxylnaphthalate), palmitate, pantothenate, phosphate/diphosphate, polygalacturonate, potassium salt, salicylate, sodium salt, stearate, subacetate, succinate, tannate, tartrate, teoclate, p-toluenesulfonate, triethiodide, trimethylamine salt and valerate. When an acidic substituent is present, such as —COOH, an ammonium salt, morpholine salt, sodium salt, potassium salt, barium salt, calcium salt or the like can be formed for use in a dosage form. When a basic group is present (for example, in a limonoid compound or a 1,1-dimethylbiguanide), such as an amino group or basic heteroaryl group such as a pyridyl group, an acidic salt can be formed, such as hydrochloride, hydrobromide, phosphate, sulfate, trifluoroacetate, trichloroacetate, acetate, oxalate, maleate, pyruvate, malonate, succinate, citrate, tartrate, fumarate, mandelate, benzoate, cinnamate, methanesulfonate, ethanesulfonate, picrate, and the like.

The term "prevention/preventing" as used herein refers to a compound or medicament (e.g, a combination product as claimed herein) can reduce a frequency of a symptom of a medical condition in a subject or delay the onset thereof when it is applied to a disease or condition (e.g., cancer), in comparison with a subject to which the compound or medicament is not applied.

The term "treatment/treating" as used herein refers to reducing, alleviating or ameliorating a symptoms of a disease or condition, ameliorating a symptom caused by a potential metabolism, inhibiting a disease or symptom, such as preventing a disease or a disorder from progression, ameliorating a disease or condition, causing regression of a disease or condition, alleviating a condition caused by a disease or condition, or preventing a symptom of a disease or condition.

The term "cancer" as used herein refers to a neoplasm or tumor caused by abnormal, uncontrolled cell growth. Non-limiting examples include those exemplary cancers described in the detailed description of the invention. The term "cancer" includes diseases involving both pre-malignant cancer cells and malignant cancer cells.

The term "solvate" as used herein is a combination, physical binding, and/or solvation of a compound of the invention with a solvent molecule, such as a disolvate, a monosolvate, a hemisolvate. The compounds of the present invention may be in a solvate form with a pharmaceutically acceptable solvent such as water, methanol, ethanol, etc., which does not significantly affect the pharmacological activity or toxicity of the compounds and which may act as a pharmacological equivalent.

The term "subject" as used herein refers to including humans (e.g., patients) and animals (e.g, mice, rats, dogs, cats, rabbits, chickens, monkeys, etc.). When the subject is a human patient (usually calculated as body weight of 60 kg), a dose described herein can be obtained by conversion performed with a conversion factor for an experimental animal (e.g, human dose=mouse dose/12.3) unless otherwise stated (Kin Tam. "Estimating the "First in human" dose—a revisit with particular emphasis on oncology drugs, ADMET & DMPK 1 (4) (2013) 63-75). Those of ordinary skill in the art can reasonably adjust the dose based on common sense and according to the specific weight of subject, the type and severity of disease, and other factors, and all of these adjusted technical solutions fall within the scope of the technical solutions claimed in the present invention.

The term "effective amount" or "prophylactically and/or therapeutically effective amount" as used herein refers to a sufficient amount (e.g, a dose) of a medicament or compound to be administered that will alleviate one or more symptoms of a disease or condition to be treated to some extent. The result can be a reduction and/or alleviation in the cause of the condition or disease or any other desired changes in biological system. For example, an "effective amount" for therapeutic use is an amount of a compound or medicament (e.g, a combination product as claimed herein) that provides a significant reduction in the clinical symptoms of the disease or condition without causing excessive toxic side effects.

The term "dose" as used herein refers to a weight (e.g, milligrams (mg)) of an active substance per kilogram (kg) of a subject's body weight.

The term "IC50" as used herein refers to an amount, concentration or dose of a particularly tested compound or medicament that achieves a 50% inhibition of maximum effect in an assay that measures such effect, for example inhibition of BCL-2 or BTK.

The term "room temperature" as used herein refers to 25° C.±1° C. At the same time, if the experimental temperature is not specified, it is room temperature.

The term "about" as used herein refers to ±10%, more preferably ±5%, and most preferably ±2% of the value modified by the term, so that one of ordinary skill in the art can clearly determine the scope of the term "about" according to the modified value.

The terms "aliphatic ring", "heterocycle", "heterocycloalkyl", "heteroalkyl", "cycloalkylalkyl" and "halogen" as used herein have the ordinary meanings in the art, and a person of ordinary skill in the art will be able to understand the meaning thereof by the general knowledge or by reference to the prior art (for example, WO 2018/027097, the entire disclosure of which is incorporated herein by reference).

Detailed Description of the Invention

A first aspect of the invention relates to a combination product comprising or consisting of a Bcl-2 inhibitor and an anti-CD20 mAb.

Also, the present invention relates to a combination product comprising or consisting of a Bcl-2 inhibitor, an anti-CD20 mAb and bendamustine.

Further, the present invention relates to a combination product comprising or consisting of a Bcl-2 inhibitor and CHOP (cyclophosphamide, doxorubicin, vincristine and prednisone).

In some embodiments, the Bcl-2 inhibitor is a compound of Formula I-A, or a pharmaceutically acceptable salt or solvate thereof:

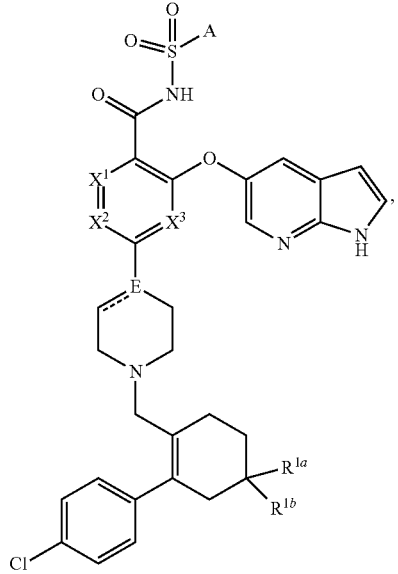

I-A wherein:
A is

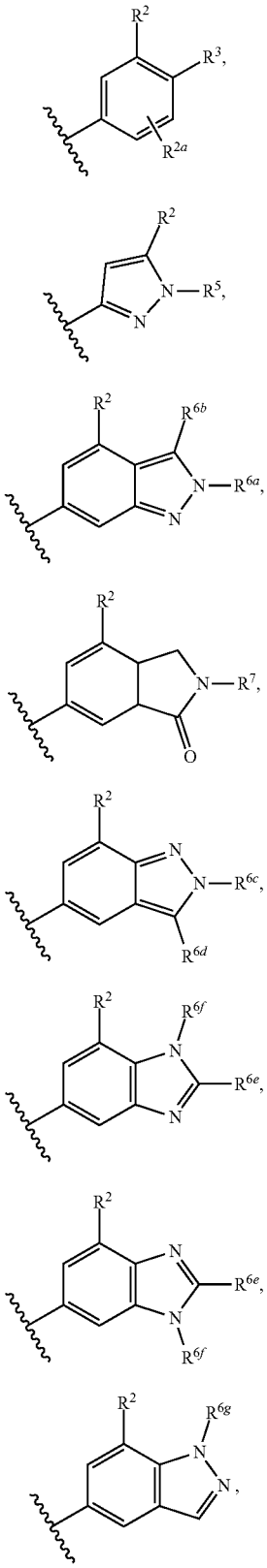
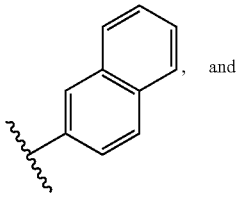

E is a carbon atom and ═══ is a double bond; or
E is a —C(H)— and ═══ is a single bond; or
E is a nitrogen atom and ═══ is a single bond;
X1, X2 and X3 are each independently selected from the group consisting of —CR8═ and —N═;
R1a and R1b taken together with the carbon atom to which they are attached form a 3-, 4-, or 5-membered optionally substituted aliphatic ring; or
R1a and R1b taken together with the carbon atom to which they are attached form a 4- or 5-membered optionally substituted heterocyclo;
R2 is selected from the group consisting of —NO2, —SO2CH3, and —SO2CF3;
R2a is selected from the group consisting of hydrogen and X;
R3 is selected from the group consisting of hydrogen, —CN, —C≡CH, and —N(R4a)(R4b);
R4a is selected from the group consisting of optionally substituted C1-6 alkyl, optionally substituted C3-6 cycloalkyl, heterocyclo, heteroalkyl, cycloalkylalkyl, and heterocycloalkyl;
R4b is selected from the group consisting of hydrogen and C14 alkyl;
R5 is selected from the group consisting of is selected from the group consisting of optionally substituted C1-6 alkyl, heterocyclo, cycloalkylalkyl, and heterocycloalkyl;
R6a, R6c, R6e, R6f, and R6g are each independently selected from the group consisting of hydrogen, optionally substituted C1-6 alkyl, optionally substituted C3-6 cycloalkyl, optionally substituted aryl, optionally substituted heteroaryl, heterocyclo, heteroalkyl, cycloalkylalkyl, and heterocycloalkyl;
R6b and R6d are each independently selected from the group consisting of hydrogen, C1-4 alkyl, and halogen;
R7 is selected from the group consisting of optionally substituted C1-6 alkyl, heterocyclo, heteroalkyl, cycloalkylalkyl, and heterocycloalkyl; and
R8 is selected from the group consisting of hydrogen and halogen.

In the above compound of Formula I-A, the "X" in the definition of variant R2a refers to halogen. Further, halogen mentioned above refers to F, Cl, Br, or I.

In some embodiments, the Bcl-2 inhibitor is a compound of Formula I-A, wherein: A is selected from the group consisting of A-1, A-2, A-3, A-4, A-5, A-6, A-7, A-8, and A-9; R4a is selected from the group consisting of optionally substituted C1-6 alkyl, heterocyclo, heteroalkyl, cycloalkylalkyl, and heterocycloalkyl; and R6a, R6c, R6e, R6f and R6g are each independently selected from the group consisting of hydrogen, optionally substituted C1-6 alkyl, heterocyclo, heteroalkyl, cycloalkylalkyl, and heterocycloalkyl.

In some embodiments, the Bcl-2 inhibitor is a compound of Formula I, or a pharmaceutically acceptable salt or solvate thereof,

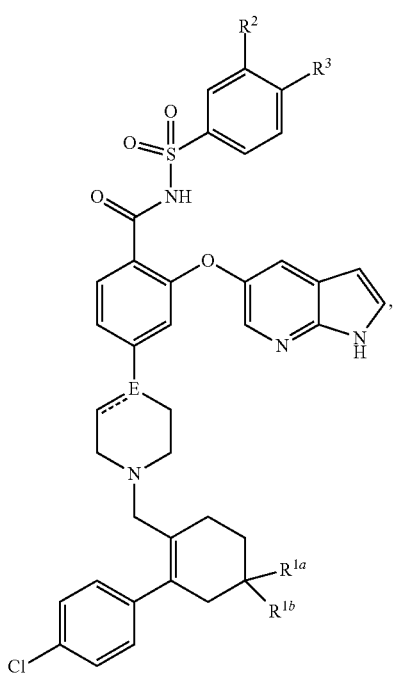

I wherein:

E is a carbon atom and === is a double bond; or E is —C(H)— and === is a single bond; or E is a nitrogen atom and === is a single bond;

R1a and R1b together with the carbon atom connected thereto form a 3-, 4-, or 5-membered optionally substituted aliphatic ring; or R1a and R1b together with the carbon atom connected thereto form a 4- or 5-membered optionally substituted heterocyclo;

R2 is selected from the group consisting of —NO2, —SO2CH3, and —SO2CF3;

R3 is selected from the group consisting of hydrogen, —CN, —C≡CH, and —N(R4a)(R4b);

R4a is selected from the group consisting of optionally substituted C1-6 alkyl, heterocyclo, cycloalkylalkyl, and heterocycloalkyl;

R4b is selected from the group consisting of hydrogen and C14 alkyl.

In some embodiments, the Bcl-2 inhibitor is a compound of Formula II, or a pharmaceutically acceptable salt or solvate thereof,

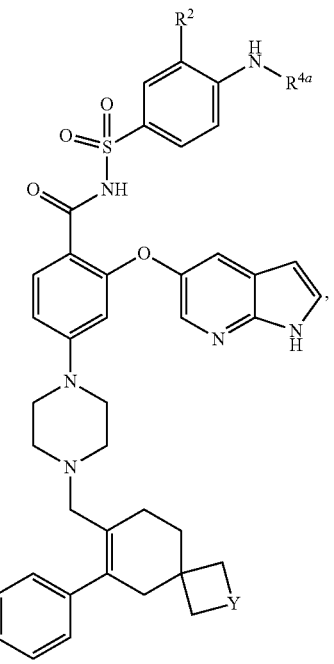

II wherein Y is selected from the group consisting of —CH2— and —O—, and $R^2$ and $R^{4a}$ are as defined in connection with Formula I.

In some embodiments, the Bcl-2 inhibitor is a compound of Formula III, or a pharmaceutically acceptable salt or solvate thereof,

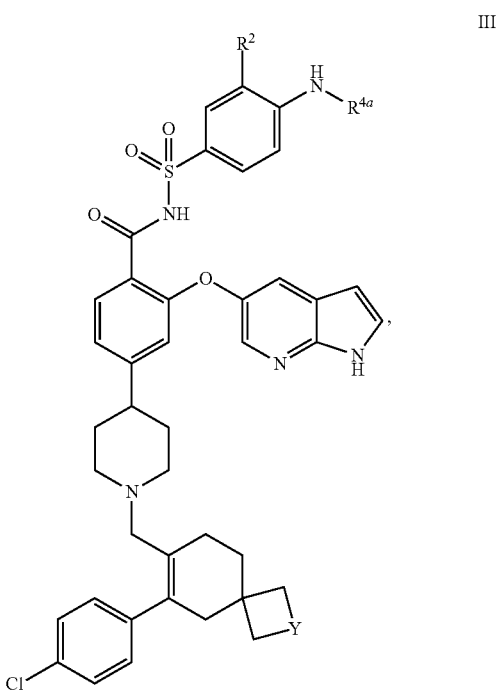

III wherein Y is selected from the group consisting of —CH2— and —O—, and $R^2$ and $R^{4a}$ are as defined in connection with Formula I.

In some embodiments, the Bcl-2 inhibitor is a compound of Formula IV, or a pharmaceutically acceptable salt or solvate thereof,

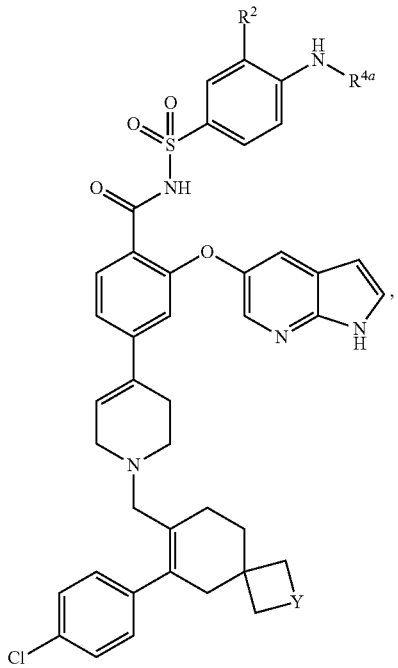

IV wherein Y is selected from the group consisting of —CH$_2$— and —O—, and R$^2$ and R$^{4a}$ are as defined in connection with Formula I.

In some embodiments, the Bcl-2 inhibitor is a compound of Formula V, or a pharmaceutically acceptable salt or solvate thereof,

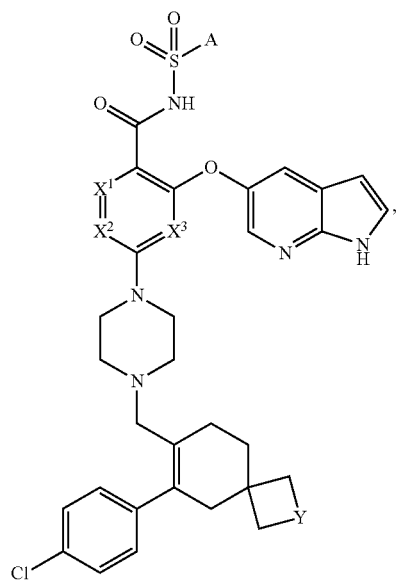

V wherein Y selected from the group consisting of —CH$_2$— and —O—, and A, X$^1$, X$^2$, and X$^3$ are as defined in connection with Formula I-A.

In some embodiments, the Bcl-2 inhibitor is a compound of Formula VI, or a pharmaceutically acceptable salt or solvate thereof,

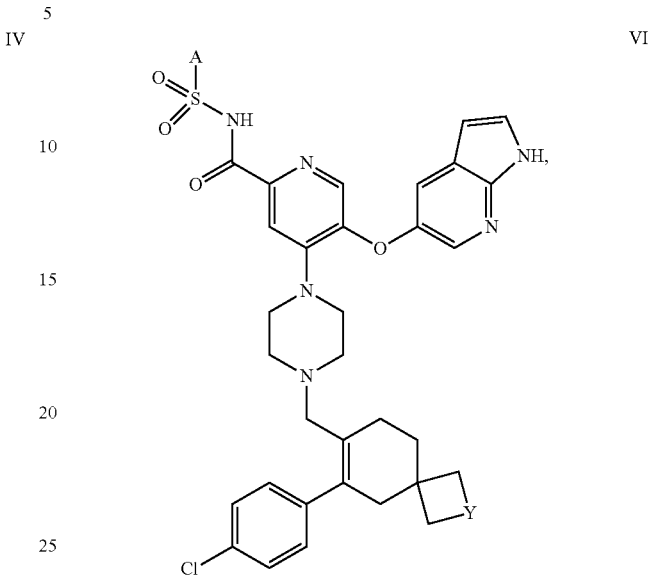

VI wherein Y selected from the group consisting of —CH$_2$— and —O—, and A is as defined in connection with Formula I-A.

In some embodiments, the Bcl-2 inhibitor is a compound of Formula I-A, V or VI, or a pharmaceutically acceptable salt or solvate thereof, wherein A is A-1.

In some embodiments, the Bcl-2 inhibitor is a compound of Formula I-A, V or VI, or a pharmaceutically acceptable salt or solvate thereof, wherein A is A-2.

In some embodiments, the Bcl-2 inhibitor is a compound of Formula I-A, V or VI, or a pharmaceutically acceptable salt or solvate thereof, wherein A is A-3.

In some embodiments, the Bcl-2 inhibitor is a compound of Formula I-A, V or VI, or a pharmaceutically acceptable salt or solvate thereof, wherein A is A-4.

In some embodiments, the Bcl-2 inhibitor is a compound of Formula I-A, V or VI, or a pharmaceutically acceptable salt or solvate thereof, wherein A is A-5.

In some embodiments, the Bcl-2 inhibitor is a compound of Formula I-A, V or VI, or a pharmaceutically acceptable salt or solvate thereof, wherein A is A-6.

In some embodiments, the Bcl-2 inhibitor is a compound of Formula I-A, V or VI, or a pharmaceutically acceptable salt or solvate thereof, wherein A is A-7.

In some embodiments, the Bcl-2 inhibitor is a compound of Formula I-A, V or VI, or a pharmaceutically acceptable salt or solvate thereof, wherein A is A-8.

In some embodiments, the Bcl-2 inhibitor is a compound of Formula I-A, V or VI, or a pharmaceutically acceptable salt or solvate thereof, wherein A is A-9.

In some embodiments, the Bcl-2 inhibitor is a compound of Formula I-A, V or VI, or a pharmaceutically acceptable salt or solvate thereof, wherein A is A-10.

In some embodiments, the Bcl-2 inhibitor is a compound of Formula VII, or a pharmaceutically acceptable salt or solvate thereof,

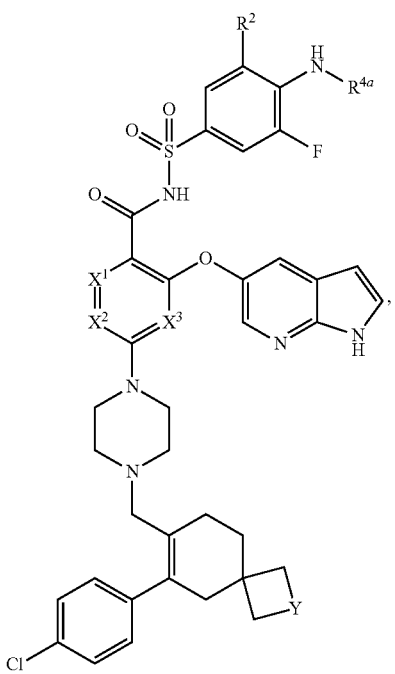

VII wherein Y selected from the group consisting of —CH$_2$— and —O—, and X$^1$, X$^2$, X$^3$, R$^2$, and R$^{4a}$ are as defined in connection with Formula I-A.

In some embodiments, the Bcl-2 inhibitor is a compound of Formula I-A, V or VII, or a pharmaceutically acceptable salt or solvate thereof, wherein all X$^1$, X$^2$, and X$^3$ are —CH=.

In some embodiments, the Bcl-2 inhibitor is a compound of Formula I-A, V or VII, or a pharmaceutically acceptable salt or solvate thereof, wherein X$^1$ is —CF=, and both X$^2$ and X$^3$ are each —CH=.

In some embodiments, the Bcl-2 inhibitor is a compound of Formula I-A, V or VII, or a pharmaceutically acceptable salt or solvate thereof, wherein both X$^1$ and X$^3$ are —CH=, and X$^2$ is —CF=.

In some embodiments, the Bcl-2 inhibitor is a compound of Formula I-A, V or VII, or a pharmaceutically acceptable salt or solvate thereof, wherein both X$^1$ and X$^2$ are —CH=, and X$^3$ is —CF=.

In some embodiments, the Bcl-2 inhibitor is a compound of Formula I-A, V or VII, or a pharmaceutically acceptable salt or solvate thereof, wherein X$^1$ is —N=, and both X$^2$ and X$^3$ are —CH=.

In some embodiments, the Bcl-2 inhibitor is a compound of Formula I-A, V or VII, or a pharmaceutically acceptable salt or solvate thereof, wherein both X$^1$ and X$^3$ are —CH=, and X$^2$ is —N=.

In some embodiments, the Bcl-2 inhibitor is a compound of Formula I-A, V or VII, or a pharmaceutically acceptable salt or solvate thereof, wherein both X$^1$ and X$^2$ are —CH=, and X$^3$ is —N=.

In some embodiments, the Bcl-2 inhibitor is a compound of any one of Formulae II-VII, or a pharmaceutically acceptable salt or solvate thereof, wherein Y is —O—.

In some embodiments, the Bcl-2 inhibitor is a compound of any one of Formulae II-VII, or a pharmaceutically acceptable salt or solvate thereof, wherein Y is —CH$_2$—.

In some embodiments, the Bcl-2 inhibitor is a compound of any one of Formulae I-A or 1-VII, or a pharmaceutically acceptable salt or solvate thereof, wherein R$^2$ is —NO$_2$.

In some embodiments, the Bcl-2 inhibitor is a compound of any one of Formulae I-VI, or a pharmaceutically acceptable salt or solvate thereof, wherein R$^{4a}$ is selected from the group consisting of:

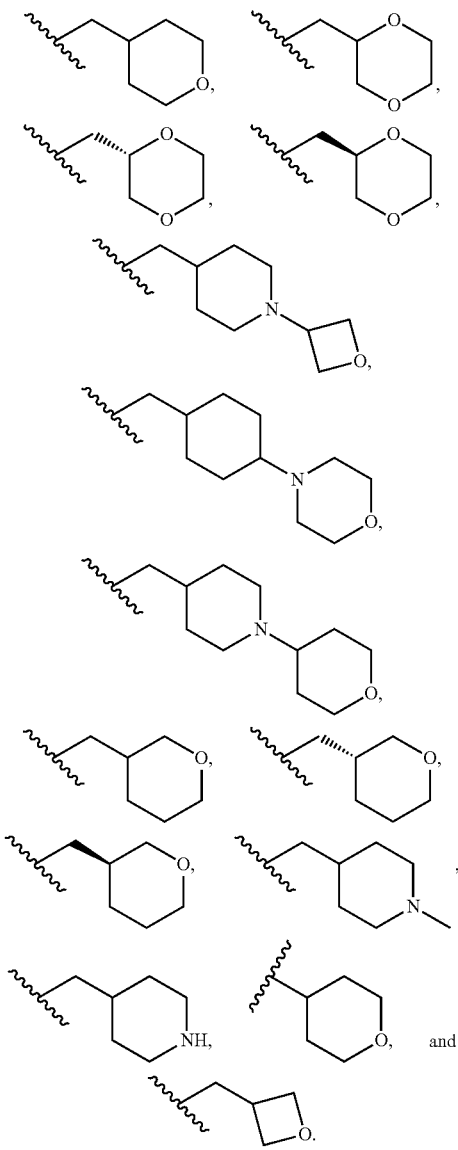

In some embodiments, the Bcl-2 inhibitor is a compound of any one of Formulae I-A or V-VII, or a pharmaceutically acceptable salt or solvate thereof, wherein R$^{4a}$, R$^5$, R$^{6a}$, and R$^7$ are each independently selected from the group consisting of:

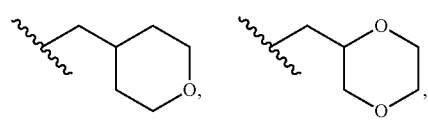

-continued

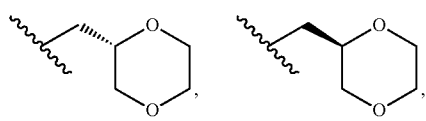

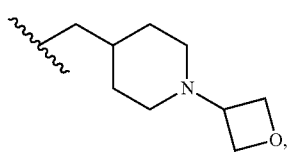

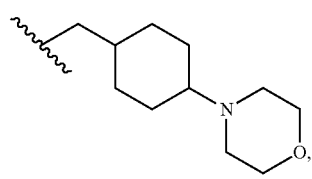

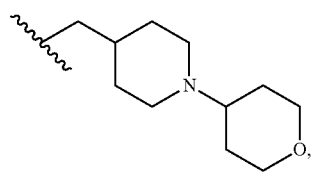

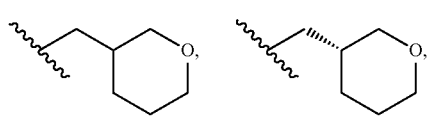

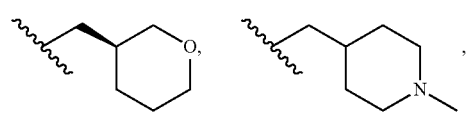

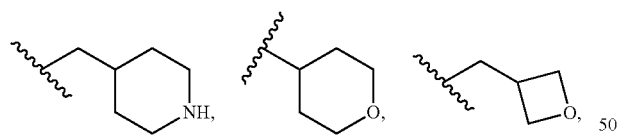

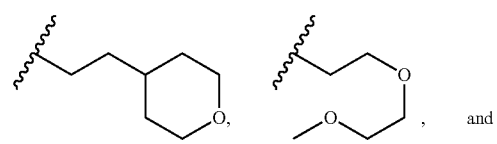, and

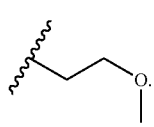

In some embodiments, the Bcl-2 inhibitor is a compound of Formula VIII, or a pharmaceutically acceptable salt or solvate thereof, wherein $R^{2a}$ is hydrogen or fluoro and Re is as defined in connection with Formula I-A.

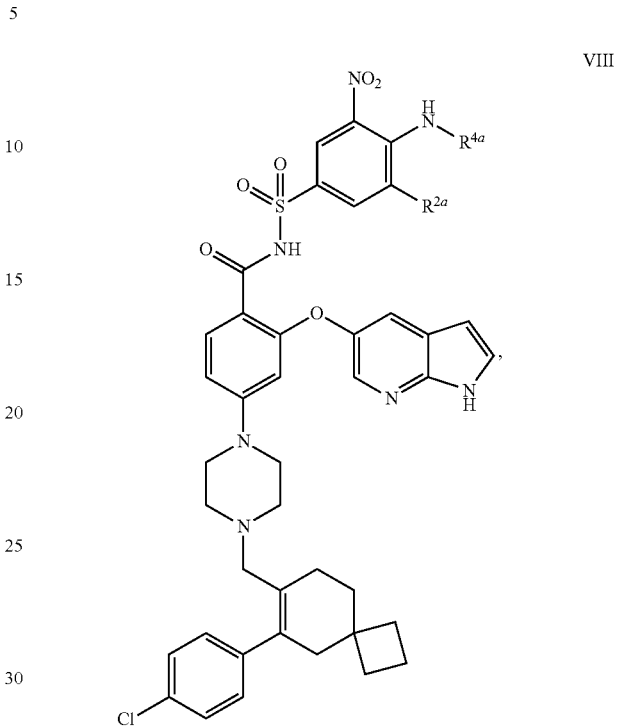

VIII

In some embodiments, the Bcl-2 inhibitor is a compound of Formula VIII, or a pharmaceutically acceptable salt or solvate thereof, wherein $R^{4a}$ is selected from the group consisting of:

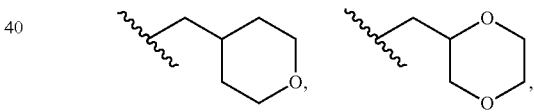

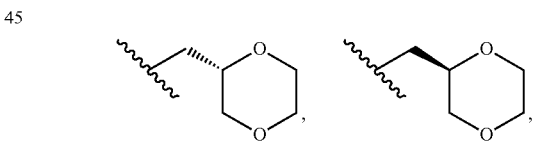

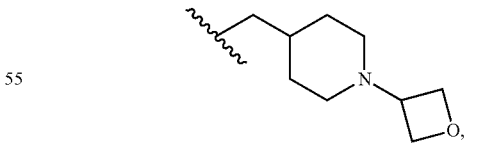

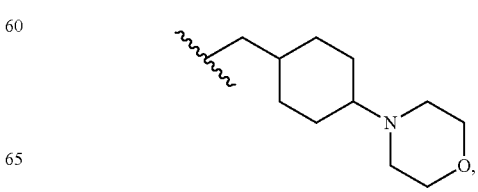

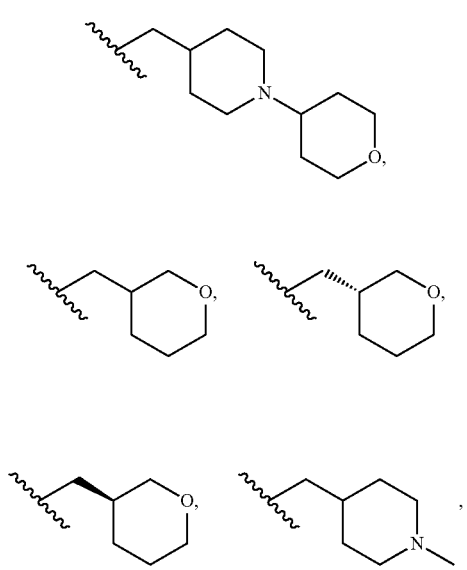
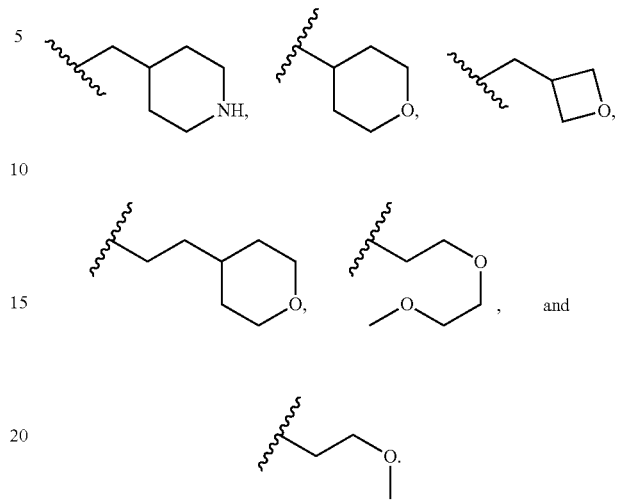
In some embodiments, the Bcl-2 inhibitor is a compound selected from one or more of the compounds of Table 1, or a pharmaceutically acceptable salt or solvate thereof.
TABLE 1
| Cpd. No. | Structure | Name |
| --- | --- | --- |
| 1 | 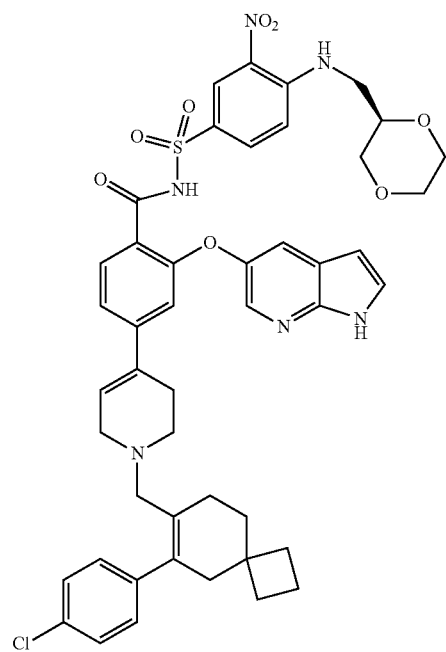 [SMILES: O=C(NS(=O)(=O)c1ccc(NC[C@@H]2COCCO2)c([N+](=O)[O-])c1)c1ccc(C2=CCN(CC3=C(c4ccc(Cl)cc4)CC4(CCC4)CC3)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)benzamide |

TABLE 1-continued

| Cpd. No. | Structure | Name |
|---|---|---|
| 2 | 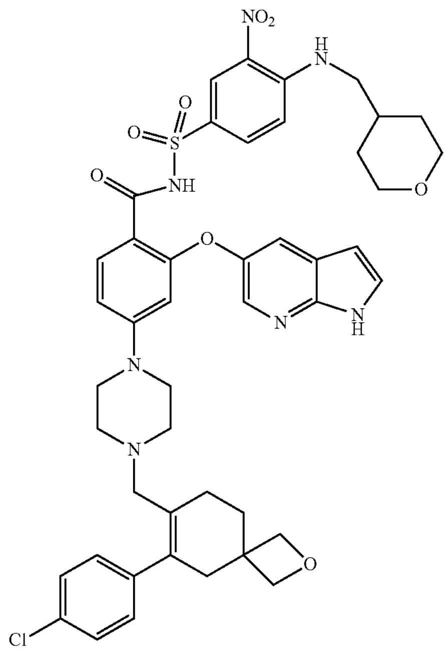 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CC3)COC4)CC2)cc1Oc1cnc2[nH]ccc2c1] | 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)-N-((3-nitro-4-(((tetrahydro-2H-pyran-4-yl)methyl)amino)phenyl)sulfonyl)benzamide |
| 3 | 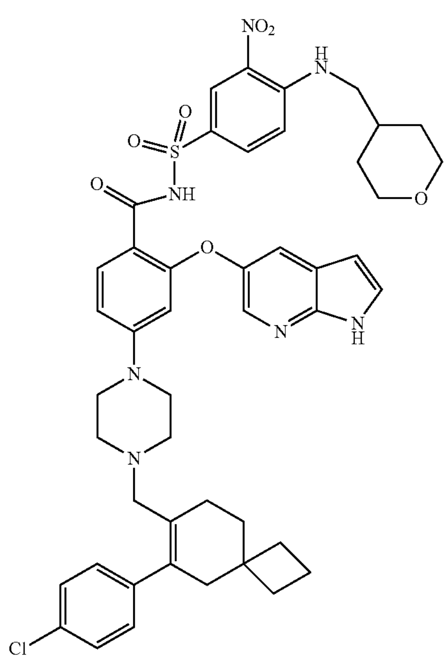 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)benzamide |

| Cpd. No. | Structure | Name |
|---|---|---|
| 4 | 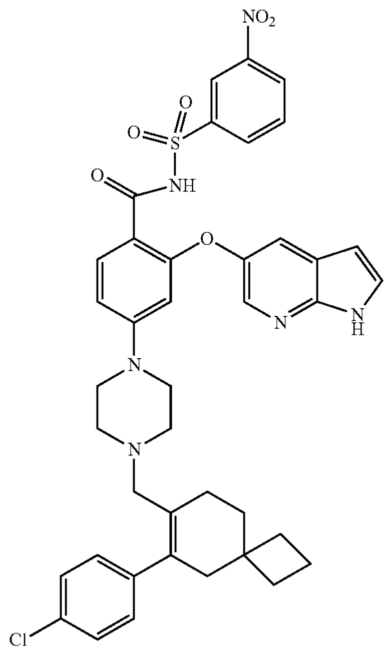 [SMILES: O=C(NS(=O)(=O)c1cccc([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitrophenyl)sulfonyl)benzamide |
| 5 | 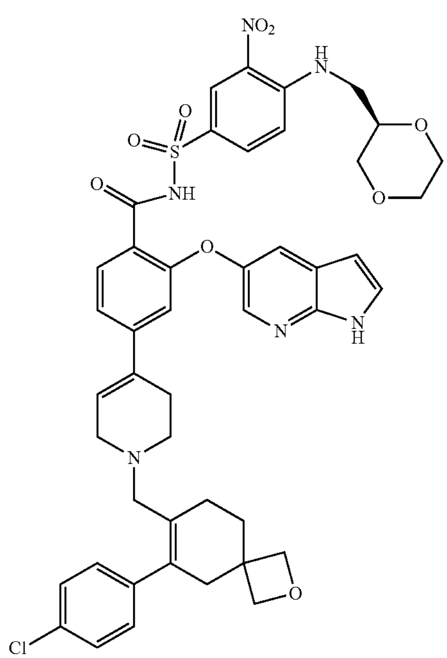 [SMILES: O=C(NS(=O)(=O)c1ccc(NC[C@@H]2COCCO2)c([N+](=O)[O-])c1)c1ccc(C2=CCN(CC3=C(c4ccc(Cl)cc4)CC4(CC3)COC4)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)-2-oxaspiro[3.5]non-6-en-7-yl)methyl)-1,2,3,6-tetrahydropyridin-4-yl)benzamide |

TABLE 1-continued

| Cpd. No. | Structure | Name |
|---|---|---|
| 6 | 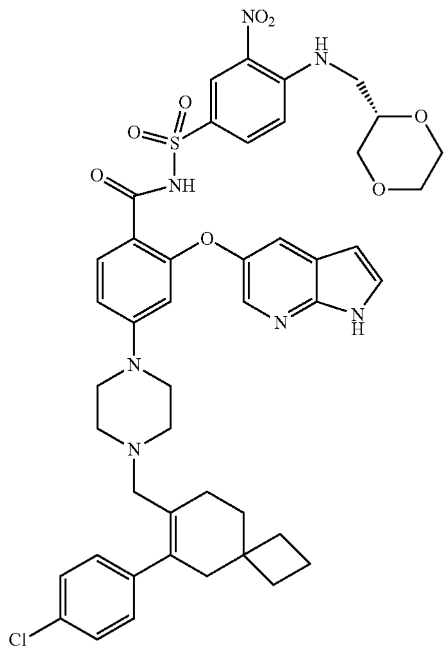 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |
| 7 | 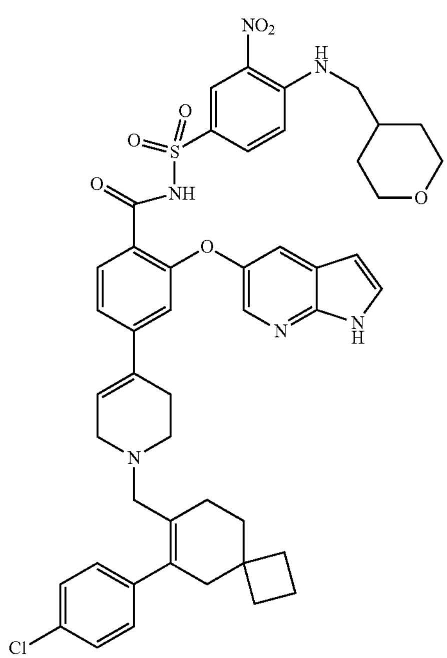 [SMILES: O=C(NS(=O)(=O)c1ccc(NCC2CCOCC2)c([N+](=O)[O-])c1)c1ccc(C2=CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)-N-((3-nitro-4-(((tetrahydro-2H-pyran-4-yl)methyl)amino)phenyl)sulfonyl)benzamide |

TABLE 1-continued

| Cpd. No. | Structure | Name |
|---|---|---|
| 8 | 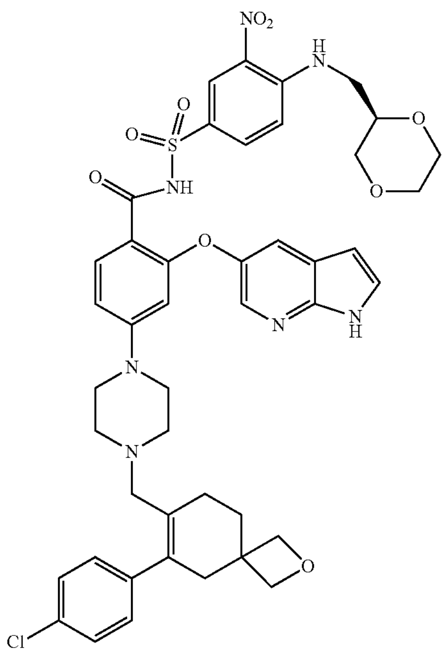 [SMILES: O=C(NS(=O)(=O)c1ccc(NC[C@@H]2COCCO2)c([N+](=O)[O-])c1)c1ccc(N2CCN(CC3=C(c4ccc(Cl)cc4)CC4(CC3)COC4)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzamide |
| 9 | 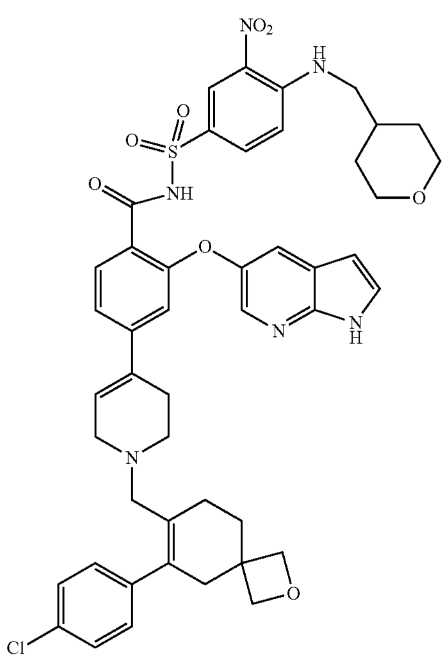 [SMILES: O=C(NS(=O)(=O)c1ccc(NCC2CCOCC2)c([N+](=O)[O-])c1)c1ccc(C2=CCN(CC3=C(c4ccc(Cl)cc4)CC4(CC3)COC4)CC2)cc1Oc1cnc2[nH]ccc2c1] | 2-((1H-pyrrolo[2,3-b]pyridin-5-yl)oxy)-4-(1-((6-(4-chlorophenyl)-2-oxaspiro[3.5]non-6-en-7-yl)methyl)-1,2,3,6-tetrahydropyridin-4-yl)-N-((3-nitro-4-(((tetrahydro-2H-pyran-4-yl)methyl)amino)phenyl)sulfonyl)benzamide |

TABLE 1-continued

| Cpd. No. | Structure | Name |
|---|---|---|
| 10 | 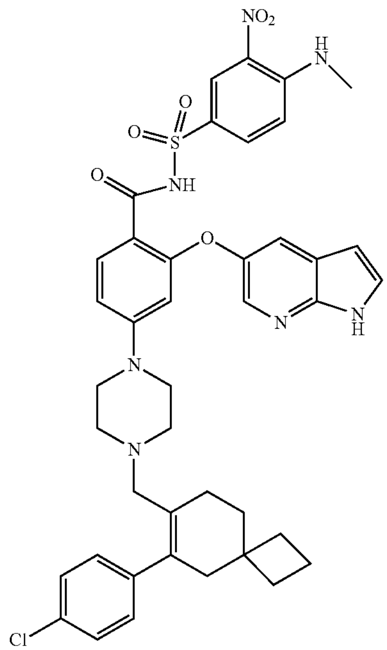 [SMILES: CNc1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(methylamino)-3-nitrophenyl)sulfonyl)benzamide |
| 11 | 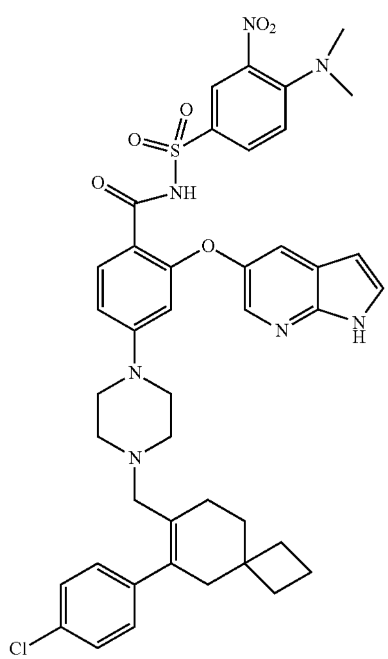 [SMILES: CN(C)c1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(dimethylamino)-3-nitrophenyl)sulfonyl)benzamide |

| Cpd. No. | Structure | Name |
|---|---|---|
| 12 | 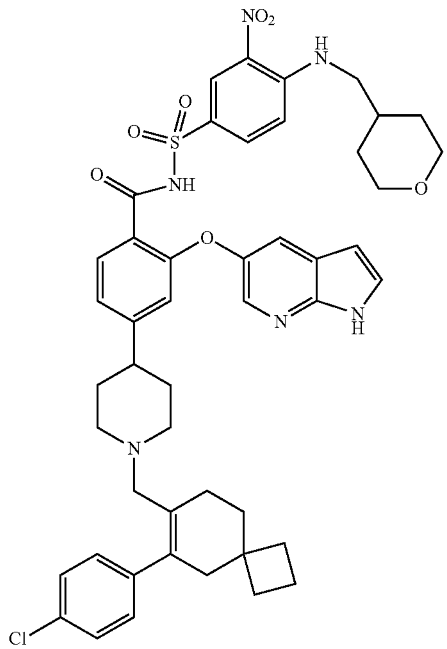 [SMILES: O=C(NS(=O)(=O)c1ccc(NCC2CCOCC2)c([N+](=O)[O-])c1)c1ccc(C2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(1-((6-(4-chlorophenyl)spiro[3.5]non-6-en-7-yl)methyl)piperidin-4-yl)-N-((3-nitro-4-(((tetrahydro-2H-pyran-4-yl)methyl)amino)phenyl)sulfonyl)benzamide |
| 13 | 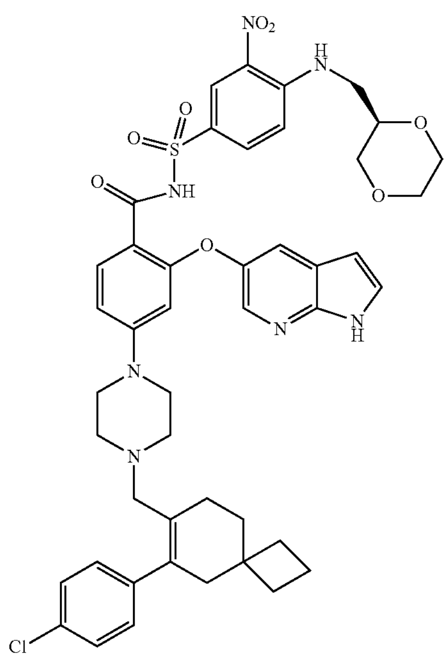 [SMILES: O=C(NS(=O)(=O)c1ccc(NC[C@@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |

TABLE 1-continued

| Cpd. No. | Structure | Name |
|---|---|---|
| 14 | 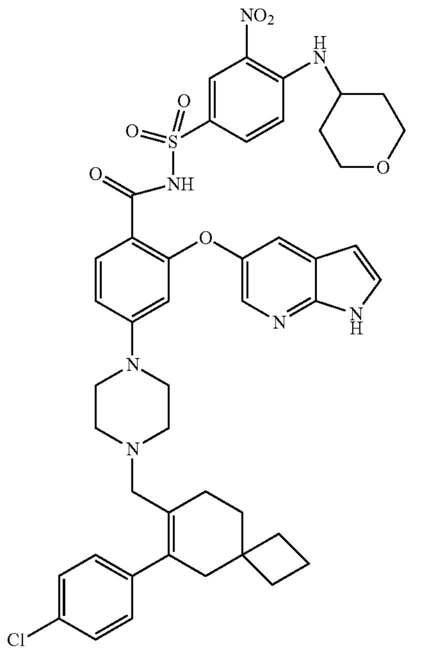 [SMILES: O=C(NS(=O)(=O)c1ccc(NC2CCOCC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((tetrahydro-2H-pyran-4-yl)amino)phenyl)sulfonyl)benzamide |
| 15 | 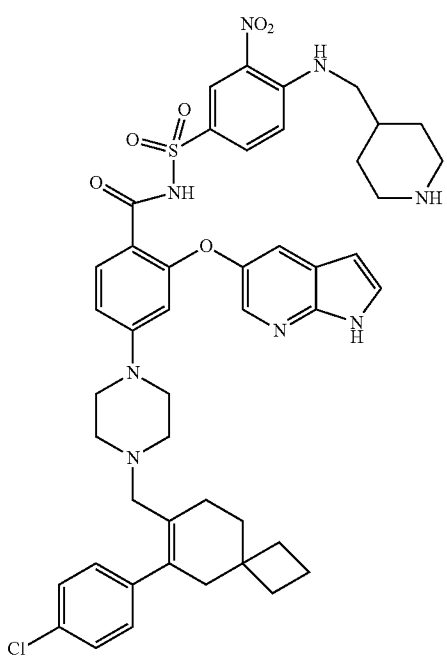 [SMILES: O=C(NS(=O)(=O)c1ccc(NCC2CCNCC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((piperidin-4-ylmethyl)amino)phenyl)sulfonyl)benzamide |

TABLE 1-continued

| Cpd. No. | Structure | Name |
|---|---|---|
| 16 | 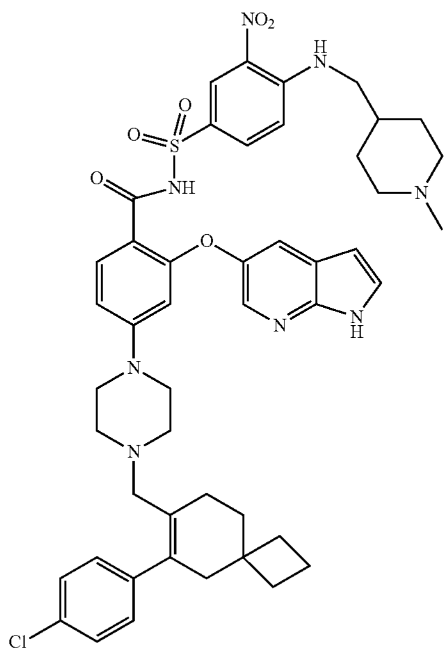 [SMILES: CN1CCC(CNc2ccc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc2[N+](=O)[O-])CC1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(((1-methylpiperidin-4-yl)methyl)amino)-3-nitrophenyl)sulfonyl)benzamide |
| 17 | 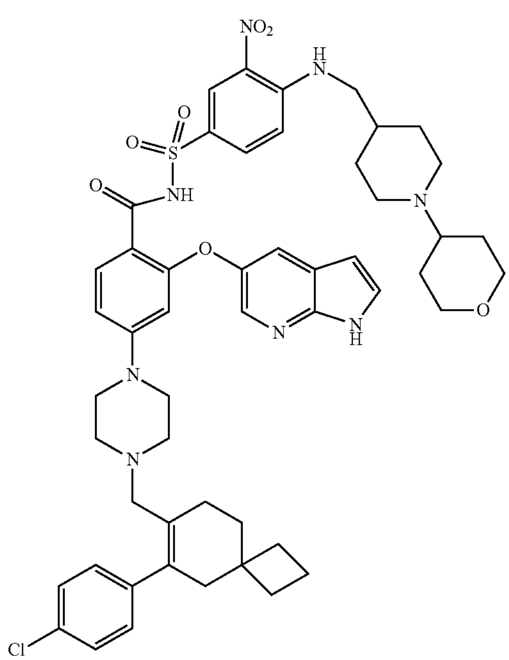 [SMILES: O=C(NS(=O)(=O)c1ccc(NCC2CCN(C3CCOCC3)CC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((1-(tetrahydro-2H-pyran-4-yl)piperidin-4-yl)methyl)amino)phenyl)sulfonyl)benzamide |

TABLE 1-continued

| Cpd. No. | Structure | Name |
|---|---|---|
| 18 | 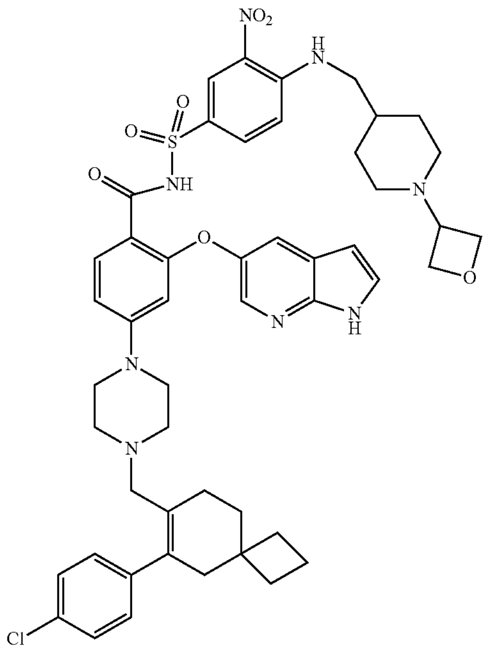 [SMILES: O=C(NS(=O)(=O)c1ccc(NCC2CCN(C3COC3)CC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((1-(oxetan-3-yl)piperidin-4-yl)methyl)amino)phenyl)sulfonyl)benzamide |
| 19 | 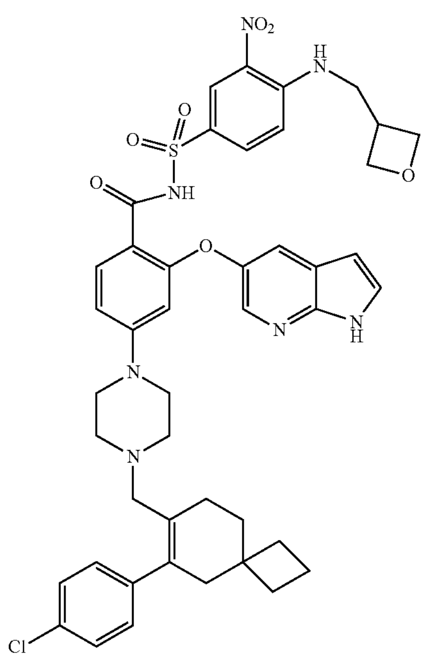 [SMILES: O=C(NS(=O)(=O)c1ccc(NCC2COC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((oxetan-3-ylmethyl)amino)phenyl)sulfonyl)benzamide |

TABLE 1-continued

| Cpd. No. | Structure | Name |
|---|---|---|
| 20 | 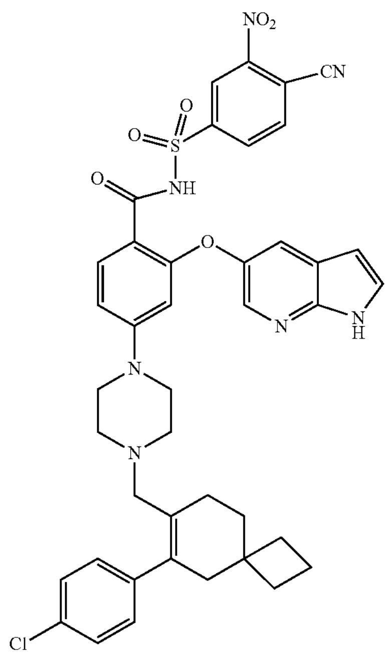 [SMILES: N#Cc1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-cyano-3-nitrophenyl)sulfonyl)benzamide |
| 21 | 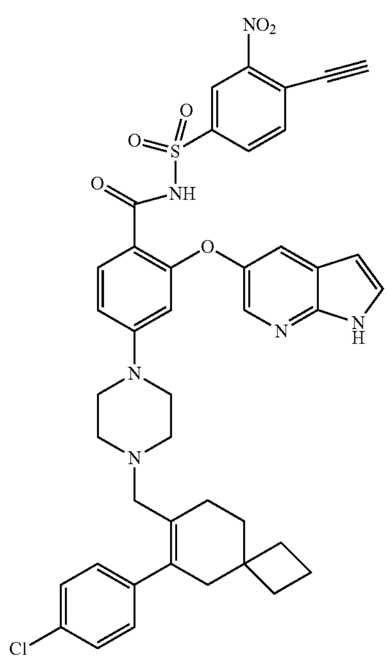 [SMILES: C#Cc1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-ethynyl-3-nitrophenyl)sulfonyl)benzamide |

In some embodiments, the Bcl-2 inhibitor is a compound selected from one or more of the compounds of Table 1-A, or a pharmaceutically acceptable salt or solvate thereof.

TABLE 1-A

| Cpd. No. | Structure | Name |
|---|---|---|
| 22 | 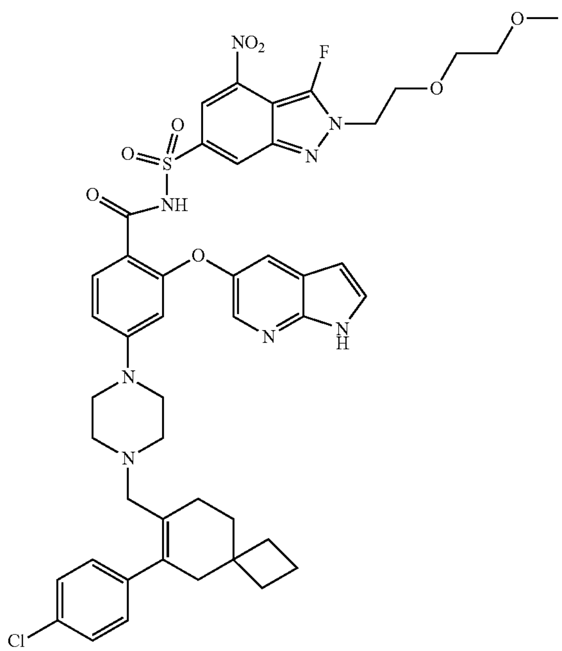 [SMILES: COCCOCCn1nc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2c1F] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-fluoro-2-(2-(2-methoxyethoxy)ethyl)-4-nitro-2H-indazol-6-yl)sulfonyl)benzamide |
| 23 | 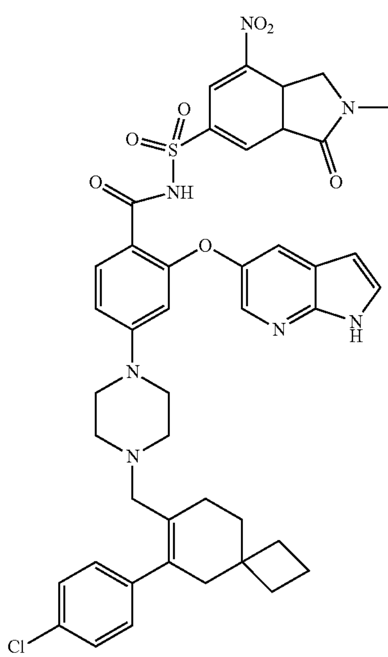 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-3-oxo-2-(tetrahydro-2H-pyran-4-yl)-2,3,3a,7a-tetrahydro-1H-isoindol-5-yl)sulfonyl)benzamide |

TABLE 1-A-continued

| Cpd. No. | Structure | Name |
|---|---|---|
| 24 | 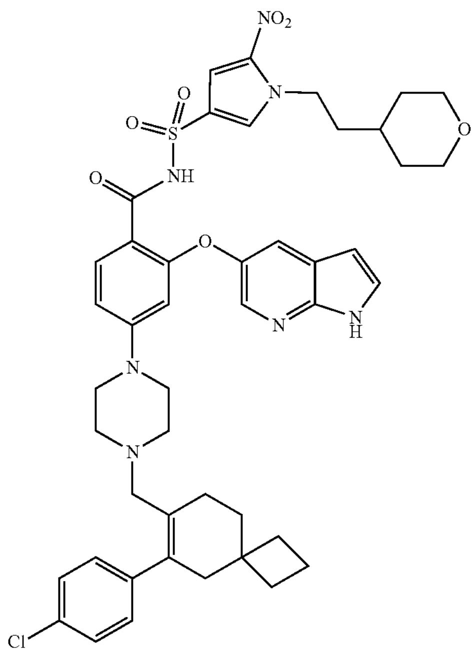 [SMILES: O=C(NS(=O)(=O)c1cc([N+](=O)[O-])n(CCC2CCOCC2)c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((5-nitro-1-(2-tetrahydro-2H-pyran-4-yl)ethyl)-1H-pyrrol-3-yl)sulfonyl)benzamide |
| 25 | 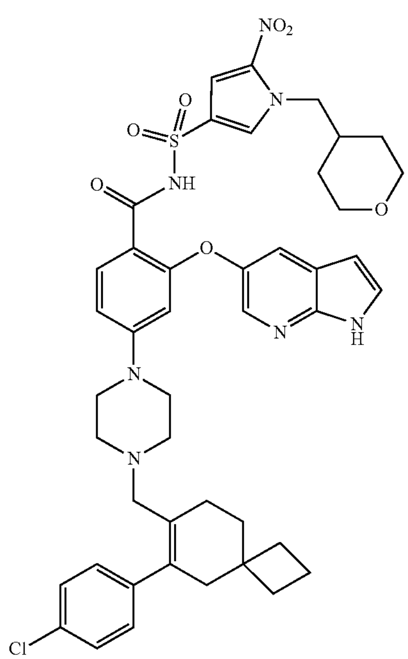 [SMILES: O=C(NS(=O)(=O)c1cc([N+](=O)[O-])n(CC2CCOCC2)c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((5-nitro-1-((tetrahydro-2H-pyran-4-yl)methyl)-1H-pyrrol-3-yl)sulfonyl)benzamide |

TABLE 1-A-continued
| Cpd. No. | Structure | Name |
|---|---|---|
| 26 | 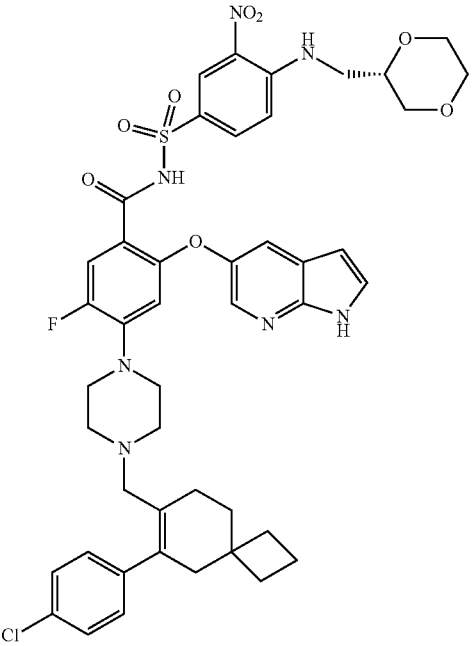 [SMILES: O=C(NS(=O)(=O)c1ccc(NC[C@H]2COCCO2)c([N+](=O)[O-])c1)c1cc(F)c(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)-5-fluorobenzamide |
| 27 | 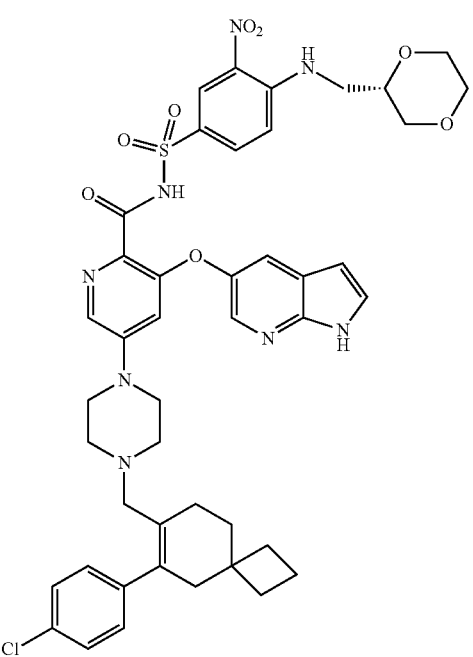 [SMILES: O=C(NS(=O)(=O)c1ccc(NC[C@H]2COCCO2)c([N+](=O)[O-])c1)c1ncc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-3-((1H-pyrrolo[2,3-b]pyridin-5-yl)oxy)-5-(4-((6-(4-chlorophenyl)spiro[3.5]non-6-en-7-yl)methyl)piperazin-1-yl)picolinamide |

TABLE 1-A-continued

| Cpd. No. | Structure | Name |
|---|---|---|
| 28 | 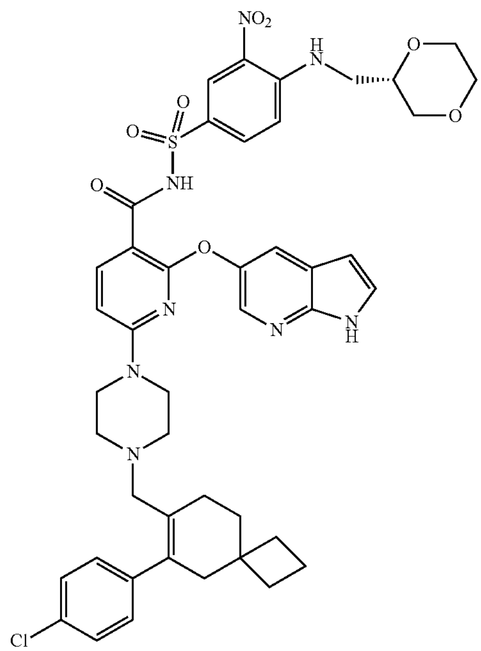 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)nc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-6-(4-((6-(4-chlorophenyl)spiro[3.5]non-6-en-7-yl)methyl)piperazin-1-yl)nicotinamide |
| 29 | 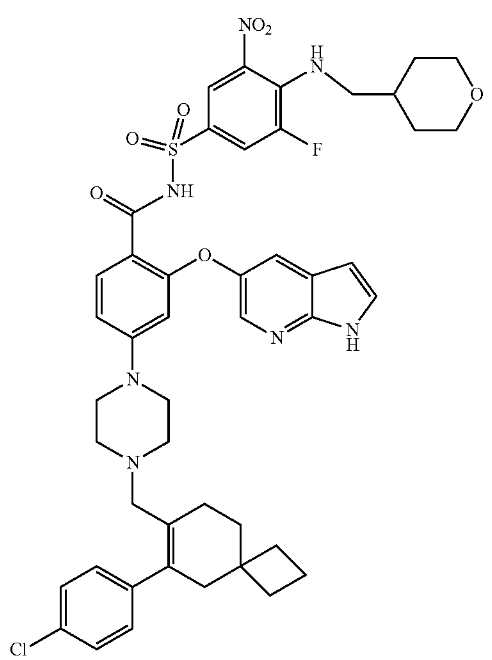 [SMILES: O=C(NS(=O)(=O)c1cc(F)c(NCC2CCOCC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-fluoro-5-nitro-4-(((tetrahydro-2H-pyran-4-yl)methyl)amino)phenyl)sulfonyl)benzamide |

TABLE 1-A-continued
| Cpd. No. | Structure | Name |
| --- | --- | --- |
| 30 | 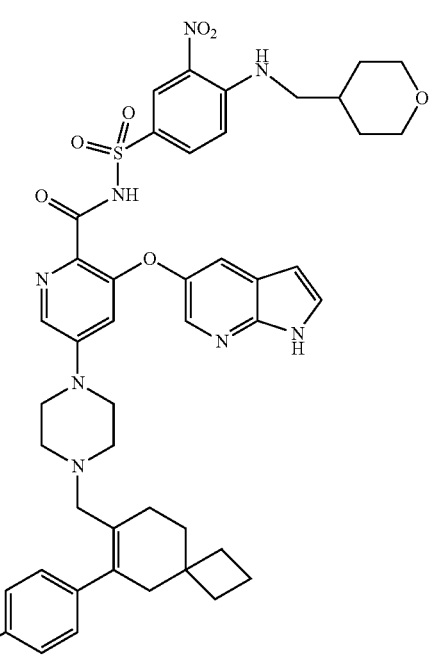 | 3-((1H-pyrrolo[2,3-b]pyridin-5-yl)oxy)-5-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)picolinamide |
| 31 | 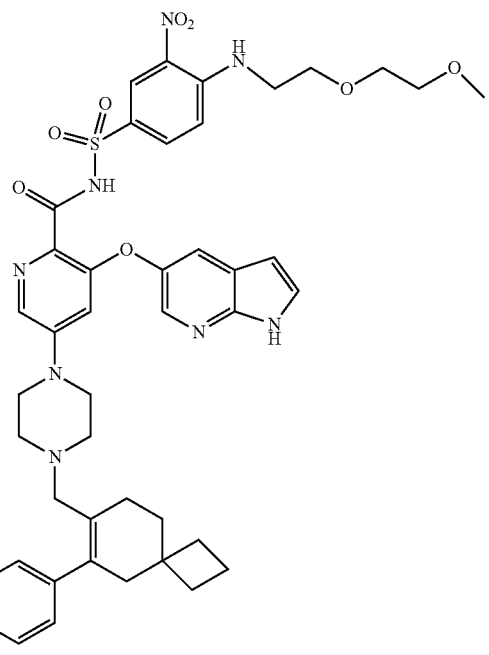 | 3-((1H-pyrrolo[2,3-b]pyridin-5-yl)oxy)-5-(4-((6-(4-chlorophenyl)spiro[3.5]non-6-en-7-yl)methyl)piperazin-1-yl)-N-((4-((2-(2-methoxyethoxy)ethyl)amino)-3-nitrophenyl)sulfonyl)picolinamide |

TABLE 1-A-continued

| Cpd. No. | Structure | Name |
|---|---|---|
| 32 | 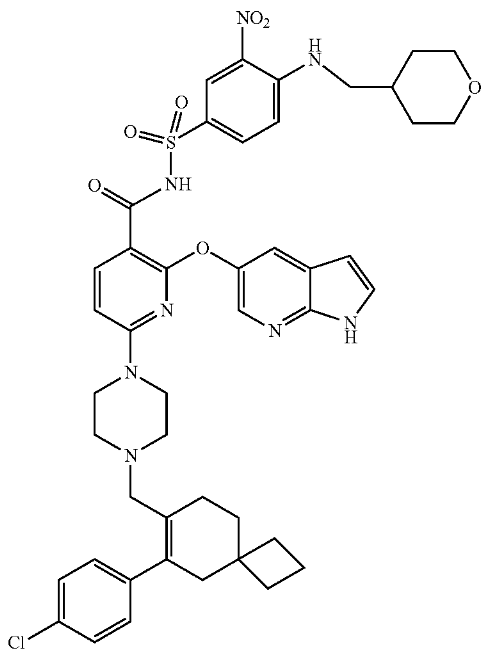 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)nc1Oc1cnc2[nH]ccc2c1] | 2-((1H-pyrrolo[2,3-b]pyridin-5-yl)oxy)-6-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)nicotinamide |
| 33 | 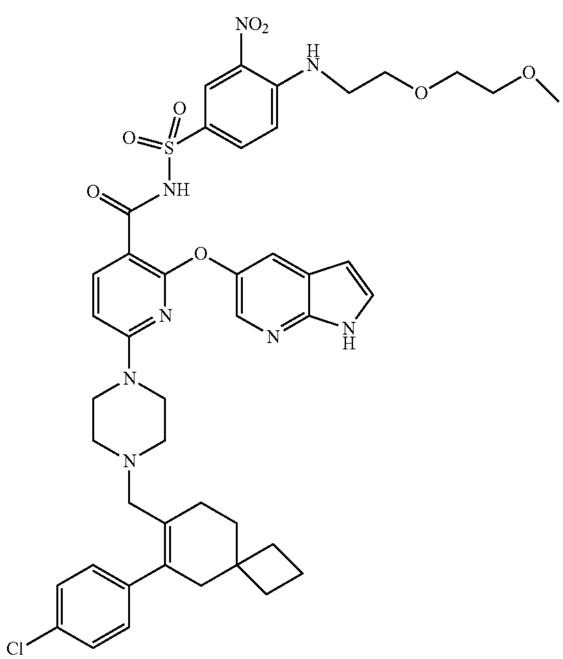 [SMILES: COCCOCCNc1ccc(S(=O)(=O)NC(=O)c2ccc(N3CCN(CC4=C(c5ccc(Cl)cc5)CC5(CCC5)CC4)CC3)nc2Oc2cnc3[nH]ccc3c2)cc1[N+](=O)[O-]] | 2-((1H-pyrrolo[2,3-b]pyridin-5-yl)oxy)-6-(4-((6-(4-chlorophenyl)spiro[3.5]non-6-en-7-yl)methyl)piperazin-1-yl)-N-((4-((2-(2-methoxyethoxy)ethyl)amino)-3-nitrophenyl)sulfonyl)nicotinamide |

TABLE 1-A-continued
| Cpd. No. | Structure | Name |
|---|---|---|
| 34 | 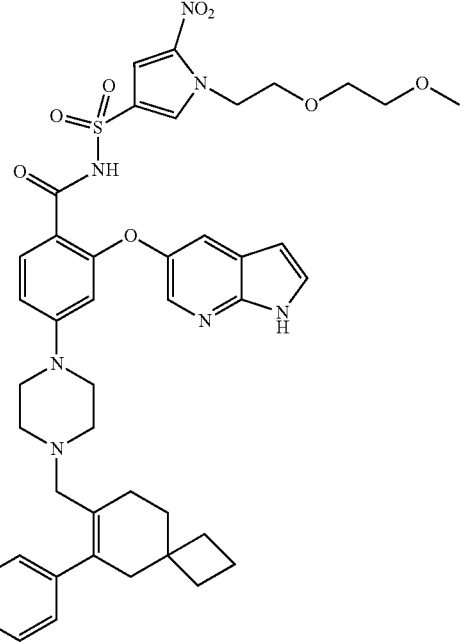 | 3-((1H-pyrrolo[2,3-b]pyridin-5-yl)oxy)-5-(4-((6-(4-chlorophenyl)spiro[3.5]non-6-en-7-yl)methyl)piperazin-1-yl)-N-((4-((2-(2-methoxyethoxy)ethyl)amino)-3-nitrophenyl)sulfonyl)picolinamide |
| 35 | 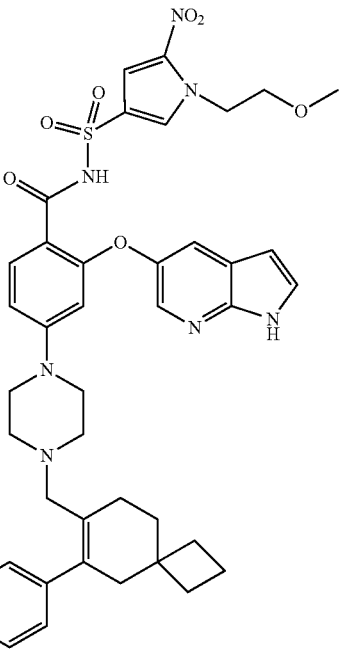 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-(2-methoxyethyl)-5-nitro-1H-pyrrol-3-yl)sulfonyl)benzamide |

TABLE 1-A-continued

| Cpd. No. | Structure | Name |
|---|---|---|
| 36 | 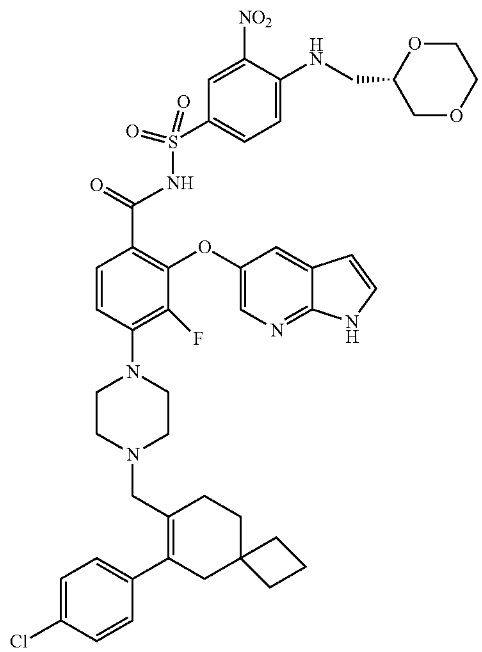 | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluorobenzamide |
| 37 | 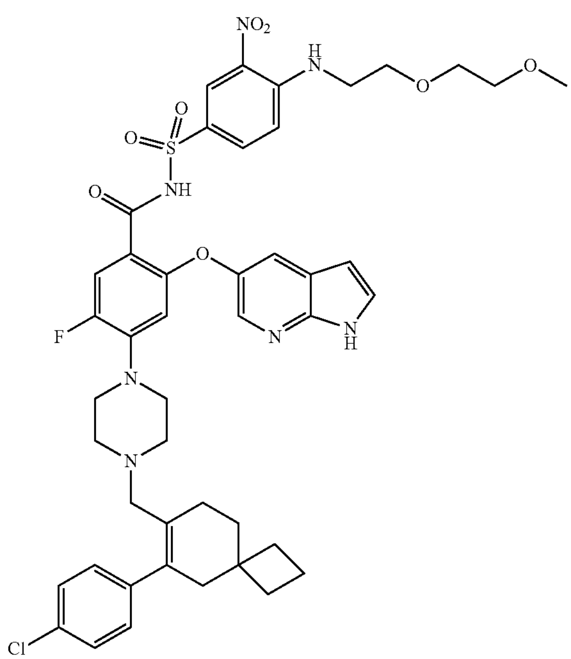 [SMILES: COCCOCCNc1ccc(S(=O)(=O)NC(=O)c2cc(F)c(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-5-fluoro-N-((4-((2-(2-methoxyethoxy)ethyl)amino)-3-nitrophenyl)sulfonyl)benzamide |

TABLE 1-A-continued
| Cpd. No. | Structure | Name |
|---|---|---|
| 38 | 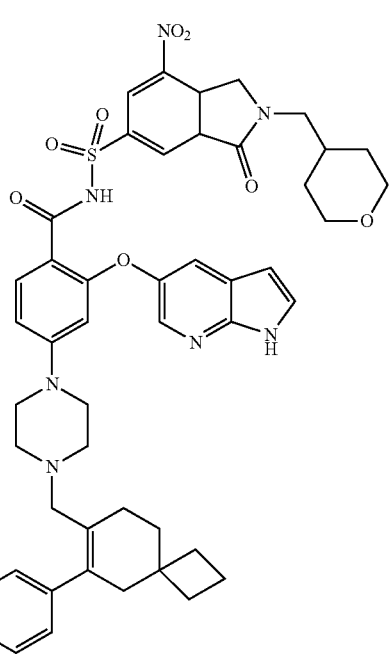 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-3-oxo-2-((tetrahydro-2H-pyran-4-yl)methyl)-2,3,3a,7a-tetrahydro-1H-isoindol-5-yl)sulfonyl)benzamide |
| 39 | 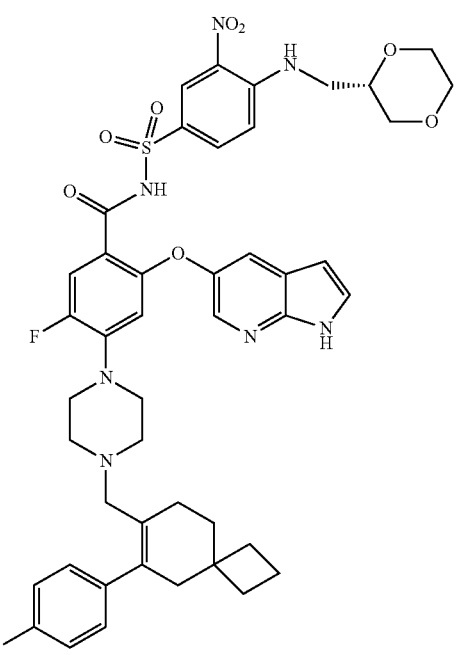 | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)-5-fluorobenzamide |

TABLE 1-A-continued

| Cpd. No. | Structure | Name |
|---|---|---|
| 40 | 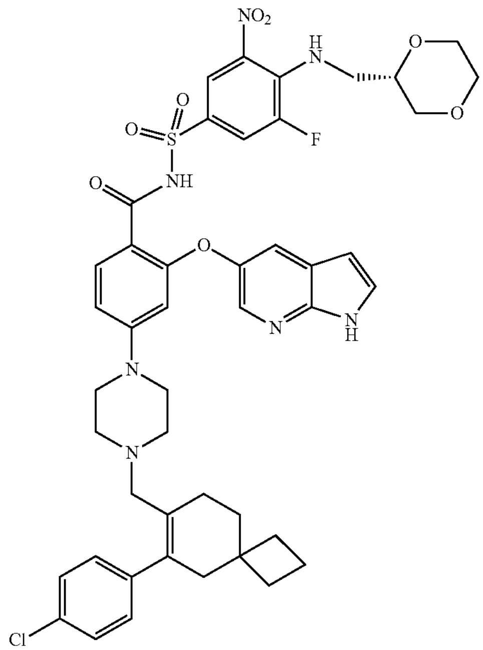 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-fluoro-5-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |
| 41 | 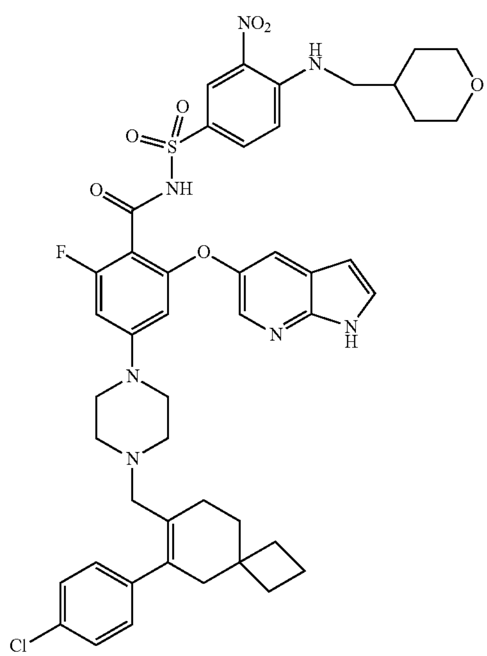 [SMILES: O=C(NS(=O)(=O)c1ccc(NCC2CCOCC2)c([N+](=O)[O-])c1)c1c(F)cc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-6-fluoro-N-((3-nitro-4-(((tetrahydro-2H-pyran-4-yl)methyl)amino)phenyl)sulfonyl)benzamide |

TABLE 1-A-continued

| Cpd. No. | Structure | Name |
|---|---|---|
| 42 | 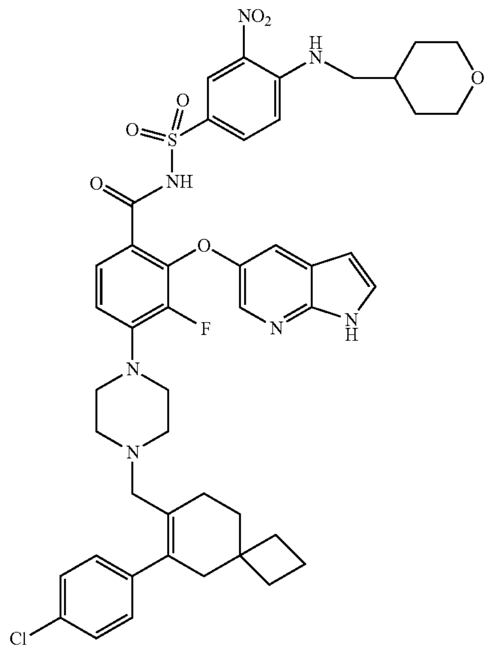 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)c(F)c1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluoro-N-((3-nitro-4-(((tetrahydro-2H-pyran-4-yl)methyl)amino)phenyl)sulfonyl)benzamide |
| 43 | 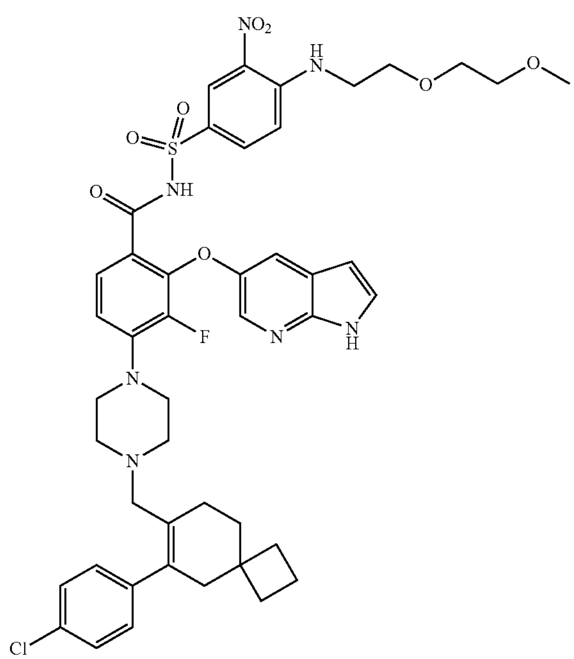 [SMILES: COCCOCCNc1ccc(S(=O)(=O)NC(=O)c2ccc(N3CCN(CC4=C(c5ccc(Cl)cc5)CC5(CCC5)CC4)CC3)c(F)c2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluoro-N-((4-((2-(2-methoxyethoxy)ethyl)amino)-3-nitrophenyl)sulfonyl)benzamide |

TABLE 1-A-continued

| Cpd. No. | Structure | Name |
|---|---|---|
| 44 | 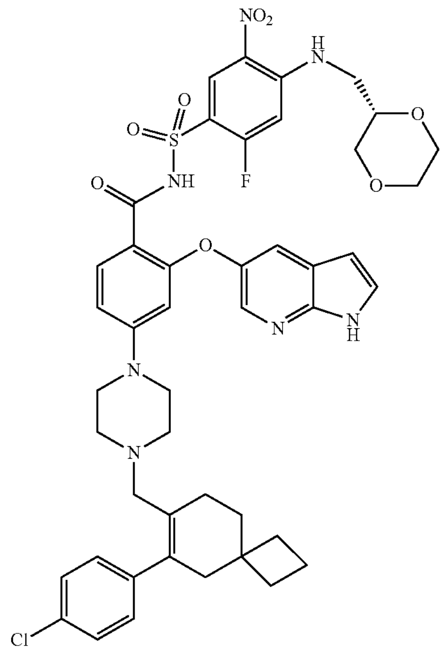 [SMILES: O=C(NS(=O)(=O)c1cc([N+](=O)[O-])c(NC[C@H]2COCCO2)cc1F)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-2-fluoro-5-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |
| 45 | 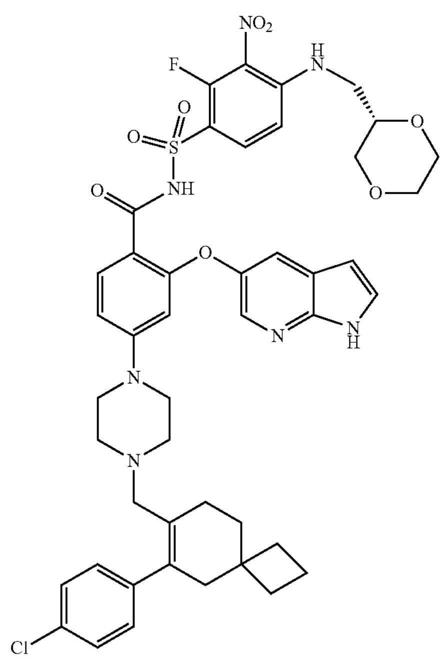 [SMILES: O=C(NS(=O)(=O)c1ccc(NC[C@H]2COCCO2)c([N+](=O)[O-])c1F)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-2-fluoro-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |

TABLE 1-A-continued

| Cpd. No. | Structure | Name |
|---|---|---|
| 46 | 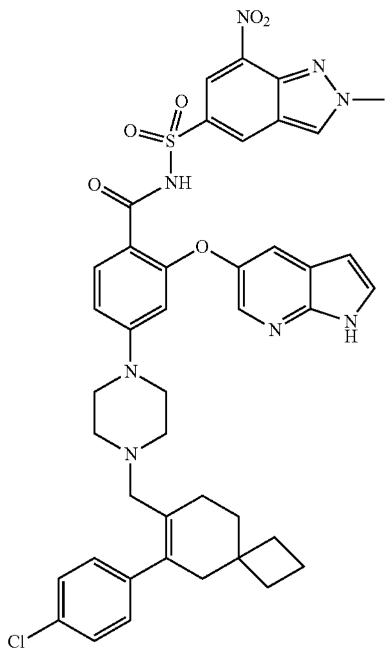 [SMILES: Cn1cc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2n1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-methyl-7-nitro-2H-indazol-5-yl)sulfonyl)benzamide |
| 47 | 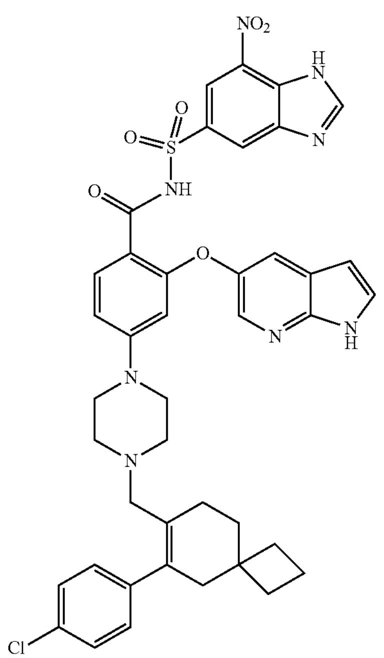 [SMILES: O=C(NS(=O)(=O)c1cc([N+](=O)[O-])c2[nH]cnc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-1H-benzo[d]imidazol-5-yl)sulfonyl)benzamide |

TABLE 1-A-continued
| Cpd. No. | Structure | Name |
|---|---|---|
| 48 | 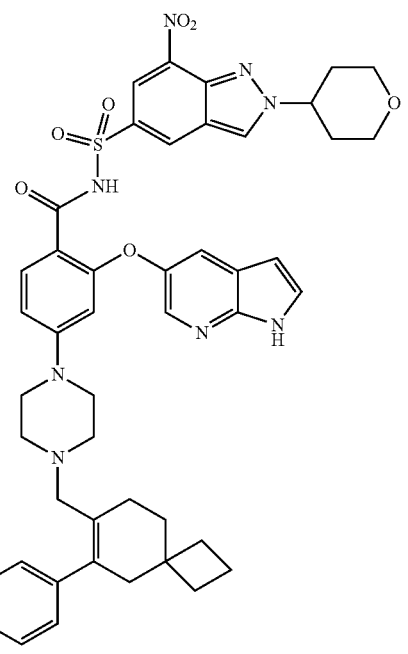 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-(tetrahydro-2H-pyran-4-yl)-2H-indazol-5-yl)sulfonyl)benzamide |
| 49 | 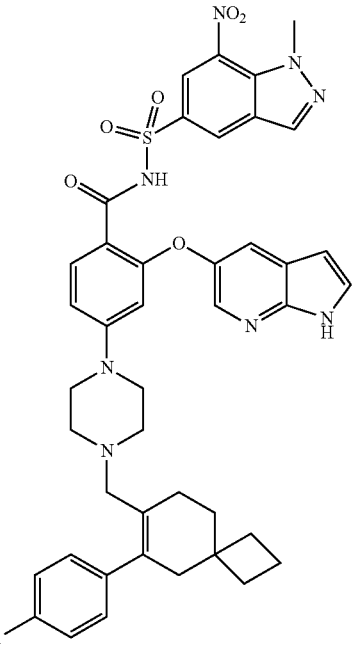 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-methyl-7-nitro-1H-indazol-5-yl)sulfonyl)benzamide |

TABLE 1-A-continued

| Cpd. No. | Structure | Name |
|---|---|---|
| 50 | 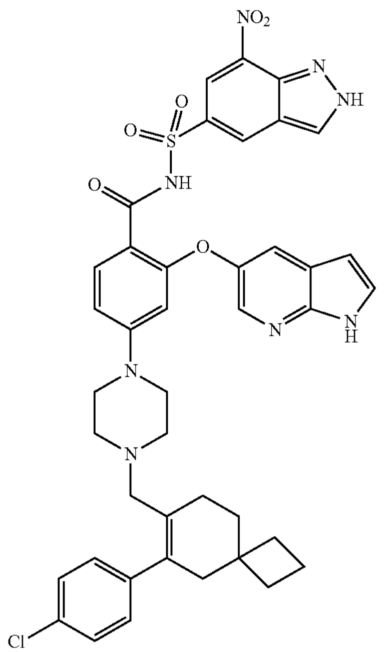 [SMILES: O=C(NS(=O)(=O)c1cc([N+](=O)[O-])c2n[nH]cc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2H-indazol-5-yl)sulfonyl)benzamide |
| 51 | 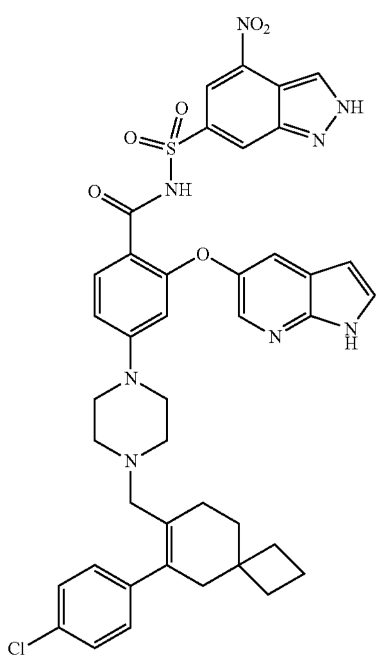 [SMILES: O=C(NS(=O)(=O)c1cc([N+](=O)[O-])c2c[nH]nc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-nitro-2H-indazol-6-yl)sulfonyl)benzamide |

TABLE 1-A-continued

| Cpd. No. | Structure | Name |
|---|---|---|
| 52 | 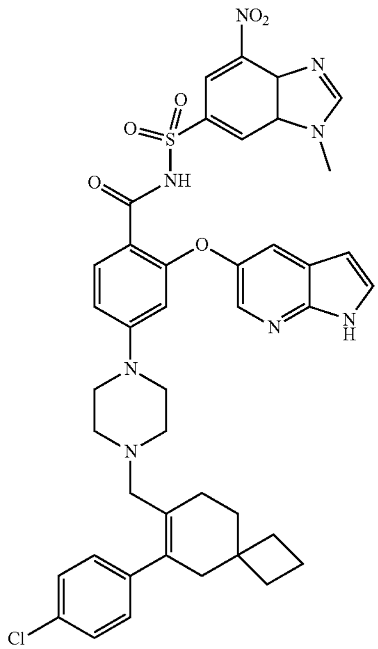 [SMILES: CN1C=NC2C([N+](=O)[O-])=CC(S(=O)(=O)NC(=O)c3ccc(N4CCN(CC5=C(c6ccc(Cl)cc6)CC6(CCC6)CC5)CC4)cc3Oc3cnc4[nH]ccc4c3)=CC21] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-methyl-4-nitro-1H-benzo[d]imidazol-6-yl)sulfonyl)benzamide |
| 53 | 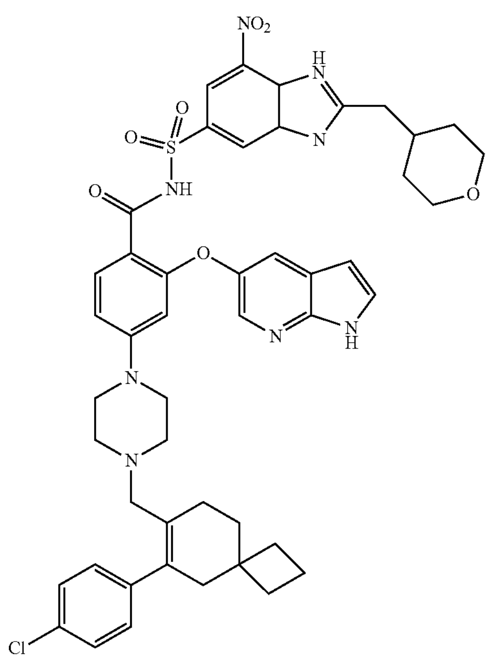 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-((tetrahydro-2H-pyran-4-yl)methyl)-1H-benzo[d]imidazol-5-yl)sulfonyl)benzamide |

TABLE 1-A-continued
| Cpd. No. | Structure | Name |
|---|---|---|
| 54 | 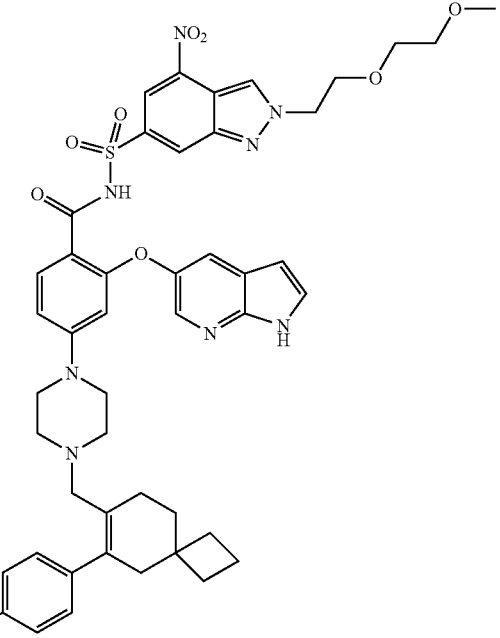 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-(2-(2-methoxyethoxy)ethyl)-4-nitro-2H-indazol-6-yl)sulfonyl)benzamide |
| 55 | 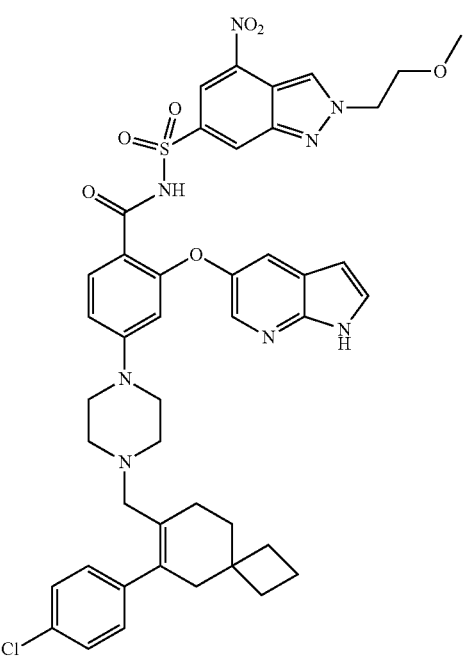 [SMILES: COCCn1cc2c([N+](=O)[O-])cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc2n1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-(2-methoxyethyl)-4-nitro-2H-indazol-6-yl)sulfonyl)benzamide |

TABLE 1-A-continued

| Cpd. No. | Structure | Name |
|---|---|---|
| 56 | 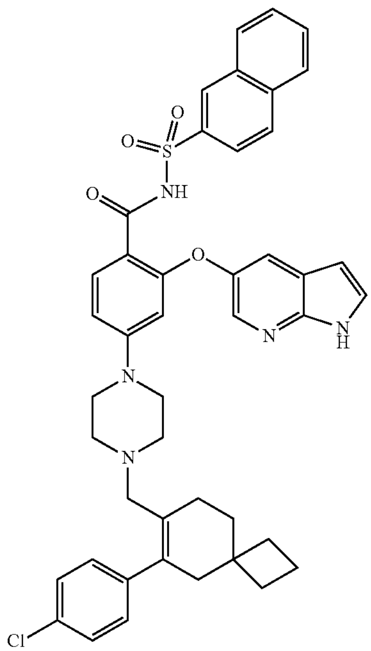 [SMILES: O=C(NS(=O)(=O)c1ccc2ccccc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-(naphthalen-2-ylsulfonyl)benzamide |

In some embodiments, the Bcl-2 inhibitor is a compound selected from one or more of the compounds of Table 1-1B, or a pharmaceutically acceptable salt or solvate thereof.

TABLE 1-B

| Cpd. No. | Structure | Name |
|---|---|---|
| 57 | 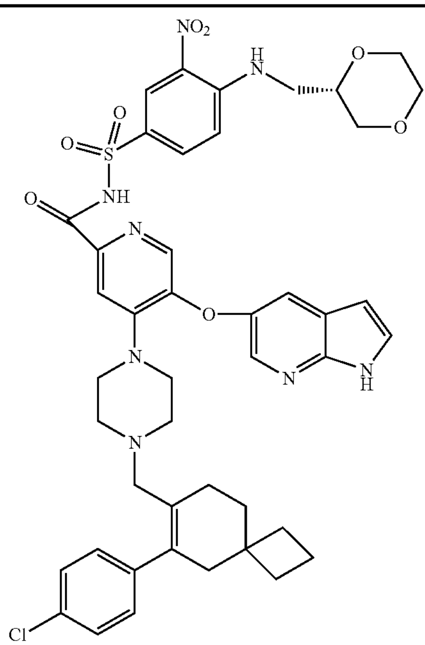 | (S)-N-((4-(((1,4-dioxan-2-yl)methyl)amino)-3-nitrophenyl)sulfonyl)-5-((1H-pyrrolo[2,3-b]pyridin-5-yl)oxy)-4-((6-(4-chlorophenyl)spiro[3.5]non-6-en-7-yl)methyl)piperazin-1-yl)picolinamide |

In some embodiments, the anti-CD20 mAb is selected from the group consisting of: Rituximab, IF5, Ibritumomab tiuxetan, tositumomab, ocrelizumab, veltuzumab, ofatumumab, obinutuzumab, AME133V, Pro13192 and GA101, TRU-015; preferably, the anti-CD20 mAb is Rituximab.

In some embodiments, the combination product is in the form of a pharmaceutical composition.

In some embodiments, the Bcl-2 inhibitor and the anti-CD20 mAb are each in a separate preparation.

In some embodiments, the Bcl-2 inhibitor, anti-CD20 mAb and bendamustine are each in a separate preparation.

In some embodiments, the Bcl-2 inhibitor and CHOP are each in a separate preparation.

In some embodiments, the Bcl-2 inhibitor and anti-CD20 mAb are administered simultaneously, sequentially or alternately.

In some embodiments, the Bcl-2 inhibitor, anti-CD20 mAb and bendamustine are administered simultaneously, sequentially or alternately.

In some embodiments, the Bcl-2 inhibitor and CHOP are administered simultaneously, sequentially or alternately.

In some embodiments, the Bcl-2 inhibitor and anti-CD20 mAb may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the Bcl-2 inhibitor, anti-CD20 mAb and bendamustine may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the Bcl-2 inhibitor and CHOP may be administered sequentially for about a time interval of 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 week, about 6 weeks, about 8 weeks, or about 12 weeks.

In some embodiments, the combination product of the invention comprising the Bcl-2 inhibitor and anti-CD20 mAb in the form of a pharmaceutical composition (preferably, each in a separate dosage unit form), as desired, can be daily administered for, including but not limited to: 1 time, 2 times, 3 times, 4 times, 5 times or 6 times.

In some embodiments, the combination product of the invention comprising the Bcl-2 inhibitor, anti-CD20 mAb and bendamustine in the form of a pharmaceutical composition (preferably, each in a separate dosage unit form), as desired, can be daily administered for, including but not limited to: 1 time, 2 times, 3 times, 4 times, 5 times or 6 times.

In some embodiments, the combination product of the invention comprising the Bcl-2 inhibitor and CHOP in the form of a pharmaceutical composition (preferably, each in a separate dosage unit form), as desired, can be daily administered for, including but not limited to, 1 time, 2 times, 3 times, 4 times, 5 times or 6 times.

In some embodiments, the combination product of the invention comprising the Bcl-2 inhibitor and anti-CD20 mAb in the form of a pharmaceutical composition (preferably, in the form of a dosage unit), as desired, can be daily administered for, including but not limited to, 1 time, 2 times, 3 times, 4 times, 5 times or 6 times.

In some embodiments, the combination product of the invention comprising the Bcl-2 inhibitor, anti-CD20 mAb and bendamustine in the form of a pharmaceutical composition (preferably, in the form of a dosage unit), as desired, can be daily administered for, including but not limited to, 1 time, 2 times, 3 times, 4 times, 5 times or 6 times.

In some embodiments, the combination product of the invention comprising the Bcl-2 inhibitor and CHOP in the form of a pharmaceutical composition (preferably, in the form of a dosage unit), as desired, can be daily administered for, including but not limited to, 1 time, 2 times, 3 times, 4 times, 5 times or 6 times.

In some embodiments, the combination product can be administered in the following manner oral, buccal, inhalation spray, sublingual, rectal, transdermal, vaginal mucosa, transmucosal, local, nasal or enteral administration; parenteral administration, such as intramuscular injection, subcutaneous injection, intramedullary injection, as well as intrathecal or brain direct administration, in situ administration, subcutaneous, intraperitoneal, intravenous injection, intra-articular synovium, intrasternal, intrahepatic, intralesional, intracranial, intra-abdominal, nasal, or intraocular injection or other drug delivery manners.

In some embodiments, the amount of the Bcl-2 inhibitor is 1 mg, 5 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 460 mg, 470 mg, 480 mg, 487 mg, 490 mg, 500 mg, 550 mg, 600 mg, 650 mg, 700 mg, 731 mg, 750 mg, 800 mg, 850 mg, 900 mg, 950 mg, 1000 mg, and a range between the respective amounts, for example, 1 mg to 1000 mg, 30 mg to 900 mg, 30 mg to 800 mg, 30 mg to 900 mg, 30 mg to 800 mg, 30 mg to 700 mg, 30 mg to 600 mg, 30 mg to 500 mg, 30 mg to 490 mg, 30 mg to 487 mg, 60 mg to 1000 mg, 60 mg to 900 mg, 60 mg to 800 mg, 60 mg to 731 mg, 731 mg to 1000 mg, etc.; and the amount of the anti-CD20 mAb is 1 mg, 5 mg, 10 mg, 15 mg, 16 mg, 17 mg, 18 mg, 19 mg, 19.5 mg, 20 mg, 25 mg, 30 mg, 35 mg, 40 mg, 41 mg, 42 mg, 43 mg, 44 mg, 45 mg, 46 mg, 47 mg, 48 mg, 48.8 mg, 49 mg, 50 mg, 60 mg, 70 mg, 80 mg, 90 mg, 100 mg, 150 mg, 200 mg, 250 mg, 300 mg, 350 mg, 400 mg, 450 mg, 500 mg, 600 mg, 650 mg, 700 mg, 800 mg, and a range between the respective amounts, for example, 1 mg to 800 mg, 10 mg to 800 mg, 15 mg to 5800 mg, 19.5 mg to 700 mg, 19.5 mg to 500 mg, 19.5 mg to 300 mg, 19.5 mg to 100 mg, 19.5 mg to 90 mg, 19.5 mg to 80 mg, 19.5 mg to 70 mg, 19.5 mg to 60 mg, 19.5 mg to 50 mg, 19.5 mg to 48.8 mg, etc.; the amount of the bendamustine is 1 mg, 5 mg, 10 mg, 20 mg, 30 mg, 40 mg, 50 mg, 60 mg, 70 mg, 80 mg, 90 mg, 100 mg, 110 mg, 120 mg, 121.95 mg, 150 mg, 160, 180, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, and a range between the respective amounts, for example, 1 mg to 1000 mg, 50 mg to 900 mg, 100 mg to 800 mg, 121.95 mg to 1000 mg, 121.95 mg to 900 mg, 121.95 mg to 800 mg, 121.95 mg to 700 mg, 121.95 mg to 600 mg, 121.95 mg to 500 mg, 121.95 mg to 400 mg, 121.95 mg to 300 mg, 121.95 mg to 200 mg, 121.95 mg to 150 mg, etc.; and the CHOP comprises: cyclophosphamide in an amount of 10 mg, 50 mg, 97.5 mg, 100 mg, 150 mg, and a range between the respective amounts, for example, 10 to 150 mg, 50 to 100 mg, 97.5 mg to 150 mg, etc.; doxorubicin in an amount of 1 mg, 5 mg, 9.75 mg, 10 mg, 15 mg, and a range between the respective amounts, for example, 1 mg to 15 mg, 5 mg to 10 mg, 9.75 mg to 15 mg, etc.; vincristine in an amount of 0.1 mg, 0.2 mg, 0.3 mg, 0.49 mg, 0.6 mg, 0.8 mg, 1 mg, 1.5 mg, and a range between the respective amounts, for example, 0.1 mg to 1.5 mg, 0.1 mg to 0.6 mg, 0.49 mg to 1.5 mg, etc.; prednisone in an amount of 0.5 mg, 1 mg, 1.5 mg, 2.44 mg, 5 mg, 10 mg, and a range between the respective amounts, For example, 0.5 mg to 10 mg, 0.5 mg to 5 mg, 2.44 mg to 10 mg, and the like.

In some embodiments, the combination product further comprises a pharmaceutically acceptable carrier, diluent or excipient.

In some embodiments, the combination product is in the form of tablet, capsule, granule, syrup, powder, lozenge, sachet, cachet, elixir, suspension, emulsion, solution, syrup, aerosol, ointment, cream and injection.

A second aspect of the invention relates to the use of a Bcl-2 inhibitor and an anti-CD20 mAb in the manufacture of a medicament for the prevention and/or treatment of a disease selected from the group consisting of cancer, rheumatoid arthritis (RA), granulomatosis with polyangiitis (GPA) and microscopic polyangiitis.

Meanwhile, the present invention relates to the use of a Bcl-2 inhibitor, an anti-CD20 mAb and bendamustine in the manufacture of a medicament for the prevention and/or treatment of a disease selected from the group consisting of cancer and rheumatoid arthritis (RA), granulomatosis with polyangiitis (GPA) and microscopic polyangiitis.

Further, the present invention relates to the use of a Bcl-2 inhibitor and CHOP in the manufacture of a medicament for the prevention and/or treatment of a disease, in which the disease is a cancer.

In some embodiments, the Bcl-2 inhibitor is a compound (e.g, Compound I-A), or a pharmaceutically acceptable salt or solvate thereof, as specifically described in the first aspect of the invention.

In some embodiments, the anti-CD20 mAb is selected from the group consisting of: Rituximab, IF5, Ibritumomab tiuxetan, tositumomab, ocrelizumab, veltuzumab, ofatumumab, obinutuzumab, AME133V, Pro13192 and GA101, TRU-015. Preferably, the anti-CD20 mAb is Rituximab.

In some embodiments, the drug is in the form of a pharmaceutical composition.

In some embodiments, the Bcl-2 inhibitor and the anti-CD20 mAb are each in a separate preparation.

In some embodiments, the Bcl-2 inhibitor, anti-CD20 mAb, and bendamustine are each in a separate preparation.

In some embodiments, the Bcl-2 inhibitor and CHOP are each in a separate preparation.

In some embodiments, the Bcl-2 inhibitor and anti-CD20 mAb are administered simultaneously, sequentially or alternately.

In some embodiments, the Bcl-2 inhibitor, anti-CD20 mAb, and bendamustine are administered simultaneously, sequentially, or alternately.

In some embodiments, the Bcl-2 inhibitor and CHOP are administered simultaneously, sequentially or alternately.

In some embodiments, the Bcl-2 inhibitor and anti-CD20 mAb may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the Bcl-2 inhibitor, anti-CD20 mAb and bendamustine may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the Bcl-2 inhibitor and CHOP may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 Week, about 6 weeks, about 8 weeks, or about 12 weeks.

In some embodiments, the medicament of the present invention comprising the Bcl-2 inhibitor and anti-CD20 mAb in the form of a pharmaceutical composition (preferably, each in a separate dosage unit form), as desired, may be daily administered for, including but not limited to: 1 time, 2 times, 3 times, 4 times, 5 times or 6 times.

In some embodiments, the medicament of the present invention comprising the Bcl-2 inhibitor, anti-CD20 mAb and bendamustine in the form of a pharmaceutical composition (preferably, each in a separate dosage unit form), as desired, may be daily administered for, including but not limited to: 1 time, 2 times, 3 times, 4 times, 5 times or 6 times.

In some embodiments, the medicament of the present invention comprising the Bcl-2 inhibitor and CHOP in the form of a pharmaceutical composition (preferably, each in a separate dosage unit form), as desired, may be daily administered for, including but not limited to: 1 time, 2 times, 3 times, 4 times, 5 times or 6 times.

In some embodiments, the medicament of the present invention comprising the Bcl-2 inhibitor and anti-CD20 mAb in the form of a pharmaceutical composition (preferably, in the form of a dosage unit), as desired, may be daily administered for, including but not limited to: 1 time, 2 times, 3 times, 4 times, 5 times or 6 times.

In some embodiments, the medicament of the present invention comprising the Bcl-2 inhibitor, anti-CD20 mAb and bendamustine in the form of a pharmaceutical composition (preferably, in the form of a dosage unit), as desired, may be daily administered for, including but not limited to: 1 time, 2 times, 3 times, 4 times, 5 times or 6 times.

In some embodiments, the medicament of the present invention comprising the Bcl-2 inhibitor and CHOP in the form of a pharmaceutical composition (preferably, in the form of a dosage unit), as desired, may be daily administered for, including but not limited to: 1 time, 2 times, 3 times, 4 times, 5 times or 6 times.

In some embodiments, the medicament can be administered in the following manner oral, buccal, inhalation spray, sublingual, rectal, transdermal, vaginal mucosa, transmucosal, local, nasal or enteral administration; parenteral administration, such as intramuscular injection, subcutaneous injection, intramedullary injection, as well as intrathecal or brain direct administration, in situ administration, subcutaneous, intraperitoneal, intravenous injection, intra-articular synovium, intrasternal, intrahepatic, intralesional, intracranial, intra-abdominal, nasal, or intraocular injection or other drug delivery manners.

In some embodiments, the Bcl-2 inhibitor or a pharmaceutically acceptable salt or solvate thereof, the anti-CD20 monoclonal antibody or a pharmaceutically acceptable salt or solvate thereof, the bendamustine or a pharmaceutically acceptable salt or solvate thereof, the CHOP (cyclophosphamide, doxorubicin, vincristine and prednisone) or a pharmaceutically acceptable salt or solvate thereof, are administered in doses as described in the first aspect of the invention in the above detailed description of the invention.

In some embodiments, the disease is cancer.

Further, the cancer described in the present invention includes, but is not limited to, a cancer selected from the group consisting of: adrenal cancer, lymphoid epithelioma, acinic cell carcinoma, lymphoma, acoustic neuroma, acute lymphocytic leukemia, acral lentiginous melanoma, acute myelogeous leukemia, acrospiroma, chronic lymphocytic leukemia, acute eosinophilic leukemia, liver cancer, acute erythroid leukemia, small cell lung cancer, acute lymphoblastic leukemia, non-small cell lung cancer, acute megakaryoblastic leukemia, MALT lymphoma, acute monocytic leukemia, malignant fibrous histiocytoma, acute promyelocytic leukemia, malignant peripheral schwannomas, adenocarcinoma, malignant triton tumor, adenoid cystic carcinoma, mantle cell lymphoma, adenoma, marginal zone B cell lymphoma, adenomatoid odontogenic tumor, mast cell leukemia, adenosquamous carcinoma, mediastinal germ cell tumor, adipose tissue neoplasm, medullary carcinoma of the breast, adrenal cortical carcinoma, medullary thyroid carcinoma, adult T-cell leukemia/lymphoma, medulloblastoma, aggressive NK cell leukemia, melanoma, AIDS-related lymphoma, meningiomas, alveolar rhabdomyosarcoma, merkel cell carcinoma, alveolar soft tissue sarcoma, mesothelioma, ameloblastic fibroma, metastatic urothelial carcinoma, anaplastic large cell lymphoma, mixed mullerian tumor, anaplastic thyroid cancer, mucinous tumor, angioimmunoblastic T-cell lymphoma, multiple myeloma, angiomyolipoma, muscle tissue neoplasm, angiosarcoma, mycosis fungoides, astrocytoma, myxoid liposarcoma, atypical malformation rhabdoid tumor, myxoma, B cell chronic lymphocytic leukemia, myxosarcoma, B-cell prolymphocytic leukemia, nasopharyngeal carcinoma, B-cell lymphoma, neurinoma, basal cell carcinoma, neuroblastoma, biliary tract cancer, neurofibroma, bladder cancer, neuroma, blastoma, nodular melanoma, bone cancer, ocular cancer, Brenner tumor, oligodendroglioma, brown tumor, oligodendroglioma, Burkitt's lymphoma, oncocytoma, breast cancer, optic nerve sheath meningioma, brain cancer, optic nerve tumor, carcinoma, oral carcinoma, carcinoma in situ, osteosarcoma, carcinosarcoma, ovarian cancer, cartilage tumor, pancoast tumor, cementoma, papillary thyroid carcinoma, myeloid sarcoma, paraganglioma, chondroma, pinealoblastoma, chordoma, pinealocytoma, choriocarcinoma, pituitary tumor, choroid plexus papilloma, pituitary adenoma, clear-cell sarcoma of the kidney, pituitary tumor, craniopharyngioma, plasmacytoma, cutaneous T-cell lymphoma, polyembryoma, cervical cancer, precursor T lymphoblastic lymphoma, colorectal cancer, primary central nervous system lymphoma, Degos disease, primary effusion lymphoma, desmoplastic small round cell tumor, primary peritoneal cancer, diffuse large B-cell lymphoma, prostate cancer, dysembryoplastic neuroepithelial tumor, pancreatic cancer, dysgerminoma, pharyngeal carcinoma, embryonal carcinoma, peritoneal pseudomyxoma, endocrine gland tumor, renal cell carcinoma, endodermal sinus tumor, renal medullary carcinoma, enteropathy-associated T-cell lymphoma, retinoblastoma, esophageal cancer, rhabdomyomas, fetus-in-fetu, rhabdomyosarcoma, fibroma, Richter's transformation, fibrosarcoma, rectal cancer, follicular lymphoma, sarcoma, follicular thyroid cancer, schwannomatosis, ganglioneuroma, seminoma, gastrointestinal cancer, sertoli cell tumor, germ cell tumor, sex cord-gonadal stromal tumor, gestational choriocarcinoma, signet ring cell carcinoma, giant cell fibroblastoma, skin cancer, giant cell tumor of bone, small blue round cell tumor, glial tumor, small cell carcinoma, glioblastoma multiforme, soft tissue sarcoma, glioma, somatostatinoma, gliomatosis cerebri, soot wart, glucagonoma, spinal tumor, gonadoblastoma, splenic marginal zone lymphoma, granulosa cell tumor, squamous cell carcinoma, gynandroblastoma, synovial sarcoma, gallbladder carcinoma, Sezary's disease, gastric cancer, small intestine cancer, hairy cell leukemia, squamous cell carcinoma, hemangioblastoma, stomach cancer, head and neck cancer, T-cell lymphoma, hemangiopericytoma, testicular cancer, hematological malignancy, hepatoblastoma, thyroid cancer, hepatosplenic T-cell lymphoma, transitional cell carcinoma, Hodgkin's lymphoma, throat cancer, non-Hodgkin's lymphoma, urachal carcinoma, invasive lobular carcinoma, urogenital cancer, intestinal cancer, urothelial carcinoma, kidney cancer, uveal melanoma, laryngeal cancer, uterine cancer, lentigo maligna, verrucous carcinoma, lethal midline carcinoma, visual pathway glioma, leukemia, vulvar cancer, testicular stromal tumor, vaginal cancer, liposarcoma, Waldenstrom's macroglobulinemia, lung cancer, adenolymphoma, lymphangioma, nephroblastoma and lymphangiosarcoma.

Preferably, the cancer is selected from the group consisting of: acute monocytic leukemia, acute myeloid leukemia, chronic myelogenous leukemia, chronic lymphocytic leukemia and mixed lineage leukemia, NUT midline cancer, multiple myeloma, small cell lung cancer, neuroblastoma, Burkitt's lymphoma, cervical cancer, esophageal cancer, ovarian cancer, colorectal cancer, prostate cancer and breast cancer.

Preferably, the cancer is a hematological malignancy.

More preferably, the hematological malignancy is selected from the group consisting of: acute myeloid leukemia (AML), acute lymphoblastic leukemia (ALL), diffuse large B-cell lymphoma (DLBCL), follicular lymphoma (FL), chronic lymphocytic leukemia (CLL)/small lymphocytic lymphoma (SLL), marginal zone lymphoma (MZL), chronic myelogenous leukemia (CML), mantle cell lymphoma (MCL), Waldenstrom's macroglobulinemia (WM). Most preferably, the hematological malignancy is selected from the group consisting of diffuse large B-cell lymphoma (DLBCL) and follicular lymphoma (FL).

Preferably, the cancer is selected from the group consisting of bladder cancer, breast cancer, cervical cancer, colon cancer (including colorectal cancer), esophageal cancer, head and neck cancer, liver cancer, lung cancer (small cell and non-small cell), melanoma, myeloma, neuroblastoma, ovarian cancer, pancreatic cancer, prostate cancer, kidney cancer, sarcoma (including osteosarcoma), skin cancer (including squamous cell carcinoma), gastric cancer, testicular cancer, thyroid cancer, uterine cancer, mesothelioma, cholangiocarcinoma, leiomyosarcoma, liposarcoma, melanoma, nasopharyngeal carcinoma, neuroendocrine carcinoma, ovarian cancer, renal cancer, salivary gland cancer, or metastatic tumor caused by spindle cell carcinoma, non-Hodgkin's lymphoma, Hodgkin's lymphoma, and hematologic malignancies such as acute myeloid leukemia (AML), acute lymphoblastic leukemia (ALL), diffuse large B-cell lymphoma (DLBCL), follicular lymphoma (FL), chronic lymphocytic leukemia (CLL), chronic myelogenous leukemia (CML).

In some embodiments, the disease is rheumatoid arthritis (RA), granulomatosis with polyangiitis (GPA) and microscopic polyangiitis.

A third aspect of the invention relates to a combination product for the prevention and/or treatment of a disease, in which the combination product comprises a Bcl-2 inhibitor and an anti-CD20 mAb, and the disease is selected from the group consisting of cancer, rheumatoid arthritis (RA), granulomatosis with polyangiitis (GPA) and microscopic polyangiitis. Further, the cancer includes, but is not limited to, those cancers as described in the second aspect of the invention in the above detailed description of the invention.

Meanwhile, the present invention relates to a combination product for the prevention and/or treatment of a disease, in which the combination product comprises a Bcl-2 inhibitor, an anti-CD20 mAb and bendamustine, and the disease is selected from the group consisting of cancer, Rheumatoid arthritis (RA), granulomatosis with polyangiitis (GPA) and microscopic polyangiitis.

Further, the present invention relates to a combination product for the prevention and/or treatment of a disease, in which the combination product comprises a Bcl-2 inhibitor and CHOP, and the disease is cancer.

In some embodiments, the Bcl-2 inhibitor is a compound (e.g, Compound I-A), or a pharmaceutically acceptable salt or solvate thereof, as specifically described in the first aspect of the invention.

In some embodiments, the anti-CD20 mAb is selected from the group consisting of: Rituximab, IF5, Ibritumomab tiuxetan, tositumomab, ocrelizumab, veltuzumab, ofatumumab, obinutuzumab, AME133V, Pro13192 and GA101, TRU-015. Preferably, the anti-CD20 mAb is Rituximab.

In some embodiments, the combination product is in the form of a pharmaceutical composition.

In some embodiments, the Bcl-2 inhibitor and the anti-CD20 mAb are each in a separate preparation.

In some embodiments, the Bcl-2 inhibitor, anti-CD20 mAb and bendamustine are each in a separate preparation.

In some embodiments, the Bcl-2 inhibitor and CHOP are each in a separate preparation.

In some embodiments, the Bcl-2 inhibitor and anti-CD20 mAb are administered simultaneously, sequentially or alternately.

In some embodiments, the Bcl-2 inhibitor, anti-CD20 mAb and bendamustine are administered simultaneously, sequentially or alternately.

In some embodiments, the Bcl-2 inhibitor and CHOP are administered simultaneously, sequentially or alternately.

In some embodiments, the Bcl-2 inhibitor and anti-CD20 mAb may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the Bcl-2 inhibitor, anti-CD20 mAb and bendamustine may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the Bcl-2 inhibitor and CHOP may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 Week, about 6 weeks, about 8 weeks, or about 12 weeks.

In some embodiments, the medicament of the present invention comprising the Bcl-2 inhibitor and anti-CD20 mAb in the form of a pharmaceutical composition (preferably, each in a separate dosage unit form), as desired, may be daily administered for, including but not limited to: 1 time, 2 times, 3 times, 4 times, 5 times or 6 times.

In some embodiments, the medicament of the present invention comprising the Bcl-2 inhibitor, anti-CD20 mAb and bendamustine in the form of a pharmaceutical composition (preferably, each in a separate dosage unit form), as desired, may be daily administered for, including but not limited to: 1 time, 2 times, 3 times, 4 times, 5 times or 6 times.

In some embodiments, the medicament of the present invention comprising the Bcl-2 inhibitor and CHOP in the form of a pharmaceutical composition (preferably, each in a separate dosage unit form), as desired, may be daily administered for, including but not limited to: 1 time, 2 times, 3 times, 4 times, 5 times or 6 times.

In some embodiments, the medicament of the present invention comprising the Bcl-2 inhibitor and anti-CD20 mAb in the form of a pharmaceutical composition (preferably, in the form of a dosage unit), as desired, may be daily administered for, including but not limited to: 1 time, 2 times, 3 times, 4 times, 5 times or 6 times.

In some embodiments, the medicament of the present invention comprising the Bcl-2 inhibitor, anti-CD20 mAb and bendamustine in the form of a pharmaceutical composition (preferably, in the form of a dosage unit), as desired, may be daily administered for, including but not limited to: 1 time, 2 times, 3 times, 4 times, 5 times or 6 times.

In some embodiments, the medicament of the present invention comprising the Bcl-2 inhibitor and CHOP in the form of a pharmaceutical composition (preferably, in the form of a dosage unit), as desired, may be daily administered for, including but not limited to: 1 time, 2 times, 3 times, 4 times, 5 times or 6 times.

In some embodiments, the combination product can be administered in the following manner oral, buccal, inhalation spray, sublingual, rectal, transdermal, vaginal mucosa, transmucosal, topical, nasal or enteral administration; parenteral administration, such as intramuscular injection, subcutaneous injection, intramedullary injection, as well as intrathecal or brain direct administration, in situ administration, subcutaneous, intraperitoneal, intravenous injection, intra-articular synovium, intrasternal, intrahepatic, intralesional, intracranial, intra-abdominal, nasal, or intraocular injection or other drug delivery manners.

In some embodiments, the Bcl-2 inhibitor, or a pharmaceutically acceptable salt or solvate thereof, the anti-CD20 monoclonal antibody or a pharmaceutically acceptable salt or solvate thereof, the bendamustine or a pharmaceutically acceptable salt or solvate thereof, the CHOP (cyclophosphamide, doxorubicin, vincristine and prednisone) or a pharmaceutically acceptable salt or solvate thereof, are administered in doses as described in the first aspect of the invention in the above detailed description of the invention.

A fourth aspect of the invention relates to a method of preventing and/or treating a disease comprising administering to a subject in need thereof a prophylactically and/or therapeutically effective amount of the Bcl-2 inhibitor and anti-CD20 mAb, in which the disease is selected from the group consisting of cancer, rheumatoid arthritis (RA), granulomatosis with polyangiitis (GPA) and microscopic polyangiitis. Further, the cancer includes, but is not limited to, those cancers as described in the second aspect of the invention in the above detailed description of the invention.

At the same time, the invention relates to a method of preventing and/or treating a disease comprising administering to a subject in need thereof a prophylactically and/or therapeutically effective amount of the Bcl-2 inhibitor, anti-CD20 mAb and bendamustine, in which the disease is selected from the group consisting of cancers, autoimmune diseases, and inflammatory diseases.

Further, the present invention relates to a method of preventing and/or treating a disease comprising administering to a subject in need thereof a prophylactically and/or therapeutically effective amount of the Bcl-2 inhibitor and CHOP, in which the disease is cancer.

In some embodiments, the Bcl-2 inhibitor is a compound (e.g., Compound I-A) or a pharmaceutically acceptable salt or solvate thereof, as specifically described in the first aspect of the invention.

In some embodiments, the anti-CD20 mAb is selected from the group consisting of: Rituximab, IF5, Ibritumomab tiuxetan, tositumomab, ocrelizumab, veltuzumab, ofatumumab, obinutuzumab, AME133V, Pro13192 and GA101, TRU-015. Preferably, the anti-CD20 mAb are Rituximab.

In some embodiments, the Bcl-2 inhibitor and anti-CD20 mAb are in the form of a pharmaceutical composition.

In some embodiments, the Bcl-2 inhibitor and the anti-CD20 mAb are each in a separate preparation.

In some embodiments, the Bcl-2 inhibitor, anti-CD20 mAb and bendamustine are each in a separate preparation.

In some embodiments, the Bcl-2 inhibitor and CHOP are each in a separate preparation.

In some embodiments, the Bcl-2 inhibitor and anti-CD20 mAb are administered simultaneously, sequentially or alternately.

In some embodiments, the Bcl-2 inhibitor, anti-CD20 mAb and bendamustine are administered simultaneously, sequentially or alternately.

In some embodiments, the Bcl-2 inhibitor and CHOP are administered simultaneously, sequentially or alternately.

In some embodiments, the Bcl-2 inhibitor and anti-CD20 mAb may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the Bcl-2 inhibitor, anti-CD20 mAb and bendamustine may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 weeks, about 6 weeks, about 8 weeks, or about 12 weeks.

In some embodiments, the Bcl-2 inhibitor and CHOP may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, about 5 week, about 6 weeks, about 8 weeks, or about 12 weeks.

In some embodiments, the medicament of the present invention comprising the Bcl-2 inhibitor and anti-CD20 mAb in the form of a pharmaceutical composition (preferably, each in a separate dosage unit form), as desired, may be daily administered for, including but not limited to: 1 time, 2 times, 3 times, 4 times, 5 times or 6 times.

In some embodiments, the medicament of the present invention comprising the Bcl-2 inhibitor, anti-CD20 mAb and bendamustine in the form of a pharmaceutical composition (preferably, each in a separate dosage unit form), as desired, may be daily administered for, including but not limited to: 1 time, 2 times, 3 times, 4 times, 5 times or 6 times.

In some embodiments, the medicament of the present invention comprising the Bcl-2 inhibitor and CHOP in the form of a pharmaceutical composition (preferably, each in a separate dosage unit form), as desired, may be daily administered for, including but not limited to: 1 time, 2 times, 3 times, 4 times, 5 times or 6 times.

In some embodiments, the medicament of the present invention comprising the Bcl-2 inhibitor and anti-CD20 mAb in the form of a pharmaceutical composition (preferably, in the form of a dosage unit), as desired, may be daily administered for, including but not limited to: 1 time, 2 times, 3 times, 4 times, 5 times or 6 times.

In some embodiments, the medicament of the present invention comprising the Bcl-2 inhibitor, anti-CD20 mAb and bendamustine in the form of a pharmaceutical composition (preferably, in the form of a dosage unit), as desired, may be daily administered for, including but not limited to: 1 time, 2 times, 3 times, 4 times, 5 times or 6 times.

In some embodiments, the medicament of the present invention comprising the Bcl-2 inhibitor and CHOP in the form of a pharmaceutical composition (preferably, in the form of a dosage unit), as desired, may be daily administered for, including but not limited to: 1 time, 2 times, 3 times, 4 times, 5 times or 6 times.

In some embodiments, the Bcl-2 inhibitor, anti-CD20 mAb and CHOP can be administered in the following manner oral, buccal, inhalation spray, sublingual, rectal, transdermal, vaginal mucosa, transmucosal, local, nasal or enteral administration; parenteral administration, such as intramuscular injection, subcutaneous injection, intramedullary injection, as well as intrathecal or brain direct administration, in situ administration, subcutaneous, intraperitoneal, intravenous injection, intra-articular synovium, intrasternal, intrahepatic, intralesional, intracranial, intraabdominal, nasal, or intraocular injection or other drug delivery manners.

In some embodiments, the Bcl-2 inhibitor is administered daily at a dose of 0.017 mg/kg, 0.083 mg/kg, 0.17 mg/kg, 0.33 mg/kg, 0.5 mg/kg, 0.67 mg/kg, 0.83 mg/kg, 1 mg/kg, 1.16 mg/kg, 1.33 mg/kg, 1.5 mg/kg, 1.67 mg/kg, 2.5 mg/kg, 3.33 mg/kg, 4.17 mg/kg, 5 mg/kg, 5.83 mg/kg, 6.67 mg/kg, 7.5 mg/kg, 7.67 mg/kg, 7.83 mg/kg, 8 mg/kg, 8.12 mg/kg, 8.16 mg/kg, 8.33 mg/kg, 9.17 mg/kg, 10 mg/kg, 10.83 mg/kg, 11.66 mg/kg, 12.5 mg/kg, 13.33 mg/kg, 14.17 mg/kg, 15 mg/kg, 15.83 mg/kg, 16.67 mg/kg, and a range between the respective doses, for example, 0.017 mg to 16.67 mg/kg, 0.083 mg to 16.67 mg/kg, 0.17 mg to 16.67 mg/kg, 0.33 mg to 16.67 mg/kg, 0.5 mg to 15 mg/kg, 0.5 mg to 13.33 mg/kg, 0.5 mg to 11.67 mg/kg, 0.5 mg to 10 mg/kg, 0.5 mg to 8.33 mg/kg, 0.5 mg to 8.16 mg/kg, 0.5 mg to 8.12 mg/kg, etc.; and the daily administration dose of the anti-CD20 mAb is 0.16 mg/kg, 0.25 mg/kg, 0.325 mg, 0.41 mg/kg, 0.66 mg/kg, 0.75 mg/kg, 0.81 mg, 1 mg/kg, 1.33 mg/kg, 1.66 mg/kg, 3.33 mg/kg, 5 mg/kg, 6.66 mg/kg, 8.33 mg kg, and a range between the respective doses, for example, 0.16 mg to 8.33 mg/kg, 0.16 mg to 0.81 mg/kg, 0.325 mg to 8.33 mg/kg, 0.81 mg to 8.33 mg/kg, 0.325 mg to 8.33 mg/kg, etc.; and the daily administration dose of bendamustine is 0.16 mg/kg, 0.83 mg/kg, 1.33 mg/kg, 1.66 mg/kg, 2.03 mg, 3.33 mg/kg, 5 mg/kg, 6.66 mg/kg, 8.33 mg/kg, 16.6 mg/kg, and a range between the respective doses, for example, 0.16 mg to 16.6 mg/kg, 0.16 mg to 2.03 mg/kg, 2.03 mg to 16.6 mg/kg, 2.03 mg to 16.6 mg/kg, etc.; and the CHOP includes: cyclophosphamide at a daily dose of 0.16 mg/kg, 0.83 mg/kg, 1.625 mg/kg, 1.66 mg/kg, 2.5 mg/kg, and a range between the respective doses, for example, 0.16 to 2.5 mg/kg, 0.83 to 2.5 mg/kg, 1.66 mg to 2.5 mg/kg, etc.; doxorubicin at a daily dose of 0.016 mg/kg, 0.083 mg/kg, 0.162 mg/kg, 0.166 mg/kg, 0.25 mg/kg, and a range between the respective doses, for example, 0.016 mg to 0.25 mg/kg, 0.083 mg to 0.25 mg/kg, 0.162 mg to 0.25 mg/kg, etc.; vincristine at a daily dose of 0.0016 mg/kg, 0.0033 mg/kg, 0.005 mg/kg, 0.0081 mg/kg, 0.016 mg/kg, 0.025 mg/kg, and a range between the respective doses, for example, 0.0016 mg to 0.025 mg/kg, 0.0033 mg to 0.025 mg/kg, 0.0081 mg to 0.025 mg/kg, etc.; prednisone at a daily dose of 0.0083 mg/kg, 0.016 mg/kg, 0.025 mg/kg, 0.04 mg/kg, 0.083 mg/kg, 0.16 mg/kg, and a range between the respective doses, for example, 0.0083 mg to 0.16 mg/kg, 0.025 mg to 0.16 mg/kg, 0.04 mg to 0.16 mg/kg, and the like.

Lastly, WO 2018/027097 is incorporated by reference herein, in its entirety and for all purposes.

EXAMPLES THE INVENTION

The present invention will be further illustrated by the following examples and control examples. However, it should be understood that these examples and control examples are merely used to explain the invention in more details, but not intend to limit the present invention.

Example 1. General Experimental Methods Used in the Invention (1) Experimental Evaluation Method for In Vivo Pharmacodynamics Cell inoculation method was used to establish a subcutaneous xenograft model in human tumor immunodeficient mice to test anti-proliferative effect (Gould S E et al. Translational value of mouse models in oncology drug development. Nature medicine. 2015 21, 431-439): tumor cells in logarithmic phase were collected and counted, resuspended in 1×PBS, and adjusted to a cell suspension concentration of 2.5-5×10$^7$/mL. The tumor cells were inoculated subcutaneously in the right flank of immunodeficient mice with a 1 mL syringe (4 gauge needle), 5-10×10$^6$/0.2 mL/mouse (experimental animals were purchased from Beijing Vital River Laboratory Animal Technology Co., Ltd., SCXK (Beijing) 2016-0006). All animal experiments were strictly in accordance with the laboratory animal use and management practices of GenePharma Co., Ltd. and Ascentage Pharma Group Co., Ltd. The calculation of relevant parameters referred to the Chinese CFDA "Guidelines for Non-Clinical Research Techniques of Cytotoxic Antitumor Drugs".

Cell lines were obtained as follows: Toledo was purchased from Miaoshun (Shanghai) Biotechnology Co., Ltd.; OCI-LY8 was from the Cancer Center of Sun Yat-sen University; DOHH2 was a gift from Professor Wang Shaomeng of the University of Michigan, USA. The cells used in the above invention were all commercially available from the American Type Culture Collection (ATCC).

The animal body weight and tumor size were measured twice weekly during the experiment. The conditions and death of the animals were observed every day. Routine monitoring included the effects of tumor growth and treatment on normal animal behaviors, including activity, feeding and drinking situations, weight gain or loss, eyes, coat and other abnormalities in the experimental animals. The deaths and clinical symptoms observed during the experiment were recorded in the raw data. The entire operations of administration, measurement of mouse body weight and tumor volume were performed in a clean bench. Plasma and tumor tissues were collected, weighed and photographed after the end of the last administration according to the experimental protocol. Plasma and tumor samples were snap frozen and stored at −80° C.

Tumor volume (TV) was calculated as: $TV = a \times b^2/2$, in which a and b represented the length and width of the tumor as measured, respectively. The relative tumor volume (RTV) was calculated as: $RTV = V_t/V_1$, in which $V_1$ was the tumor volume at the time of grouping and administration, and $V_t$ was the tumor volume measured on a day after administration. The evaluation index of anti-tumor activity was the relative tumor proliferation rate T/C (%), which was calculated as: relative tumor proliferation rate T/C (%)=(TRTV/CRTV)×100%, in which TRTV was the RTV of the treatment group, CRTV was the RTV of the vehicle control group; tumor remission rate (%) was calculated as: (the number of SD (stable disease), PR (tumor partial regression) and CR (tumor complete regression) in the tumor-bearing mice after treatment)/the total number of mice in the group× 100%.

Change of body weight %=(measured body weight−body weight at the time of grouping)/body weight at the time of grouping×100%.

Evaluation criteria of therapeutic efficiency: according to the Chinese CFDA "Technical guidelines for non-clinical research on cytotoxic antitumor drugs" (November 2006), it was determined as effective when the T/C (%) value was ≤40% and statistical analysis showed p<0.05; and a dose of the drug was considered to be severely toxic when the body weight of the mice dropped by more than 20% or the rate of drug-related mortality exceeded 20%.

The synergistic analysis was performed by the following formula: synergy factor=((A/C)×(B/C))/(AB/C); A=RTV value of the group administered with A only; B=RTV value of the group administered with B only; C=RTV value of the vehicle control group; AB=RTV value of the group administered with A and B in combination (Clarke R. Issues in experimental design and endpoint analysis in the study of experimental cytotoxic agents in vivo in breast cancer and other models [J]. Breast Cancer Research & Treatment, 1997, 46(2-3): 255-278). If the synergy factor was >1, there was a synergistic effect; if the synergistic factor=1, there was an additive effect; if the synergistic factor <1, there was an antagonistic effect.

Example 2. Preparation of Exemplary Compounds as Bcl-2 Inhibitors (Compounds 3, 6 and 13)

(1) Synthesis of 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)benzamide (Compound 3)

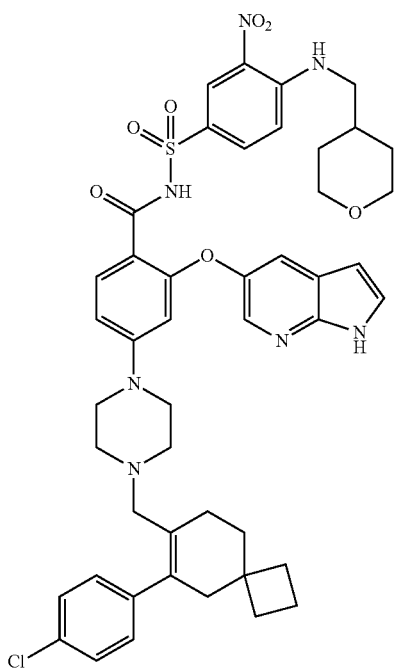 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)cc1Oc1cnc2[nH]ccc2c1]

A mixture of 2-((1H-pyrrolo[2,3-b]pyridin-5-yl)oxy)-4-(4-((6-(4-chlorophenyl) spiro[3.5]non-6-en-7-yl)methyl)piperazin-1-yl)benzoic acid (1.75 g, 3 mmol), 3-nitro-4-(((tetrahydro-2H-pyran-4-yl)methyl)amino) benzenesulfonamide (1.43 g, 4.5) reacted in EDCl (1.15 g, 6 mmol) and 4-(N,N-dimethylamino)pyridine (550 mg, 4.5 mmol) and dichloromethane (40 ml) at room temperature overnight, and then water was added. The aqueous layer was extracted with dichloromethane. The combined organic layers were washed with brine, concentrated and purified with silica gel column to obtain 2-((1H-pyrrolo[2,3-b]pyridin-5-yl)oxy)-4-(4-((6-(4-chlorophenyl)spiro[3.5]non-6-en-7-yl) methyl)piperazin-1-yl)-N-((3-nitro-4-((tetrahydro-2H-pyran-4-yl)methyl)amino)phenyl)sulfonyl)benzamide (1.7 g, 64.4%) was obtained as a yellow solid.

1H NMR (400 MHz, methanol-d4) δ 8.70 (d, J=2.3 Hz, 1H), 8.01 (d, J=2.7 Hz, 1H), 7.87 (d, J=9.2, 2.3 Hz, 1H), 7.66 (d, J=8.9 Hz, 1H), 7.55 (d, J=2.7 Hz, 1H), 7.47 (d, J=3.4 Hz, 1H), 7.38 (d, J=8.4 Hz, 2H), 7.10 (d, J=8.4 Hz, 2H), 6.97 (d, J=9.2 Hz, 1H), 6.77 (dd, J=8.9, 2.4 Hz, 1H), 6.44 (d, J=3.4 Hz, 1H), 6.34 (d, J=2.4 Hz, 1H), 4.02-3.94 (m, 3H), 3.66 (s, 3H), 3.49-3.38 (m, 2H), 3.41-3.25 (m, 7H), 2.42 (s, 3H), 2.26 (s, 3H), 2.00-1.67 (m, 4H), 1.45-1.38 (m, 2H).

(2) Synthesis of (R)—N-((4-(((1,4-dioxan-2-yl)methyl)amino)-3-nitrophenyl) sulfonyl)-2-((1H-pyrrolo[2,3-b]pyridin-5-yl)oxy)-4-(4-((6-(4-chlorophenyl)spiro[3.5]non-6-en-7-yl)) methyl)piperazin-1-yl)benzamide (Compound 13)

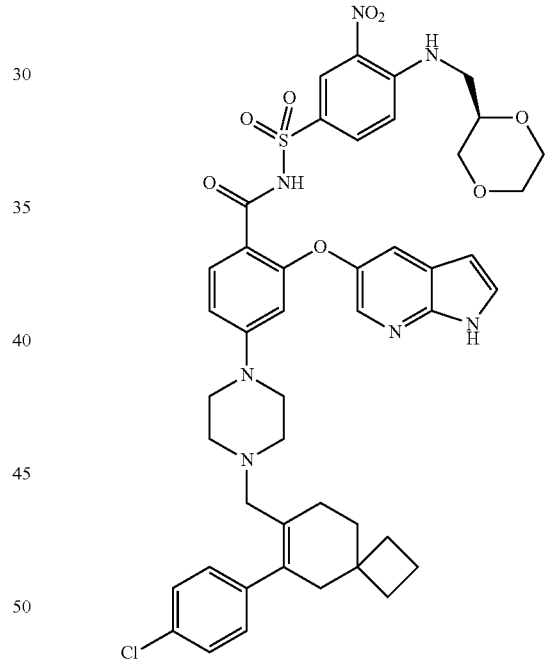

The title compound was prepared in a similar manner to that described for the synthesis of Compound 3.

1H NMR (400 MHz, methanol-d4) δ 8.66 (d, J=2.4 Hz, 1H), 7.99 (d, J=2.4 Hz, 1H), 7.84 (dd, J=9.2, 2.4 Hz, 1H), 7.64 (d, J=8.9 Hz, 1H), 7.51 (d, J=2.4 Hz, 2H), 7.45 (d, J=3.3 Hz, 1H), 7.37 (d, J=8.4 Hz, 2H), 7.10 (d, J=8.4 Hz, 2H), 6.94 (d, J=9.2 Hz, 1H), 6.76 (dd, J=8.9, 2.3 Hz, 1H), 6.40 (d, J=3.3 Hz, 1H), 6.36 (d, J=2.3 Hz, 1H), 3.87 (dd, J=11.8, 4.2 Hz, 3H), 3.83-3.70 (m, 3H), 3.67 (s, 2H), 3.62 (dd, J=11.7, 2.9 Hz, 1H), 3.51-3.41 (m, 2H), 3.40-3.35 (m, 1H), 3.29 (dq, J=3.2, 1.6 Hz, 1H), 2.41 (s, 2H), 2.26 (s, 2H), 2.00-1.77 (m, 6H).

Similarly, Compound 6 was prepared similarly according to the method described for the synthesis of Compound 13, with specific reference to WO 2018/027097.

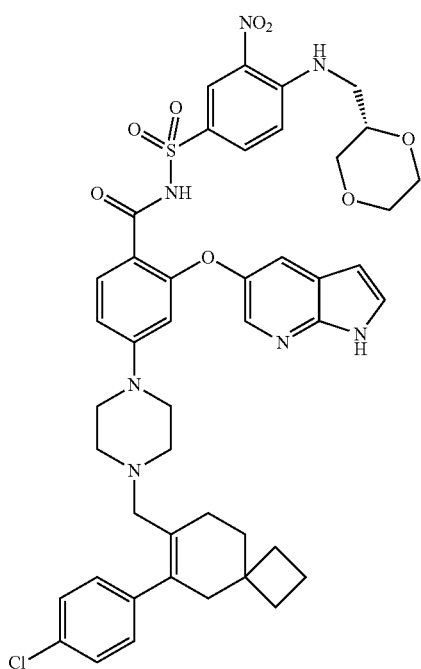

Compound 6

Example 3: Effects of Compound 6 in Combination with Rituximab (Anti-CD20 Antibody) in Mouse Xenograft Tumor Model 1. Anti-Tumor Effect in a Human DLBCL Toledo Cell Line Mouse Xenograft Tumor Model (1) The experimental method was as described in Example 1. In the in vitro cell experiments, Toledo was one of the human DLBCL cell lines sensitive to Compound 6, with an $IC_{50}$ value of 0.049±0.005 µM. Therefore, this experiment established the Toledo mouse xenograft tumor model (Andrew J Souers et al., ABT-199, a potent and selective BCL-2 inhibitor, achieves antitumor activity while sparing platelets. Nature Medicine vol 19, 202-208 (2013)). When the tumor volume reached 100-200 mm$^3$, randomization was performed according to tumor volume and mouse body weight. The anti-tumor effect of Compound 6 in combination with rituximab was evaluated on this model.

(2) Experimental Results

As shown in FIG. 1A and Table 1, Compound 6 was administered at a regimen of 100 mg/kg, p.o., qd×14 days. At the end of the experiment (d15), the T/C value was 38% (P<0.01). Rituximab failed to inhibit tumor growth after administration at a dose of 4 mg/kg i.v., qw regimen, with a T/C value of 69% (P>0.05). However, Compound 6 combined with rituximab showed an enhanced anti-tumor activity with a T/C value of 19% (P<0.01). Synergistic analysis (for a description of the synergistic analysis, please refer to: Clarke R. Issues in experimental design and endpoint analysis in the study of experimental cytotoxic agents in vivo in breast cancer and other models [J]. Breast Cancer Research & Treatment, 1997, 46 (2-3): 255-278) showed that the combination of the two drugs produced a synergistic anti-tumor effect that was significantly superior to that of single drugs.

TABLE 1

Anti-tumor effects of Compound 6 alone or in combination with rituximab in human Toledo (DLBCL) mouse xenograft tumor model

| Treatment | RTV on the 15th day after administration (mean ± standard error) | T/C (%) on the 15th day after administration | Synergistic factor |
|---|---|---|---|
| Solvent | 13.08 ± 2.28 | — | — |
| Compound 6 | 4.93 ± 0.41** | 38 | — |
| Rituximab | 8.99 ± 2.15 | 69 | — |
| Compound 6 + rituximab | 2.47 ± 0.30**##+ | 19 | 1.37 |

**P < 0.01, compared with the solvent group;

P < 0.01, compared with the Compound 6 group;

+P < 0.05, compared with the rituximab group.

Synergistic factor > 1, synergistic effect; synergistic factor = 1, additive effect; synergistic factor < 1, antagonistic effect.

(3) Summary

Compound 6 in combination with rituximab had no significant side effects (FIG. 1B), but significantly increased the anti-tumor effect of single drug in human Toledo (DLBCL) mouse xenograft tumor model, with significant synergistic effect (synergistic factor was 1.37, greater than 1). Therefore, the combination of Compound 6 with rituximab may clinically benefit patients with diffuse large B-cell lymphoma (DLBCL).

2. Anti-Tumor Effect in Human OCI-LY8 Cell Line DLBCL Mouse Xenograft Tumor Model (1) The experimental method was as described in Example 1. In the in vitro experiment, OCI-LY8 cells were also human DLBCL cell lines sensitive to Compound 6 treatment, with an $IC_{50}$ value of 0.006±0.002 μM. Therefore, this experiment used OCI-LY8 cells to establish a mouse xenograft tumor model (A. Esteve-Arenys et al. The BET bromodomain inhibitor CPI203 overcomes resistance to ABT-199 (venetoclax) by downregulation of BFL-1/A1 in in vitro and in vivo models of MYC+/BCL2+ double hit lymphoma. Oncogene 37(14). January 2018), and thereby evaluated the anti-tumor effect of Compound 6 in combination with rituximab.

(2) Experimental Results

Figure 2:
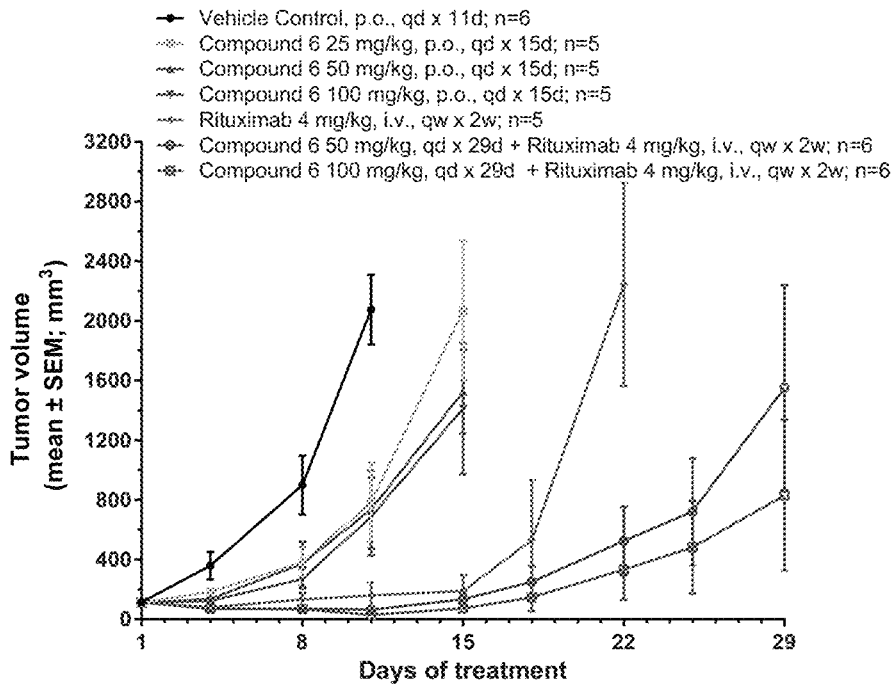
FIG. 2 shows the anti-tumor effect (A) and body weight change (B) caused by Compound 6 alone or in combination with rituximab in a human OCI-LY8 (DLBCL) mouse xenograft model.
Figure 2:
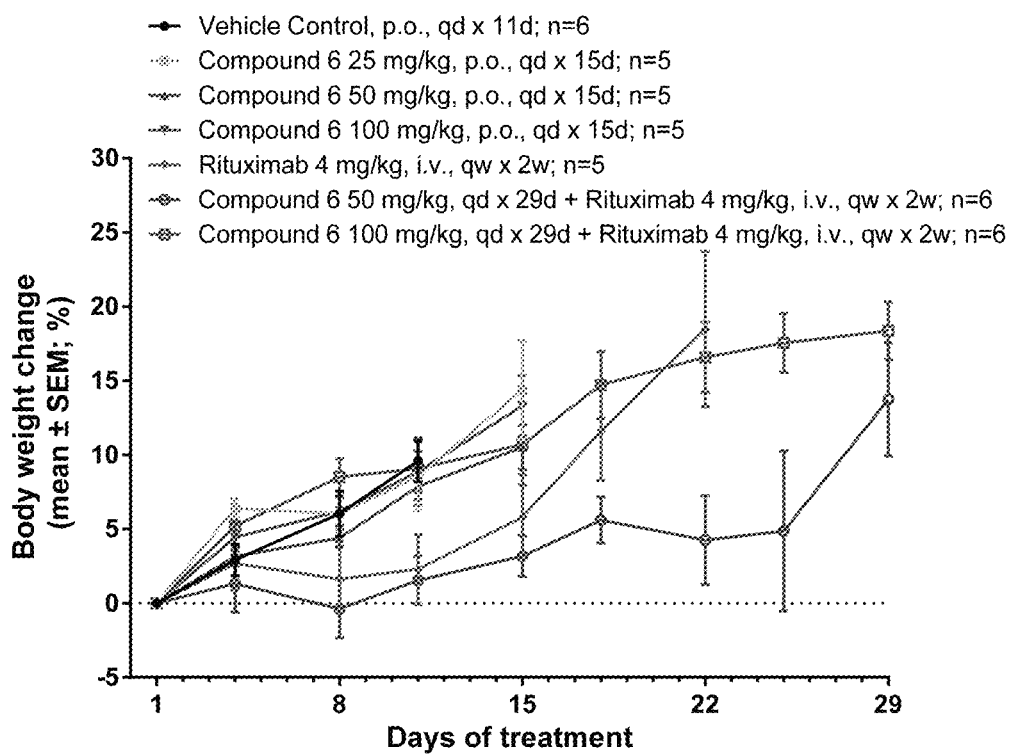

As shown in FIG. 2A and Table 2, OCI-LY8 showed a rapidly growing xenograft tumor, and on the 11th day after administration, the control animals were euthanized because the tumor volume exceeded the limit allowed by the animal welfare. The regimens of Compound 6 at doses of 25, 50 and 100 mg/kg, p.o., qd×15d, respectively showed T/C values of 37% (P<0.01), 33% (P<0.001) and 30% (P<0.001) at the day 11. The T/C value of rituximab at a dose of 4 mg/kg, i.v., qw×2 wks, reached 7% (P<0.001). Four out of five animals achieved PR (remission rate was 80%). The T/C values of Compound 6 in combination with rituximab at doses of 50 mg/kg and 100 mg/kg were 3% (P<0.001) and 2% (P<0.001), respectively. In the group administered with Compound 6 at dose of 50 mg/kg in combination with rituximab, 5/6 of the animals achieved PR (remission rate of 83%), while in the group administered with Compound 6 at dose of 100 mg/kg in combination with rituximab, PR was observed in 6/6 of the animals (remission rate was 100%). In addition, on the 22th day after administration and under the situation of drug discontinuance, in comparison with the rituximab single group, $T/C_{RTV}$ values of combination group at 50 mg/kg (Compound 6) or 100 mg/kg (Compound 6) were 23% (P<0.05) and 15% (P<0.05), respectively, indicating a significant increase in the inhibition of tumor growth by the two combination groups.

TABLE 2

Anti-tumor effects of Compound 6 alone or in combination with rituximab in human OCI-LY8 (DLBCL) mouse xenograft tumor model

| Treatment | RTV on the 11th day after administration (mean ± standard error) | T/C (%) on the 11th day after administration | RTV on the 22nd day after administration (mean ± standard error) | $T/C_{RTV}$ (%) on the 22nd day after administration | Tumor status on the 11th day after administration (remission rate %$^a$) | Synergistic factor on the 11th day after administration |
|---|---|---|---|---|---|---|
| Solvent | 18.80 ± 1.2 | — | — | — | 0/6 CR, 0/6 PR(0%) | — |
| Cpd. 6, 25 mg/kg | 6.87 ± 2.1 ** | 37 | — | — | 0/5 CR, 0/5 PR(0%) | — |
| Cpd. 6, 50 mg/kg | 6.19 ± 1.86*** | 33 | — | — | 0/5 CR, 0/5 PR(0%) | — |
| Cpd. 6, 100 mg/kg | 5.54 ± 1.78*** | 30 | — | — | 0/5 CR, 0/5 PR(0%) | — |
| Rituximab 4 mg/kg | 1.38 ± 0.69*** | 7 | 20.04 ± 5.38 | — | 0/5 CR, 4/5 PR(80%) | — |
| Cpd. 6, 50 mg/kg + Rituximab | 0.55 ± 0.16***# | 3 | 4.61 ± 1.93† | 23 | 0/6 CR, 5/6 PR(83%) | 0.83 |
| Cpd. 6, 100 mg/kg + Rituximab | 0.28 ± 0.05***# | 2 | 3.10 ± 1.851 | 15 | 0/6 CR, 6/6 PR(100%) | 1.45 |

**P < 0.01,
***P < 0.001, compared with the vehicle control group;
P < 0.05, compared with the single Compound 6 group;
†P < 0.05, compared with the rituximab group;
$^a$remission including CR, PR and SD.
Synergy factor = 1, additive effect; synergistic factor < 1, antagonistic effect.

(3) Summary

Compound 6 in combination with rituximab had no significant side effects (FIG. 2B) and significantly increased the anti-tumor effect in comparison with the single arm of Compound 6 or rituximab in the OCI-LY8 human DLBCL cell mouse xenograft tumor model. Therefore, the combination of Compound 6 with rituximab may clinically benefit patients with diffuse large B-cell lymphoma (DLBCL).

Example 4: Effects of Compound 6 in Combination with Rituximab and Bendamustine on Mouse Xenograft Tumor Model 1. Anti-Tumor Effect in Human OCI-LY8 Cell Line DLBCL Mouse Xenograft Tumor Model (1) The experimental method was as described in Example 1. Bendamustine was an FDA approved drug for the treatment of B-cell non-Hodgkin's lymphoma. The anti-tumor effect of Compound 6 with bendamustine (B: 25 mg/kg, i.v.) and rituximab (R: 10 mg/kg, i.v.) in combination (BR) was subsequently evaluated in the same experiment.

Figure 3:
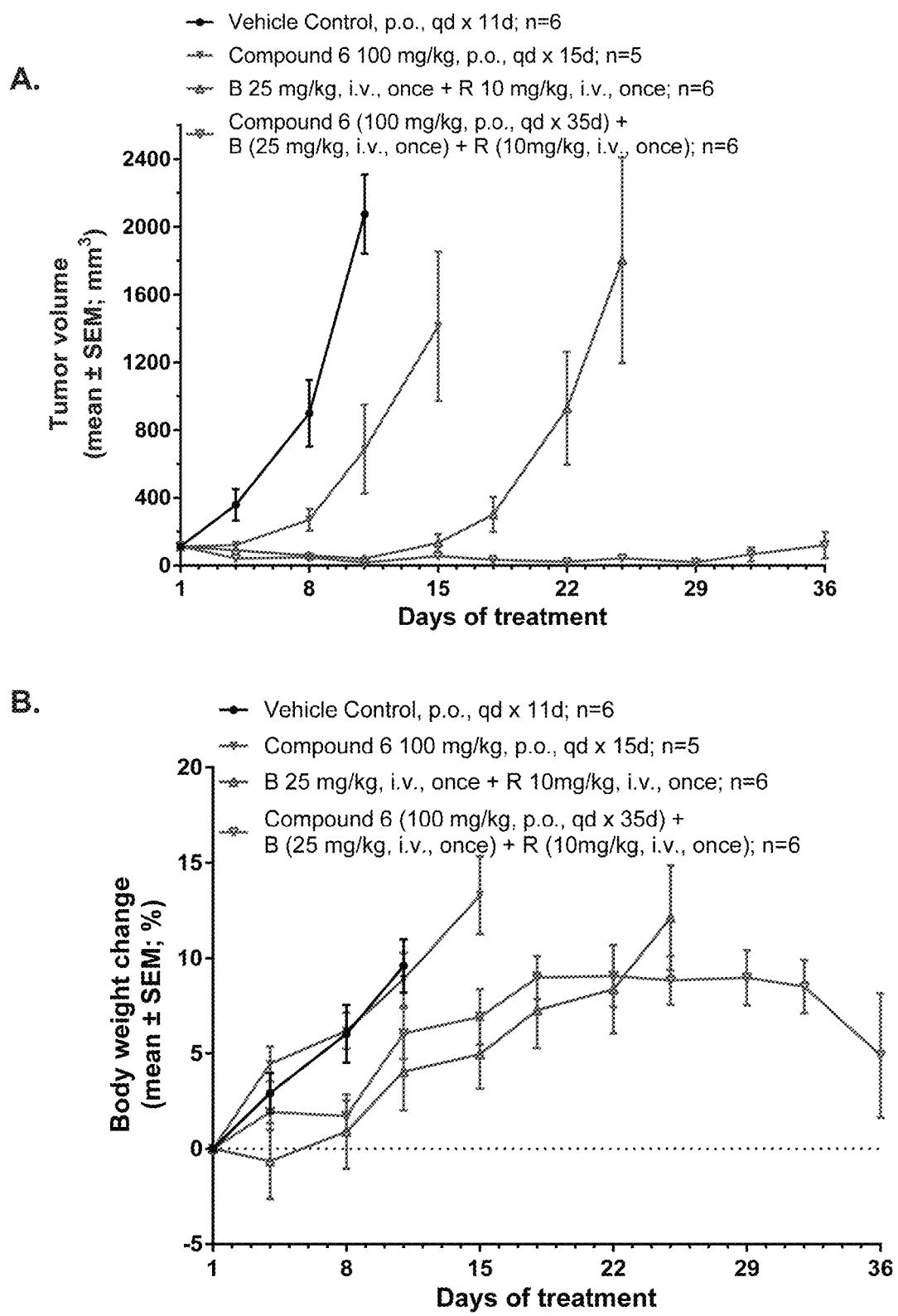
FIG. 3 shows the anti-tumor effect (A) and body weight change (B) caused by Compound 6 alone or in combination with BR (bendamustine+rituximab) in a human OCI-LY8 (DLBCL) mouse xenograft model (B of BR means bendamustine, and R of BR is rituximab).

(2) As shown in FIG. 3A and Table 3, on the 11th day after administration, the control animals were euthanized due to excessive tumor growth. The T/C value on the 11$^{th}$ day after administration of compound 6 at a dose of 100 mg/kg, p.o., qd regimen was 30% (P<0.001). The T/C value on the 11$^{th}$ day after administration of BR in the dual drug combination group reached 2% (P<0.001; 16 CR and 56 PR; remission rate was 100%). The T/C value on the 11$^{th}$ day after administration of the compound 6 with BR in the triple drug combination group reached 1% (P<0.001; 36 CR and 36 PR; the remission rate was 100%). Although there was no significant difference in anti-tumor activity and remission rate between dual therapy (BR) and triple therapy (Compound 6+BR), more CR was documented for the triple therapy comprising Compound 6. The advantages of the triple therapy were further manifested after discontinuation of administration. On the 22$^{rd}$ day after administration, all animals in the triple therapy group had sustained tumor remission (36 CR, 36 PR, 100% remission rate), while only 33% of the animals in the dual therapy group maintained tumor remission (16 CR, 16 PR). The results showed that Compound 6 may effectively improve the clinical anti-tumor effect of bendamustine and rituximab.

2. Anti-Tumor Effect in Mouse Xenograft Model Bearing Human FL DOHH2 Cells Mouse Xenograft Tumor Model (1) The experimental method was as described in Example 1. In the in vitro cell experiments, DOHH2 was a human follicular lymphoma (FL, belonging to NHL) cell line that was relatively sensitive to Compound 6 treatment. Therefore, this experiment established a model of FL mouse xenograft tumor derived from DOHH2 cells (Andrew J Souers et al., ABT-199, a potent and selective BCL-2 inhibitor, achieves antitumor activity while sparing platelets. Nature Medicine vol 19, 202-208 (2013)), to evaluate the antitumor effect of Compound 6 in combination with BR.

(2) Experimental Results

Figure 4:
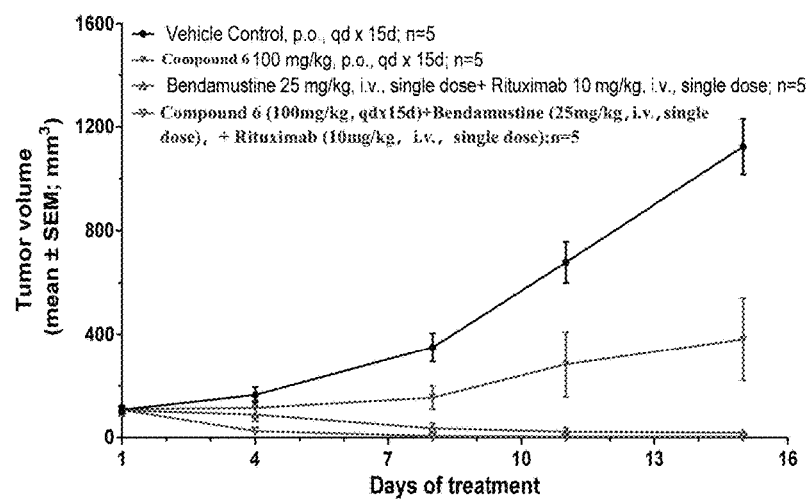
FIG. 4 shows the anti-tumor effect (A) and body weight change (B) caused by Compound 6 alone or in combination with BR in a human DOHH2 (FL) mouse xenograft model.
Figure 4:
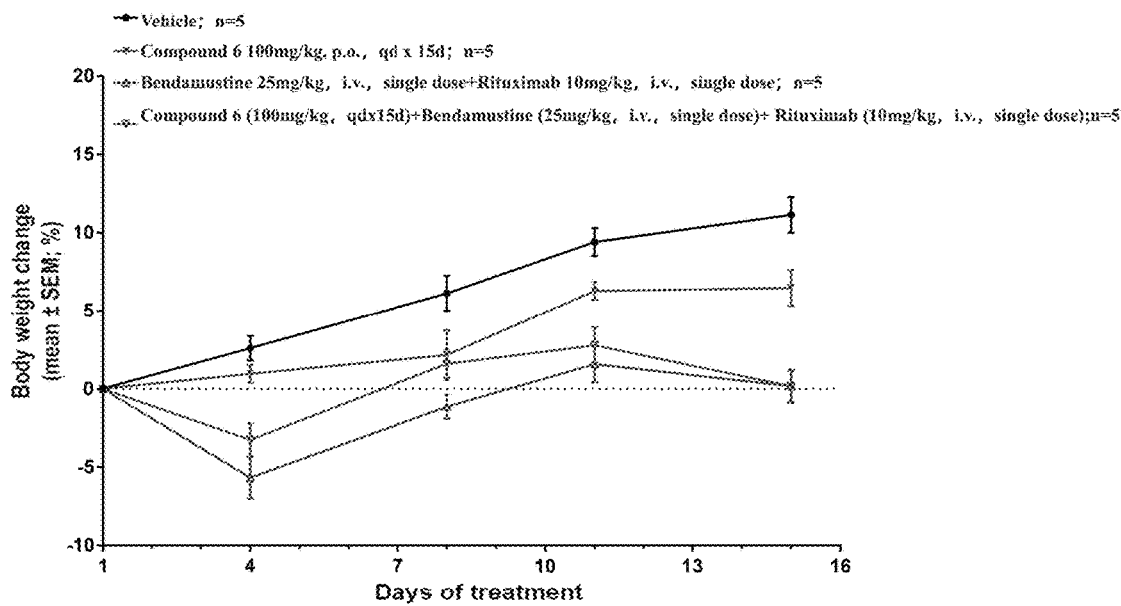

As shown in FIG. 4A and Table 4, in the 15-day treatment, the BR dual therapy showed effective anti-tumor activity with a T/C value of 1.4% (P<0.01; 1/5 CR and 4/5 PR, the remission rate was 100%). Compound 6 showed a signifi-

TABLE 3

Anti-tumor effects of Compound 6 alone or in combination with BR in human OCI-LY8 (DLBCL) mouse xenograft tumor model

| Treatment | RTV on the 11$^{th}$ day after administration (mean ± standard error) | T/C (%) on the 11$^{th}$ day after administration | On the 11$^{th}$ day after administration (remission rate %$^a$) | Synergistic factor on the 11th day after administration | RTV on the 22$^{nd}$ day after administration (mean ± standard error) | T/C$^{BR}$ (%) on the 22$^{nd}$ day after administration | On the 22$^{nd}$ day after administration (remission rate %$^a$) |
|---|---|---|---|---|---|---|---|
| Solvent | 18.80 ± 1.2 | — | 0/6 CR, 0/6 PR(0%) | — | — | — | — |
| Cpd. 6, 100 mg/kg | 5.54 ± 1.78*** | 30 | 0/5 CR, 0/5 PR(0%) | — | — | — | — |
| Bendamustine, 25 mg/kg + rituximab, 10 mg/kg | 0.36 ± 0.08*** | 2 | 1/6 CR, 5/6 PR(100%) | — | 7.89 ± 2.63 | — | 1/6 CR, 1/6 PR(33%) |
| Cpd. 6, 100 mg/kg + bendamustine + rituximab | 0.14 ± 0.07***# | 1 | 3/6 CR, 3/6 PR(100%) | 0.75 | 0.18 ± 0.09† | 1 | 3/6 CR, 3/6 PR(100%) |

***P < 0.001, compared with the vehicle control group;
P < 0.05, compared with the single Compound 6 group;
†P < 0.05, compared with the BR group;
$^a$remission including CR, PR and SD.
Synergy factor = 1, additive effect; synergistic factor < 1, antagonistic effect.

(3) Summary

Compound 6 in combination with rituximab and bendamustine had no significant side effects (FIG. 2B) and significantly increased the anti-tumor effect of each single agent in the OCI-LY8 human DLBCL cell mouse xenograft tumor model. Therefore, the combination of Compound 6 with rituximab and bendamustine may clinically benefit patients with diffuse large B-cell lymphoma (DLBCL).

cant anti-tumor effect after administration of 100 mg/kg, p.o., qd regimen, with a T/C value of 28% (P<0.01). The triple therapy of Compound 6 plus BR almost result in complete tumor regression with a T/C value of 0.2% (P<0.001; 2/5 CR and 3/5 PR; the remission rate was 100%). The data indicated that Compound 6 in combination with BR could achieve more CR, confirming the effectiveness of the triple therapy on the FL model.

TABLE 4

Anti-tumor effects of Compound 6 alone or in combination with BR in human DOHH2 (FL) mouse xenograft tumor model (APS-EF-75-2017-DOHH2)

| Treatment | RTV on the 15$^{th}$ day after administration (mean ± standard error) | T/C (%) on the 15$^{th}$ day after administration | Tumor remission rate on the 15$^{th}$ day after administration %$^a$ | Synergistic factor on the 15$^{th}$ day after administration |
|---|---|---|---|---|
| Vehicle control | 11.02 ± 1.49 | — | 0/5 CR, 0/5 PR(0%) | — |
| Cpd. 6, 100 mg/kg | 3.06 ± 0.79** | 28 | 0/5 CR, 0/5 PR(0%) | — |

TABLE 4-continued

Anti-tumor effects of Compound 6 alone or in combination with BR in
human DOHH2 (FL) mouse xenograft tumor model (APS-EF-75-2017-DOHH2)

| Treatment | RTV on the 15$^{th}$ day after administration (mean ± standard error) | T/C (%) on the 15$^{th}$ day after administration | Tumor remission rate on the 15$^{th}$ day after administration %$^a$ | Synergistic factor on the 15$^{th}$ day after administration |
|---|---|---|---|---|
| Bendamustine, 25 mg/kg + rituximab, 10 mg/kg (BR) | 0.14 ± 0.07** | 1.4 | 1/5 CR, 4/5 PR(100%) | — |
| Cpd. 6 + BR | 0.04 ± 0.02**⁺ | 0.2 | 2/5 CR, 3/5 PR(100%) | 0.97 |

**P < 0.01, compared with vehicle control group;
⁺P < 0.05, compared with the Compound 6 group;
$^a$remission including CR, PR and SD.
Synergy factor = 1, additive effect; synergistic factor < 1, antagonistic effect.

(3) Summary

Compound 6 in combination with rituximab and bendamustine had no significant side effects (FIG. 2B) and significantly increased the anti-tumor effect of each single drug in the human DOHH2 (FL) mouse xenograft tumor model. Therefore, the combination of Compound 6 with rituximab and bendamustine may clinically benefit patients with follicular lymphoma (FL).

Example 5. Effects of Compound 6 in Combination with CHOP (i.e, Cyclophosphamide, Doxorubicin, Vincristine, and Prednisone) in DOHH2 (FL) Model (1) The experimental method was as described in Example 1. In the DOHH2 model (Andrew J Souers et al., ABT-199, a potent and selective BCL-2 inhibitor, achieves antitumor activity while sparing platelets. Nature Medicine vol 19, 202-208 (2013)), the anti-tumor effect of Compound 6 in combination with CHOP (i.e., cyclophosphamide, doxorubicin, vincristine and prednisone) was additionally evaluated. CHOP included: cyclophosphamide, 20 mg/kg, intraperitoneal injection, administered on the 1st and 9th days; doxorubicin, 2 mg/kg, intravenous injection, administered on the 1st day; vincristine, 0.1 mg/kg, intravenous injection, administered on the 1st and 9th days; prednisone, 0.5 mg/kg, orally administered on the 1st day. Among them, cyclophosphamide (batch number 09121921) was purchased from Jiangsu Hengrui Medicine Co., Ltd. Cyclophosphamide was administered intraperitoneally. The injected dose was 10 mL/kg (0.2 mL/mouse). The agent was dissolved in saline.

Doxorubicin (batch number 20061106) was purchased from Shanghai Richem Inc. Doxorubicin was administered by intravenous injection at a dose of 10 mL/kg (0.2 mL/mouse). The agent was dissolved in saline. Vincristine (batch number 0708v1) was purchased from Shenzhen Main Luck Pharmaceuticals Inc. Vincristine was administered by intravenous injection at a dose of 10 mL/kg (0.2 mL/mouse). The agent was dissolved in saline. Prednisone (batch number M0412A) was purchased from Dalian Meilun Biotechnology Co., Ltd. Prednisone was administered by oral gavage at a dose of 10 mL/kg (0.2 mL/mouse). The agent was dissolved in 10% PEG 400/5% EL/85% PBS. The dosage formulations were prepared freshly prior to use. The preparation and use of the dosage formulations were always carried out under sterile conditions.

(2) Experimental Results

Figure 5:
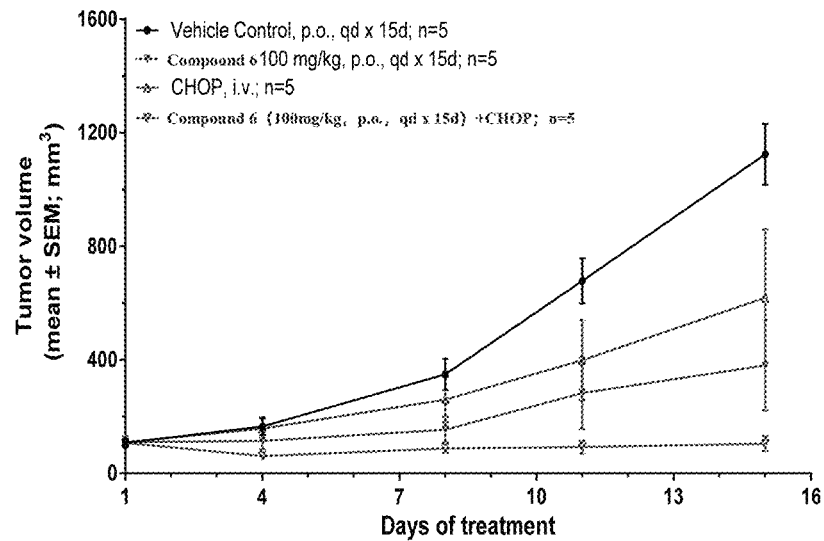
FIG. 5 shows the anti-tumor effect (A) and body weight change (B) caused by Compound 6 alone or in combination with CHOP in a human DOHH2 (FL) mouse xenograft model.
Figure 5:
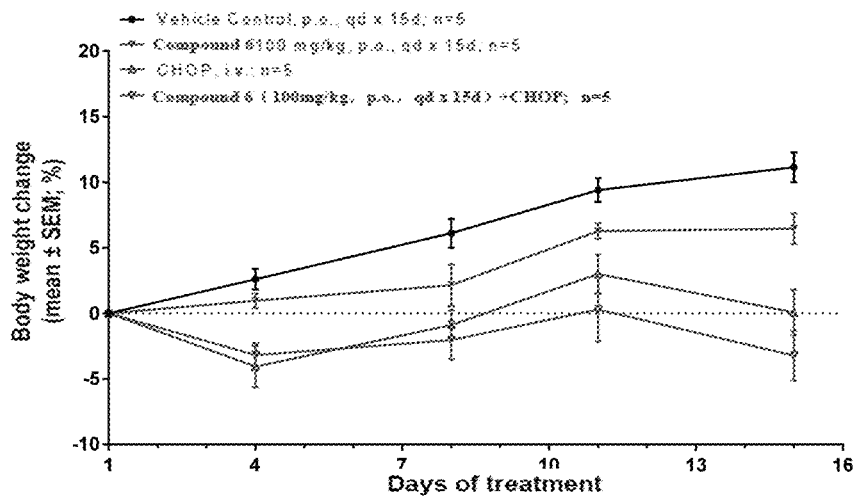

As shown in FIG. 5A and Table 5, after 15 days of treatment, the T/C values of the group of single Compound 6 at 100 mg/kg dose and the group of CHOP treatment were 28% (P<0.01) and 50% (P<0.05), respectively, without remission of PR or CR. Compound 6 in combination with CHOP showed significantly enhanced effect of growth inhibition with a T/C value of 9% (P<0.001; 0/5 CR and 4/5 PR; remission rate 80%).

TABLE 5

Anti-tumor effects of Compound 6 alone or in combination
with CHOP in human DOHH2 (FL) mouse xenograft tumor model

| Treatment | RTV on the 15$^{th}$ day after administration (mean ± standard error) | T/C (%) on the 15$^{th}$ day after administration | Tumor remission rate on the 15$^{th}$ day after administration %$^a$ | Synergistic factor on the 15th day after administration |
|---|---|---|---|---|
| Solvent control | 11.02 ± 1.49 | — | 0/5 CR, 0/5 PR(0%) | — |
| Cpd. 6, 100 mg/kg | 3.06 ± 0.79** | 28 | 0/5 CR, 0/5 PR(0%) | — |
| CHOP | 5.51 ± 1.50* | 50 | 0/5 CR, 0/5 PR(0%) | — |
| Cpd. 6 + CHOP | 0.95 ± 0.22*** | 9 | 0/5 CR, 4/5 PR(80%) | 1.61 |

*P < 0.05,
**P < 0.01,
***P < 0.001, compared with the vehicle control group;
$^a$remission including CR, PR and SD.
Synergy factor = 1, additive effect; synergistic factor < 1, antagonistic effect.

(3) Summary

Compound 6 in combination with CHOP had no significant side effects (FIG. 5B), which significantly increased the antitumor effect of each single agent in the human DOHH2 (FL) mouse xenograft tumor model, and had a significant synergistic effect (synergistic factor was 1.61>1). These results suggest that the combination of Compound 6 and CHOP can bring clinical benefit to patients with follicular lymphoma (FL).

What is claimed is:

1. A combination comprising:
a) a Bcl-2 inhibitor of formula:

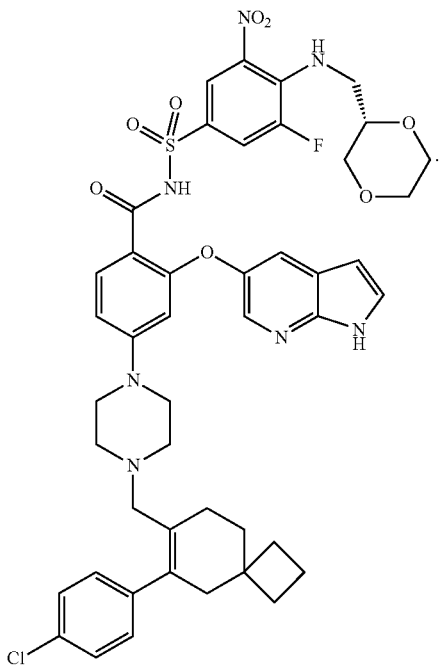 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

or a pharmaceutically acceptable salt thereof; and
b) an anti-CD20 mAb.

2. The combination according to claim 1, further comprising Bendamustine.

3. The combination according to claim 1, wherein the anti-CD20 mAb is selected from the group consisting of: Rituximab, IF5, Ibritumomab tiuxetan, tositumomab, ocrelizumab, veltuzumab, ofatumumab, obinutuzumab, AME133V, Pro13192, GA101, and TRU-015.

4. The combination according to claim 1, which further comprises a pharmaceutically acceptable carrier, diluent, or excipient.

5. A method of treatment of a disease, comprising administering to a subject in need thereof a therapeutically effective amount of:

a) a Bcl-2 inhibitor of formula:

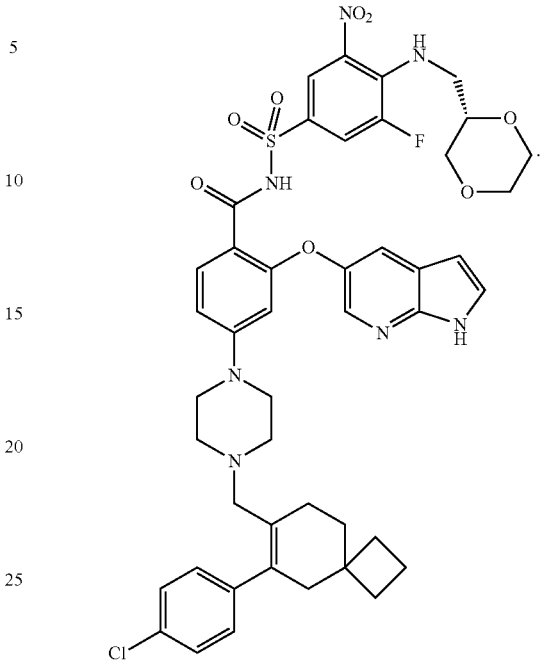

or a pharmaceutically acceptable salt thereof; and
b) an anti-CD20 mAb selected from the group consisting of: rituximab, IF5, ibritumomab tiuxetan, tositumomab, ocrelizumab, veltuzumab, ofatumumab, obinutuzumab, AME133V, Pro13192, GA101, and TRU-015,
wherein the disease is selected from the group consisting of cancer, rheumatoid arthritis (RA), granulomatosis with polyangiitis (GPA), and microscopic polyangiitis.

6. The method according to claim 5, wherein the cancer is selected from the group consisting of: bladder cancer, breast cancer, cervical cancer, colon cancer, colorectal cancer, esophageal cancer, head and neck cancer, liver cancer, lung cancer, small cell lung cancer, non-small cell lung cancer, melanoma, myeloma, neuroblastoma, ovarian cancer, pancreatic cancer, prostate cancer, kidney cancer, sarcoma, osteosarcoma, skin cancer, squamous cell cancer, gastric cancer, testicular cancer, thyroid cancer, uterine cancer, mesothelioma, cholangiocarcinoma, leiomyosarcoma, liposarcoma, melanoma, nasopharyngeal carcinoma, neuroendocrine carcinoma, ovarian cancer, renal cancer, salivary gland cancer, or metastases induced by spindle cancer, non-Hodgkin's lymphoma (NHL), Hodgkin's lymphoma, acute myeloid leukemia (AML), acute lymphoblastic leukemia (ALL), diffuse large B-cell lymphoma (DLBCL), follicular lymphoma (FL), chronic lymphocytic leukemia (CLL)/small lymphocytic lymphoma (SLL), marginal zone lymphoma (MZL), chronic myelogenous leukemia (CML), mantle cell lymphoma (MCL), and Waldenstrom's macroglobulinemia (WM).

7. The method according to claim 6, wherein the Bcl-2 inhibitor or a pharmaceutically acceptable salt or solvate thereof is administered in an amount of about 0.0025-1500 mg/day, and the anti-CD20 mAb is administered in an amount of about 0.0025-800 mg/day.

8. The method according to claim 5, wherein the Bcl-2 inhibitor and the anti-CD20 mAb are administered simultaneously, sequentially, or alternately.

9. A method of treatment of a disease, comprising administering to a subject in need thereof a therapeutically effective amount of a) a Bcl-2 inhibitor of formula:

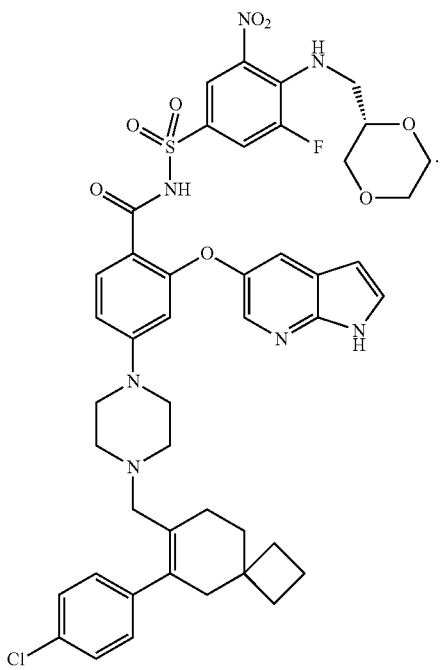 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

or a pharmaceutically acceptable salt thereof; and
b) an anti-CD20 mAb selected from the group consisting of: rituximab, IF5, ibritumomab tiuxetan, tositumomab, ocrelizumab, veltuzumab, ofatumumab, obinutuzumab, AME133V, Pro13192, GA101, and TRU-015, and
c) Bendamustine, wherein the disease is selected from the group consisting of cancer, rheumatoid arthritis (RA), granulomatosis with polyangiitis (GPA), and microscopic polyangiitis.

10. The method according to claim 9, wherein the cancer is selected from the group consisting of: bladder cancer, breast cancer, cervical cancer, colon cancer, colorectal cancer, esophageal cancer, head and neck cancer, liver cancer, lung cancer, small cell lung cancer, non-small cell lung cancer, melanoma, myeloma, neuroblastoma, ovarian cancer, pancreatic cancer, prostate cancer, kidney cancer, sarcoma, osteosarcoma, skin cancer, squamous cell cancer, gastric cancer, testicular cancer, thyroid cancer, uterine cancer, mesothelioma, cholangiocarcinoma, leiomyosarcoma, liposarcoma, melanoma, nasopharyngeal carcinoma, neuroendocrine carcinoma, ovarian cancer, renal cancer, salivary gland cancer, or metastases induced by spindle cancer, non-Hodgkin's lymphoma (NHL), Hodgkin's lymphoma, acute myeloid leukemia (AML), acute lymphoblastic leukemia (ALL), diffuse large B-cell lymphoma (DLBCL), follicular lymphoma (FL), chronic lymphocytic leukemia (CLL)/small lymphocytic lymphoma (SLL), marginal zone lymphoma (MZL), chronic myelogenous leukemia (CML), mantle cell lymphoma (MCL), Waldenstrom's macroglobulinemia (WM).

11. The method according to claim 9, wherein the Bcl-2 inhibitor or a pharmaceutically acceptable salt or solvate thereof is administered in an amount of about 0.0025-1500 mg/day, the anti-CD20 mAb is administered in an amount of about 0.0025-800 mg/day, and the Bendamustine is administered in an amount of about 0.0025-500 mg/day.

12. The method according to claim 9, wherein the Bcl-2 inhibitor, anti-CD20 mAb, and Bendamustine are administered simultaneously, sequentially, or alternately.

* * * * *

UNITED STATES PATENT AND TRADEMARK OFFICE
CERTIFICATE OF CORRECTION

PATENT NO. : 11,554,127 B2  
APPLICATION NO. : 16/648593  
DATED : January 17, 2023  
INVENTOR(S) : Dajun Yang et al.

Page 1 of 2

It is certified that error appears in the above-identified patent and that said Letters Patent is hereby corrected as shown below:

In the Claims

Column 101, Lines 11-45, delete "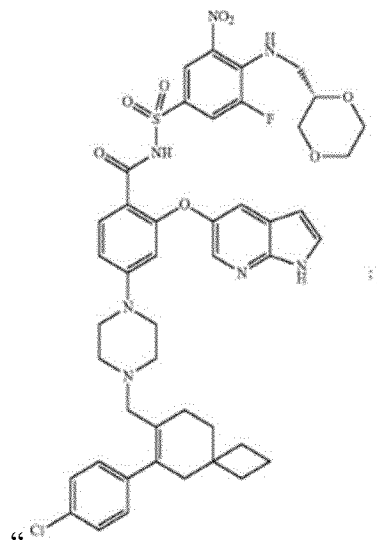" and insert therefor --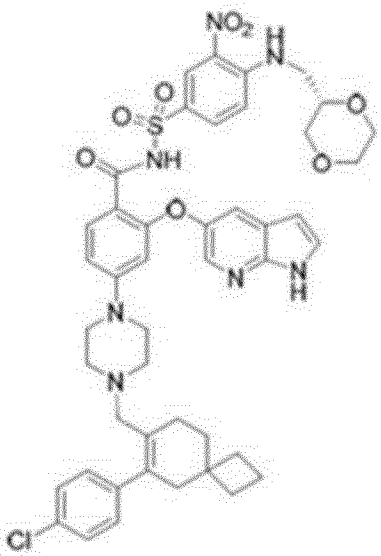--

Signed and Sealed this  
Twenty-eighth Day of February, 2023

Katherine Kelly Vidal  
*Director of the United States Patent and Trademark Office*

CERTIFICATE OF CORRECTION (continued)
U.S. Pat. No. 11,554,127 B2

Column 102, Lines 3-29, delete

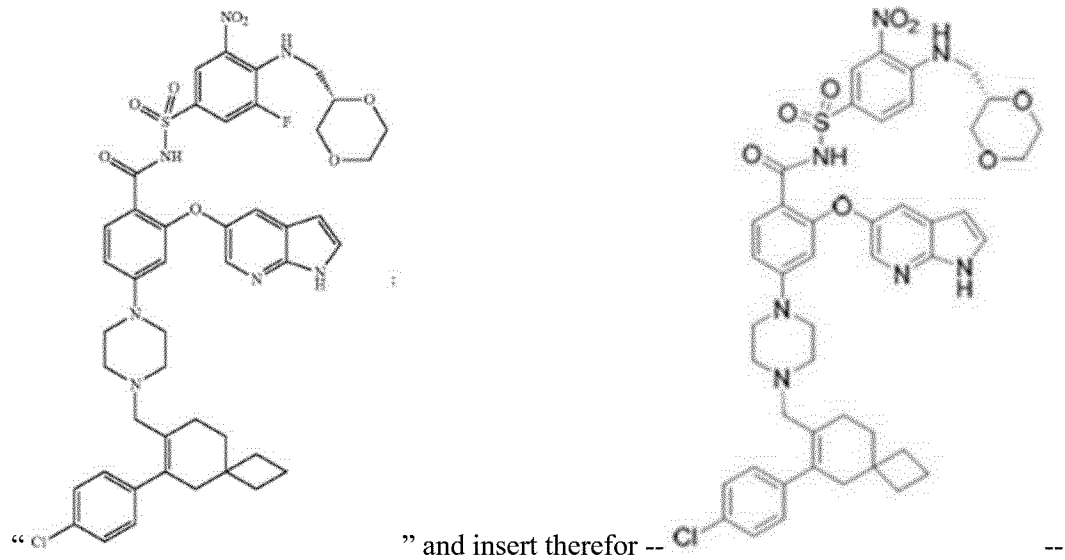

" and insert therefor -- --

Column 103, Lines 3-29, delete

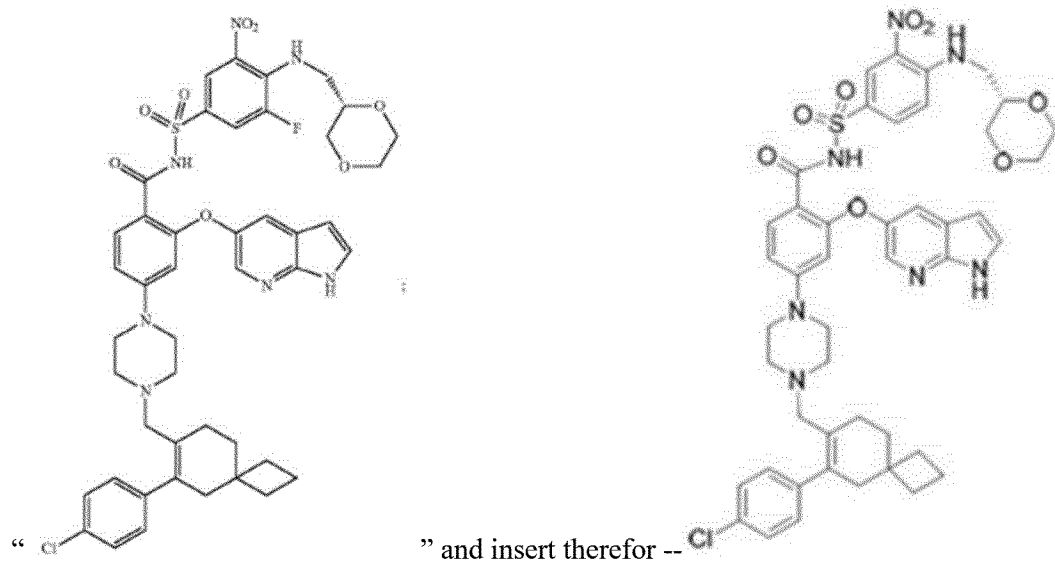

" and insert therefor -- --